(12) United States Patent
Miller et al.

(10) Patent No.: US 10,631,870 B2
(45) Date of Patent: Apr. 28, 2020

(54) METHOD AND APPARATUS FOR OCCLUDING A BLOOD VESSEL

(71) Applicant: AMSEL MEDICAL CORPORATION, Cambridge, MA (US)

(72) Inventors: Arnold Miller, Cambridge, MA (US); Avraham Rami Lore, Kiryat Tivon (IL)

(73) Assignee: AMSEL MEDICAL CORPORATION, Cambridge, MA (US)

( * ) Notice: Subject to any disclaimer, the term of this patent is extended or adjusted under 35 U.S.C. 154(b) by 424 days.

(21) Appl. No.: 15/044,323

(22) Filed: Feb. 16, 2016

(65) Prior Publication Data

US 2016/0157864 A1     Jun. 9, 2016

Related U.S. Application Data

(63) Continuation of application No. 13/857,424, filed on Apr. 5, 2013, now abandoned, and a continuation-in-part of application No. 13/348,416, filed on Jan. 11, 2012, now abandoned.

(60) Provisional application No. 61/620,787, filed on Apr. 5, 2012, provisional application No. 61/431,609, filed on Jan. 11, 2011.

(51) Int. Cl.
| A61B 17/122 | (2006.01) |
| A61B 17/128 | (2006.01) |
| A61B 17/12  | (2006.01) |
| A61B 17/00  | (2006.01) |
| A61B 17/064 | (2006.01) |

(52) U.S. Cl.
CPC ...... *A61B 17/122* (2013.01); *A61B 17/00008* (2013.01); *A61B 17/12* (2013.01); *A61B 17/12009* (2013.01); *A61B 17/1214* (2013.01); *A61B 17/12022* (2013.01); *A61B 17/1285* (2013.01); *A61B 17/12145* (2013.01); *A61B 17/0643* (2013.01); *A61B 2017/00867* (2013.01); *A61B 2017/00986* (2013.01); *A61B 2017/12054* (2013.01)

(58) Field of Classification Search
CPC .. A61B 17/12022–12195; A61B 17/12; A61B 17/122–1285; A61B 2017/1205–12095; A61B 2017/1225; A61F 6/20–208
See application file for complete search history.

(56) References Cited

U.S. PATENT DOCUMENTS

| 8,133,242 B1 * | 3/2012 | Quinn | A61B 17/122 606/142 |
| 2005/0273135 A1 * | 12/2005 | Chanduszko | A61B 17/0057 606/213 |

(Continued)

*Primary Examiner* — Jonathan A Hollm

(57) ABSTRACT

Apparatus for percutaneously occluding a hollow structure, said apparatus comprising:
an occluder, said occluder comprising a first component and a second component, wherein said first component is configured so that it may assume (i) a diametrically-reduced configuration for disposition within the lumen of a hollow tube, and (ii) a diametrically-expanded configuration for disposition adjacent to the hollow structure, whereby to occlude the hollow structure, and further wherein said second component percutaneously connects said first component to a site remote from said first component.

6 Claims, 79 Drawing Sheets

(56) References Cited

U.S. PATENT DOCUMENTS

| | | | | |
|---|---|---|---|---|
| 2005/0288786 A1* | 12/2005 | Chanduszko | ...... | A61B 17/0057 623/11.11 |
| 2008/0077180 A1* | 3/2008 | Kladakis | ............ | A61B 17/0057 606/216 |
| 2009/0125038 A1* | 5/2009 | Ewers | ................ | A61B 17/0487 606/142 |
| 2013/0046331 A1* | 2/2013 | Christensen | ........... | A61B 17/12 606/200 |

* cited by examiner

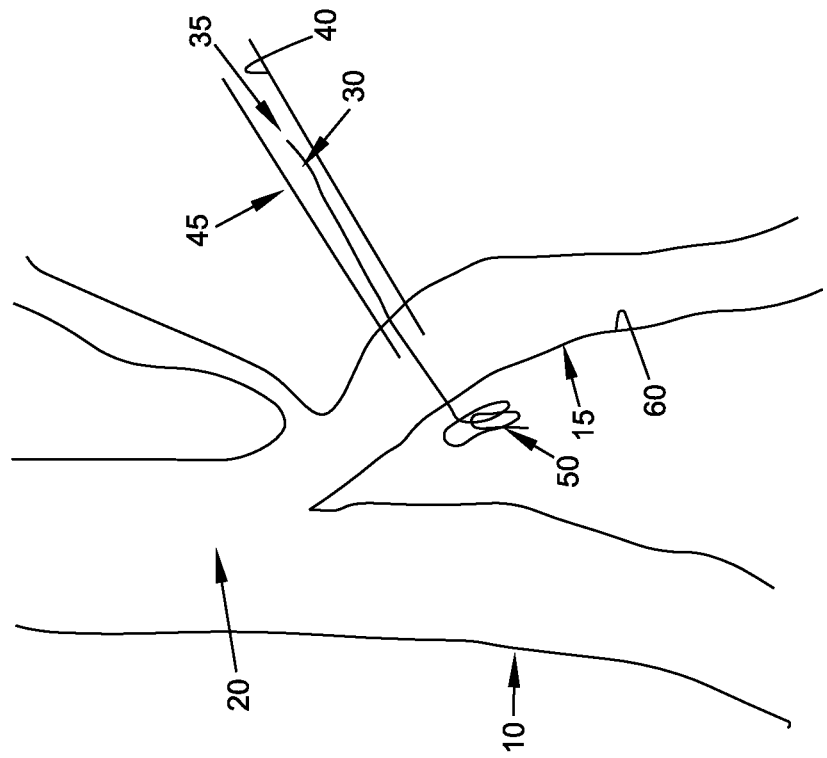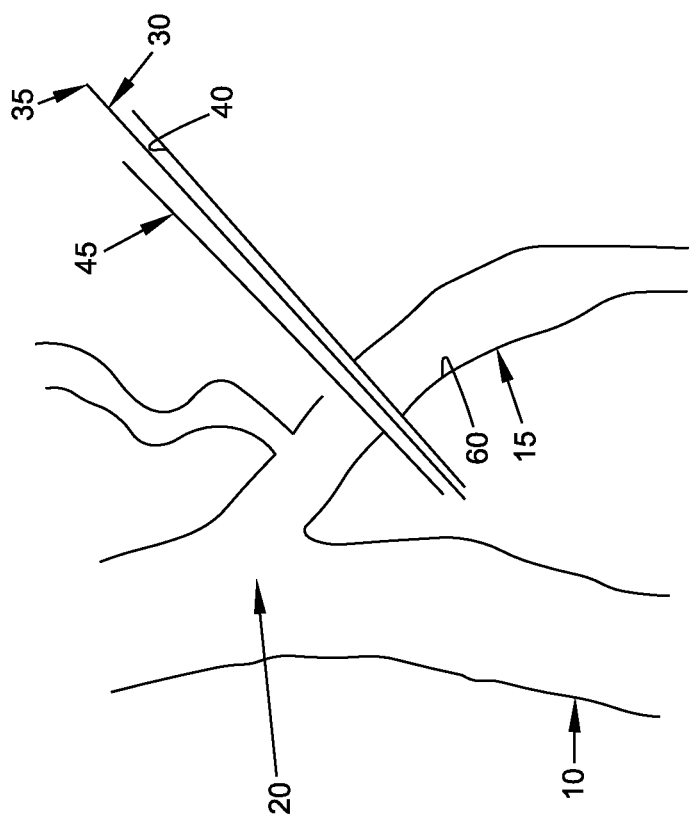

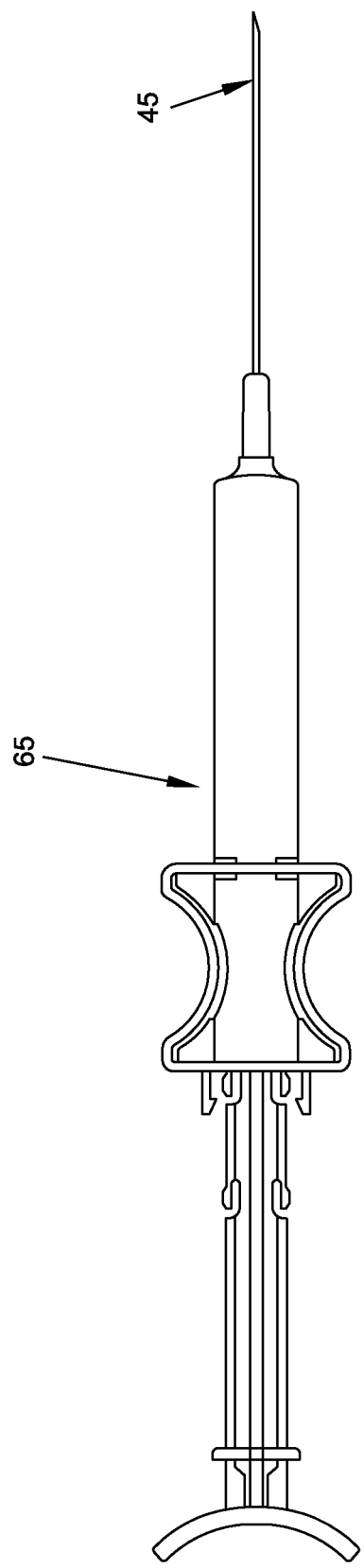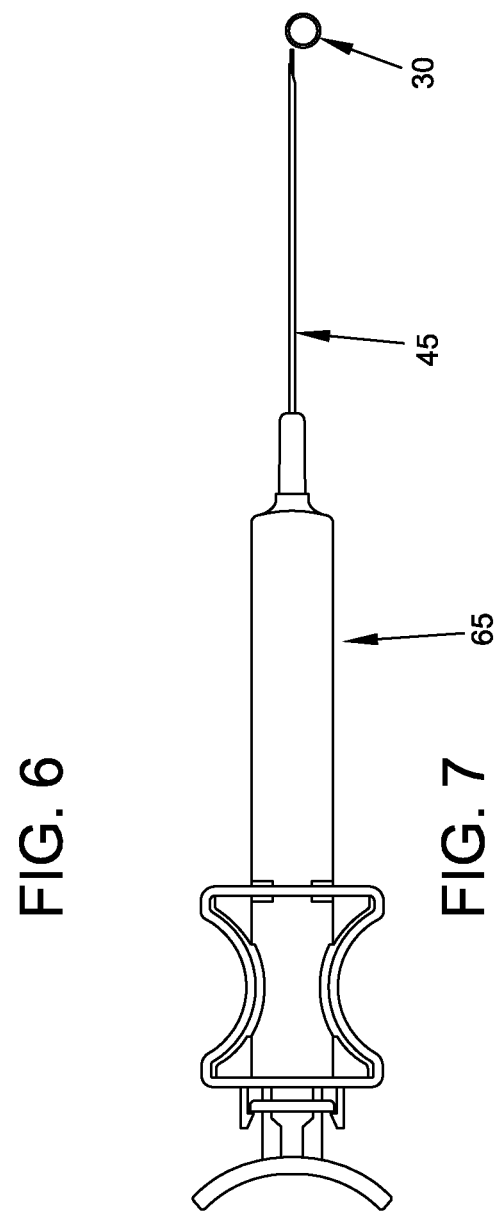
FIG. 6
FIG. 7

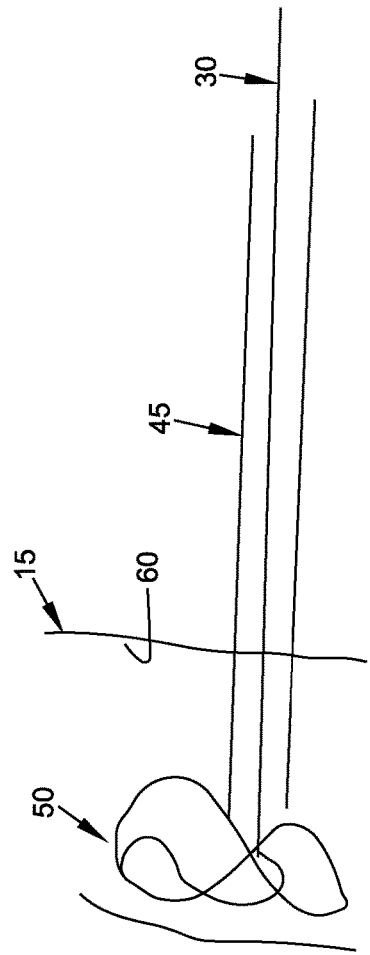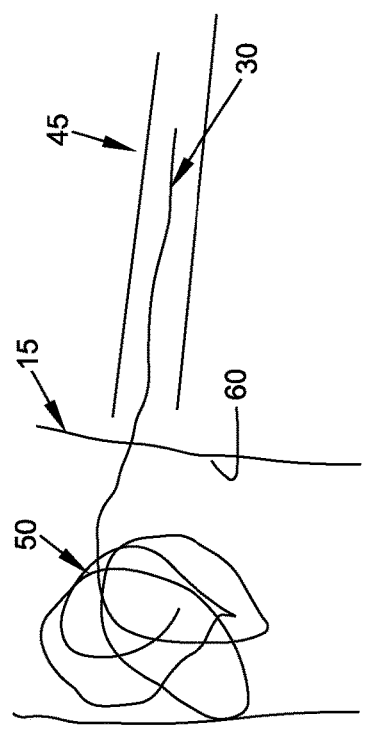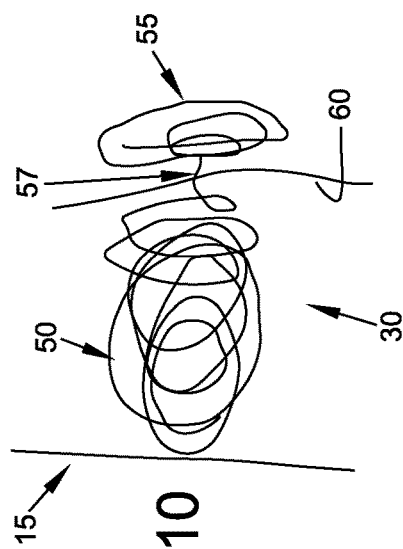

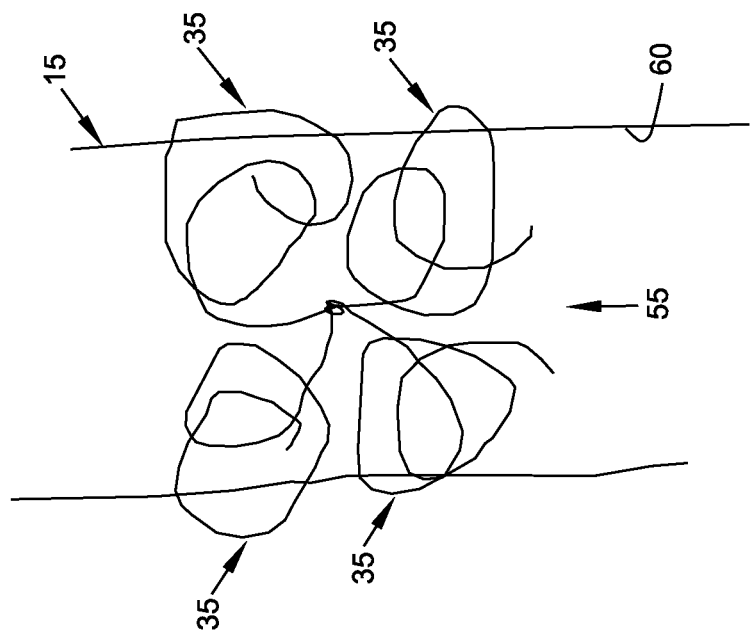
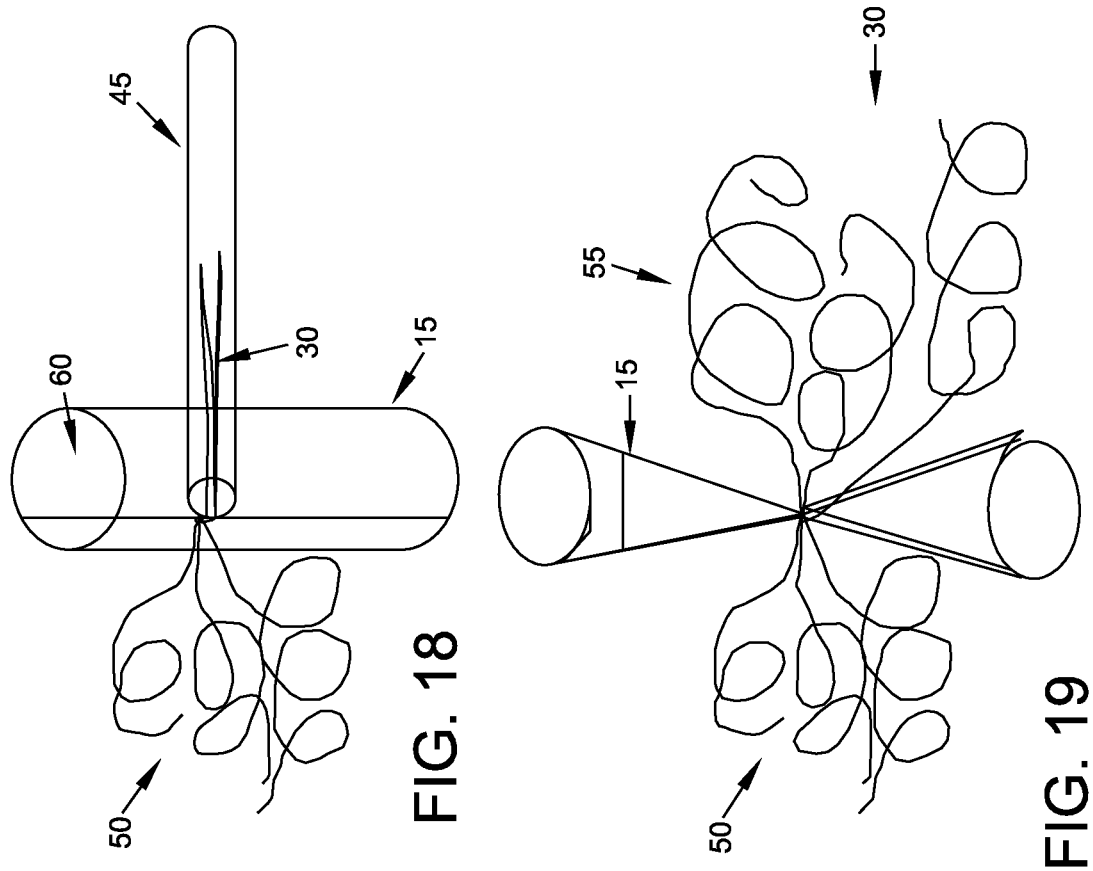

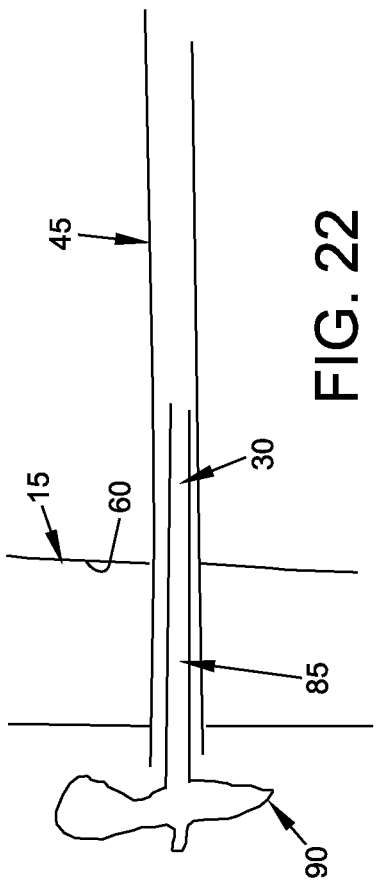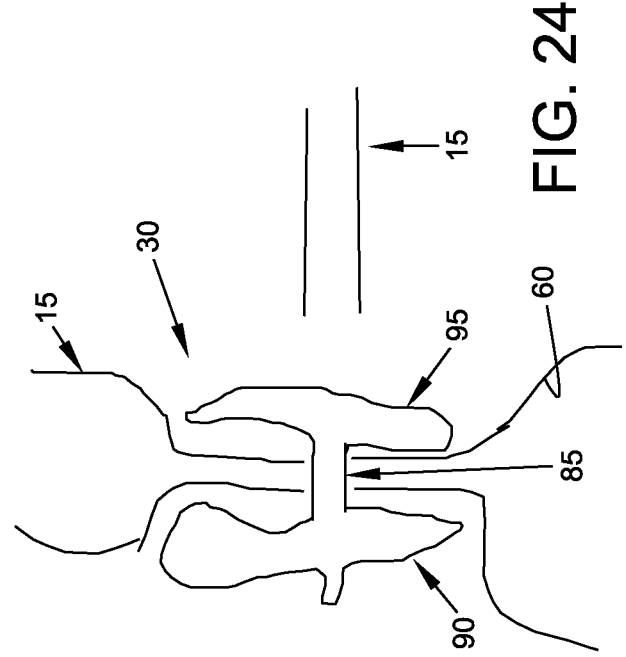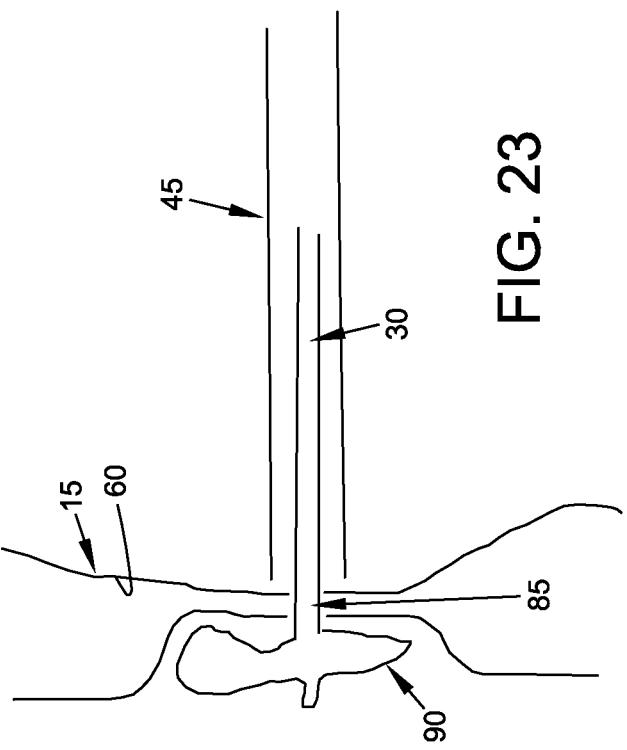

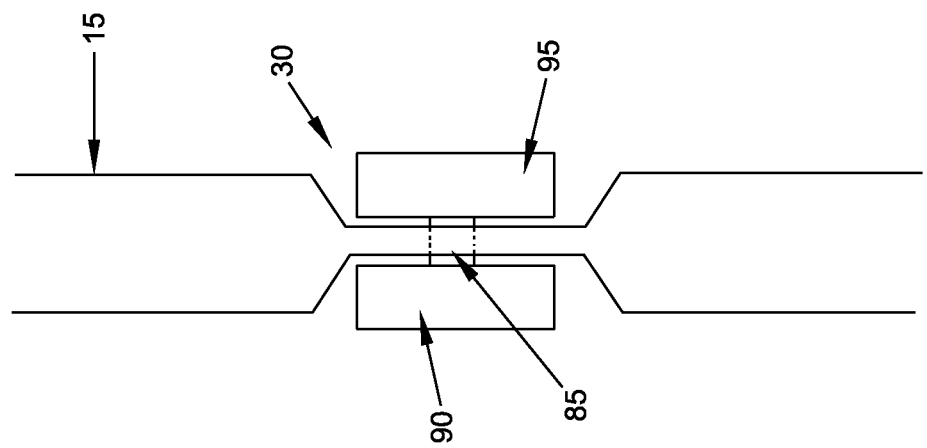
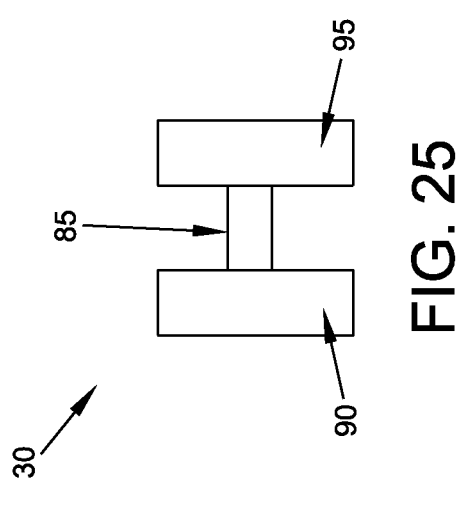
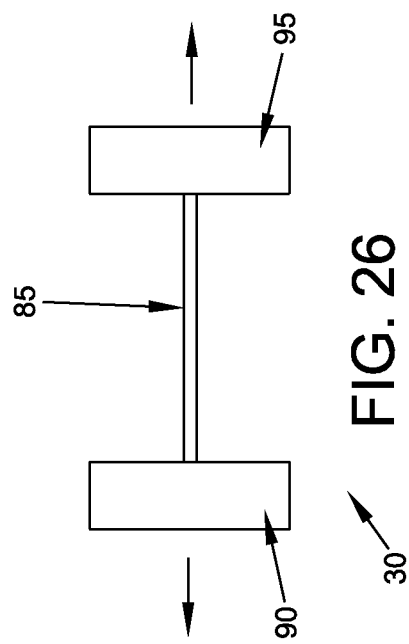

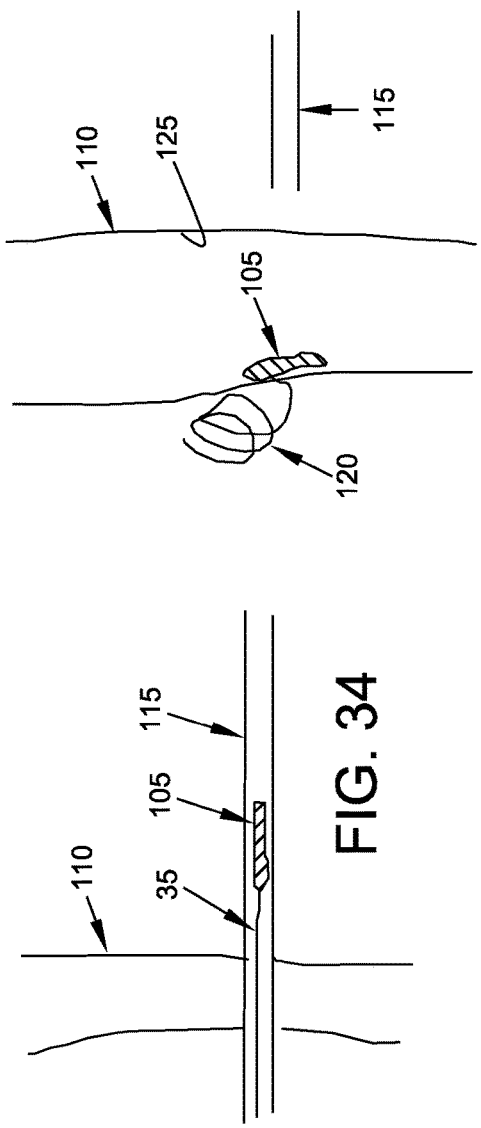
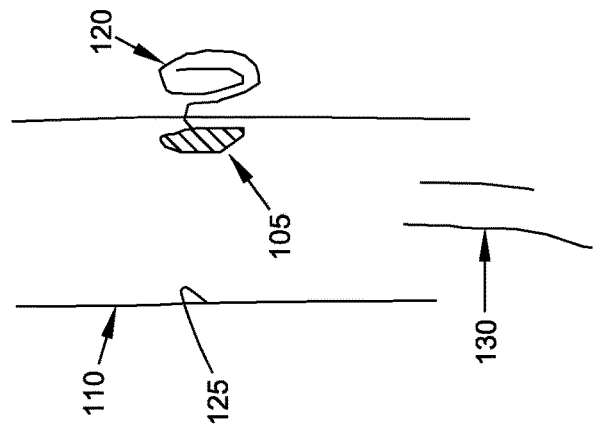
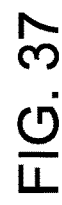
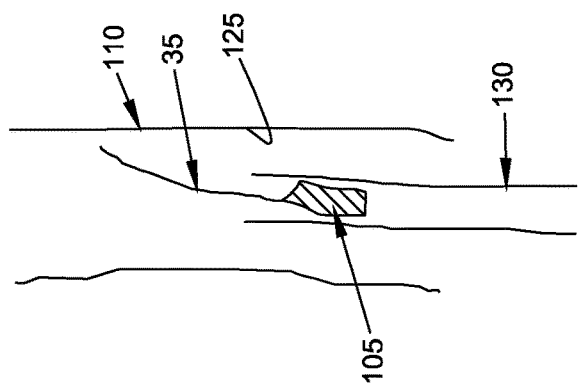

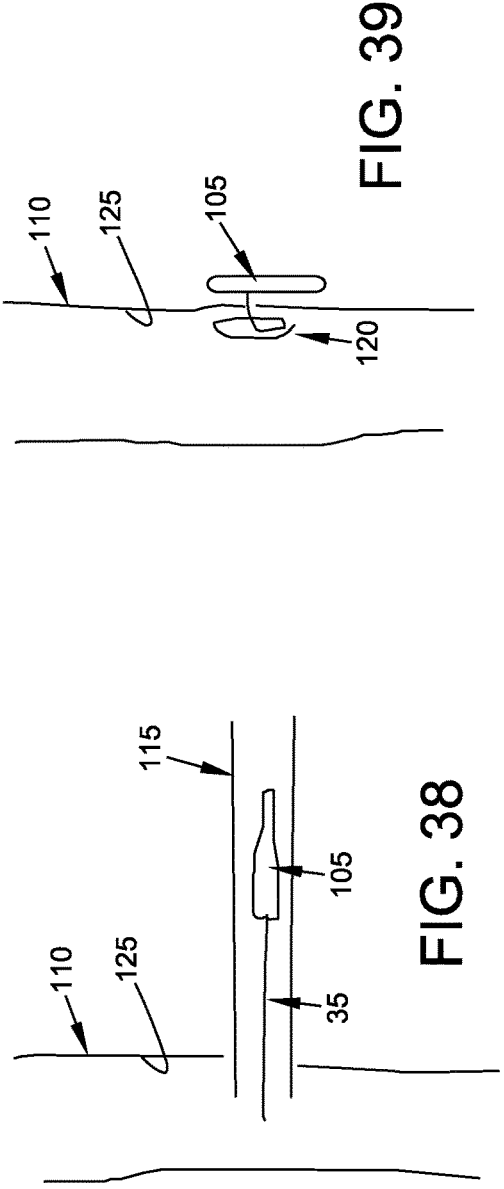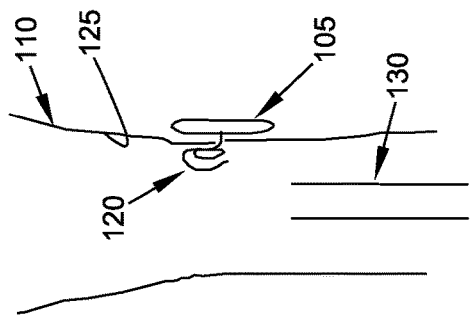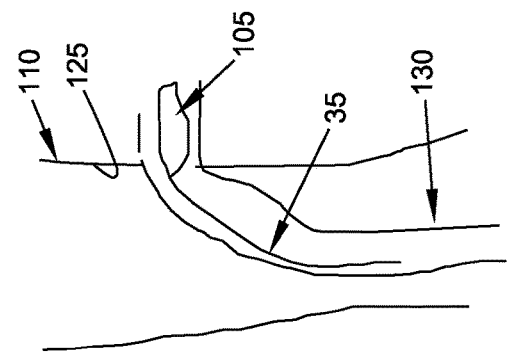

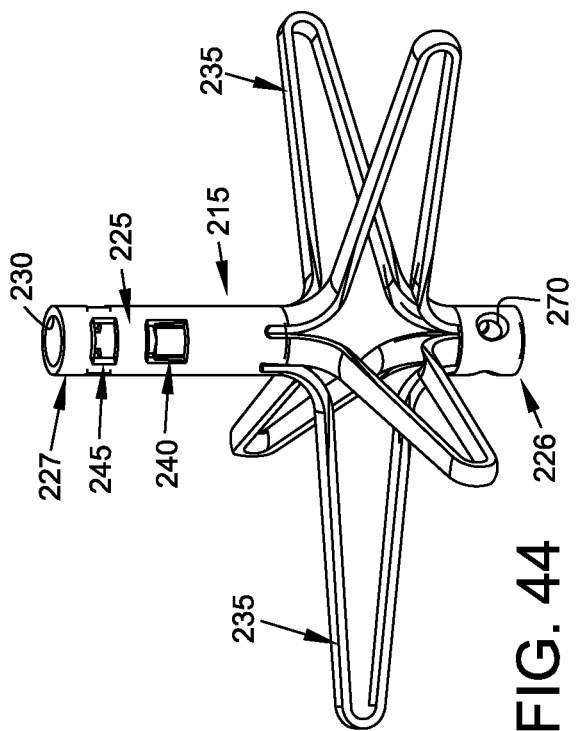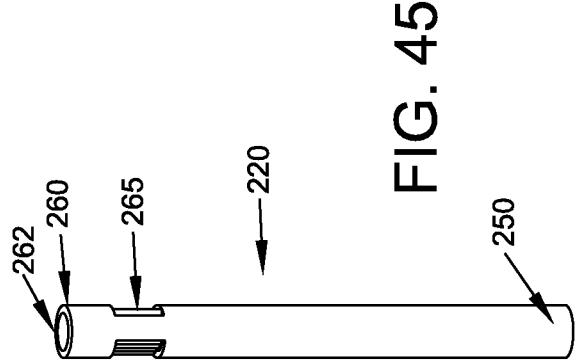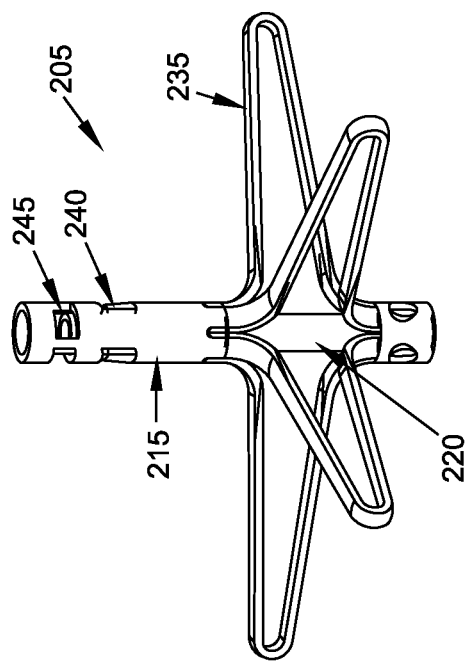

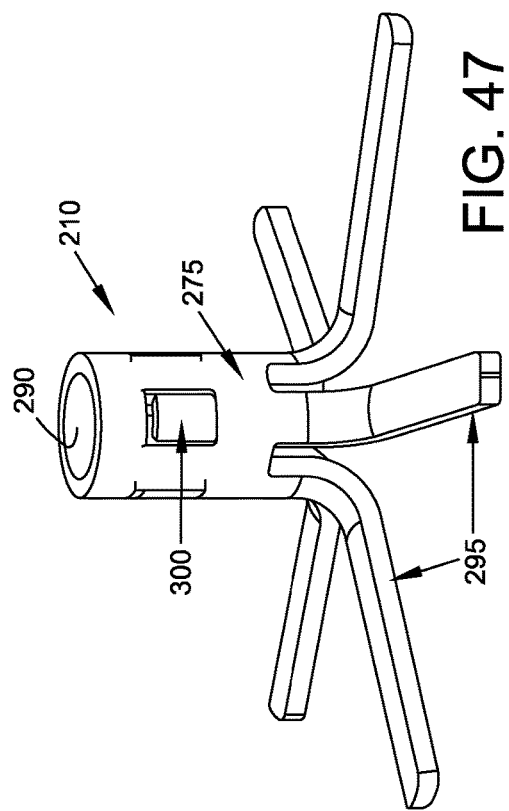
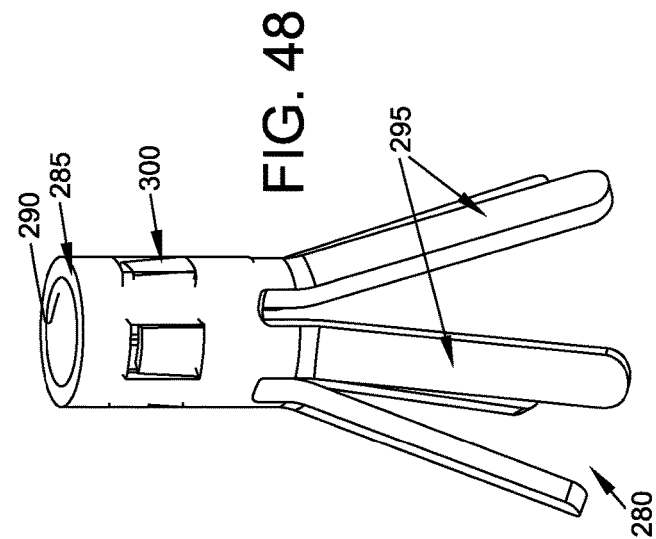
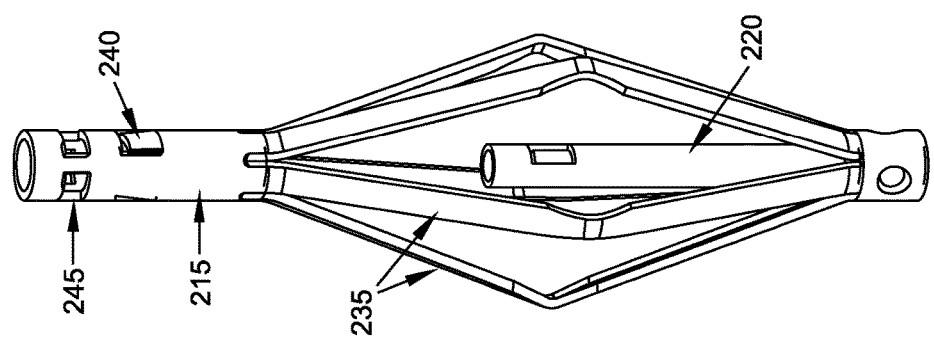

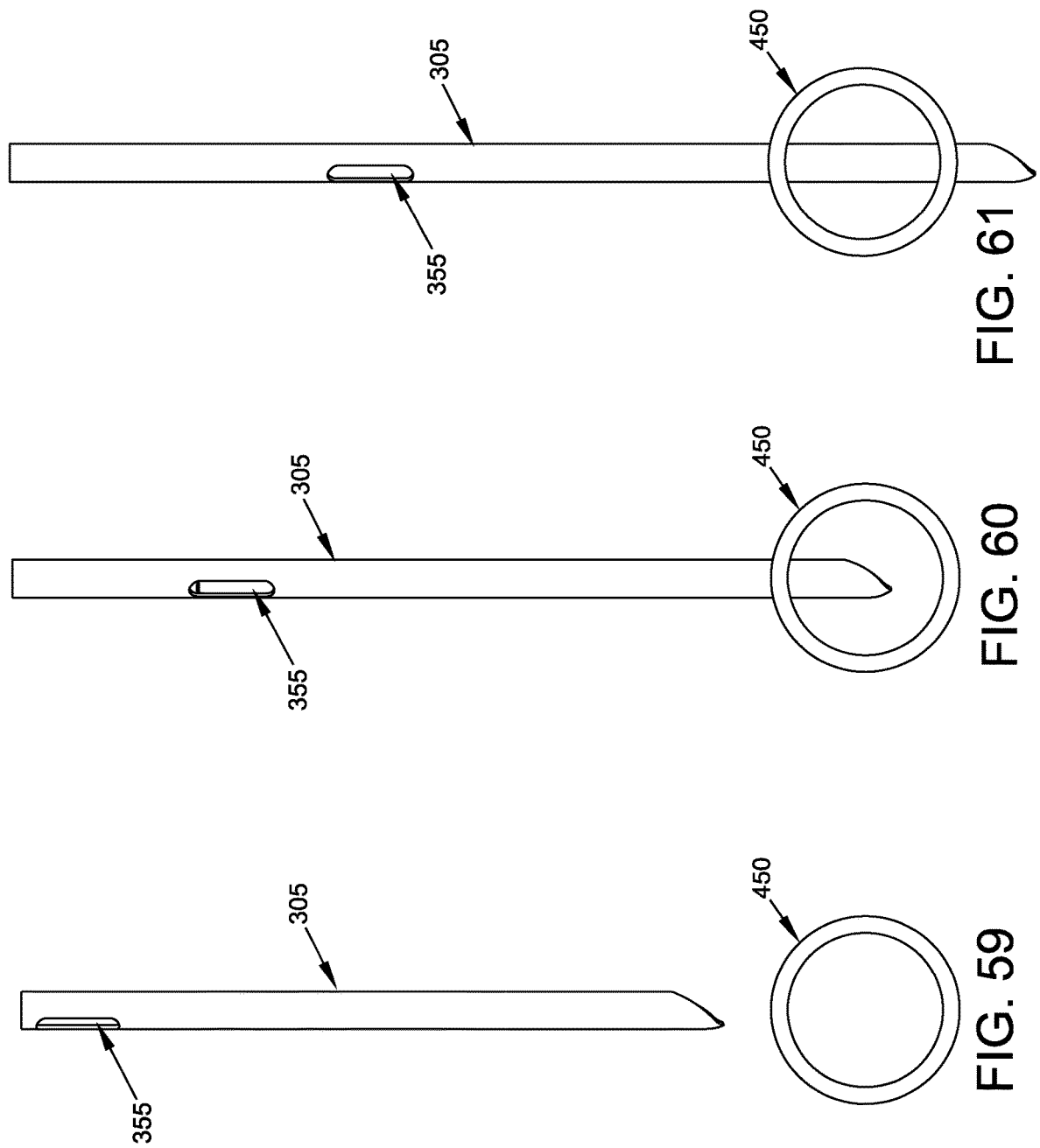

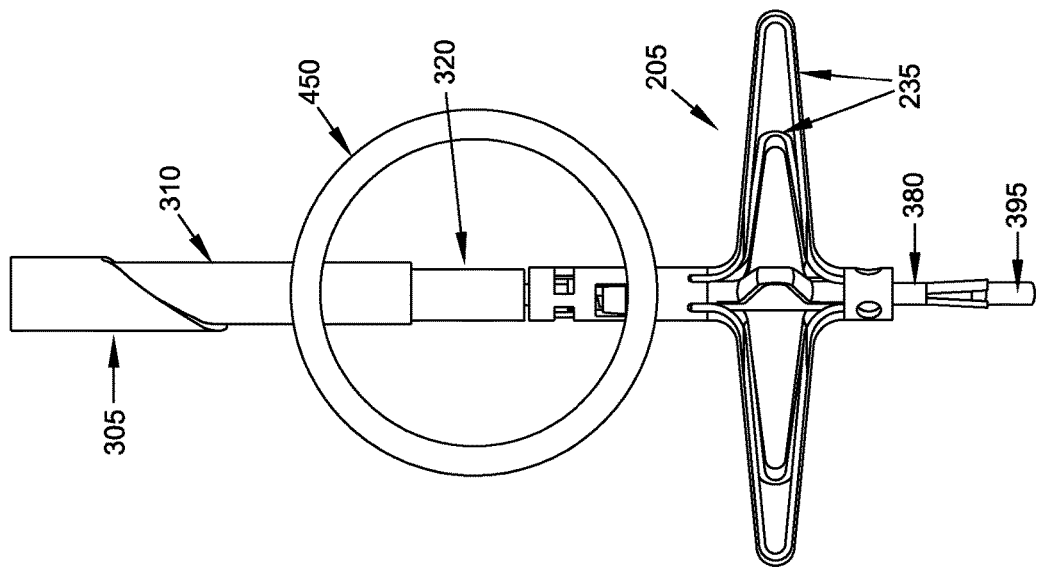
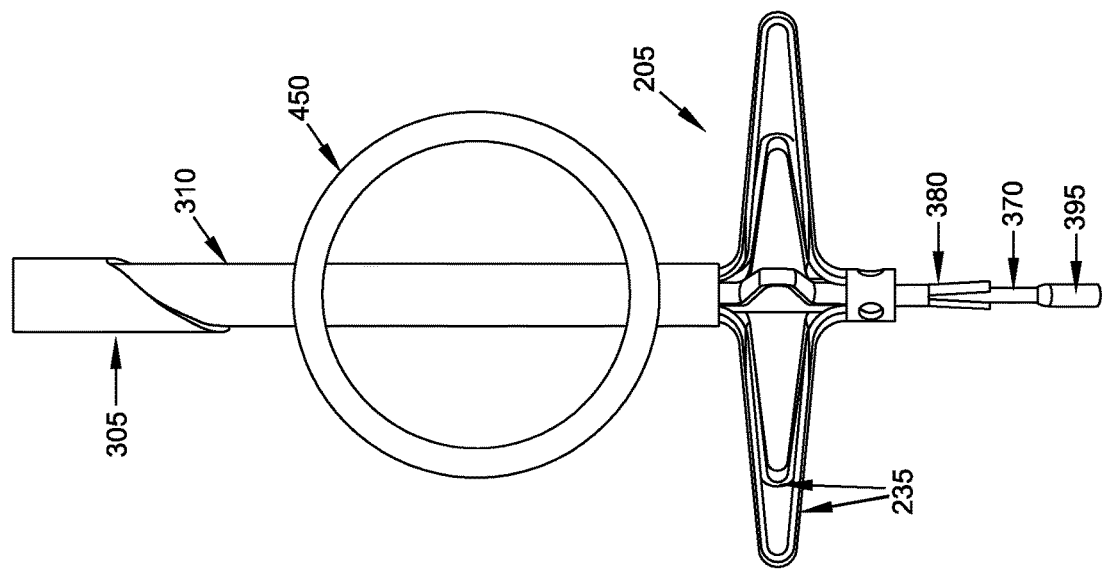

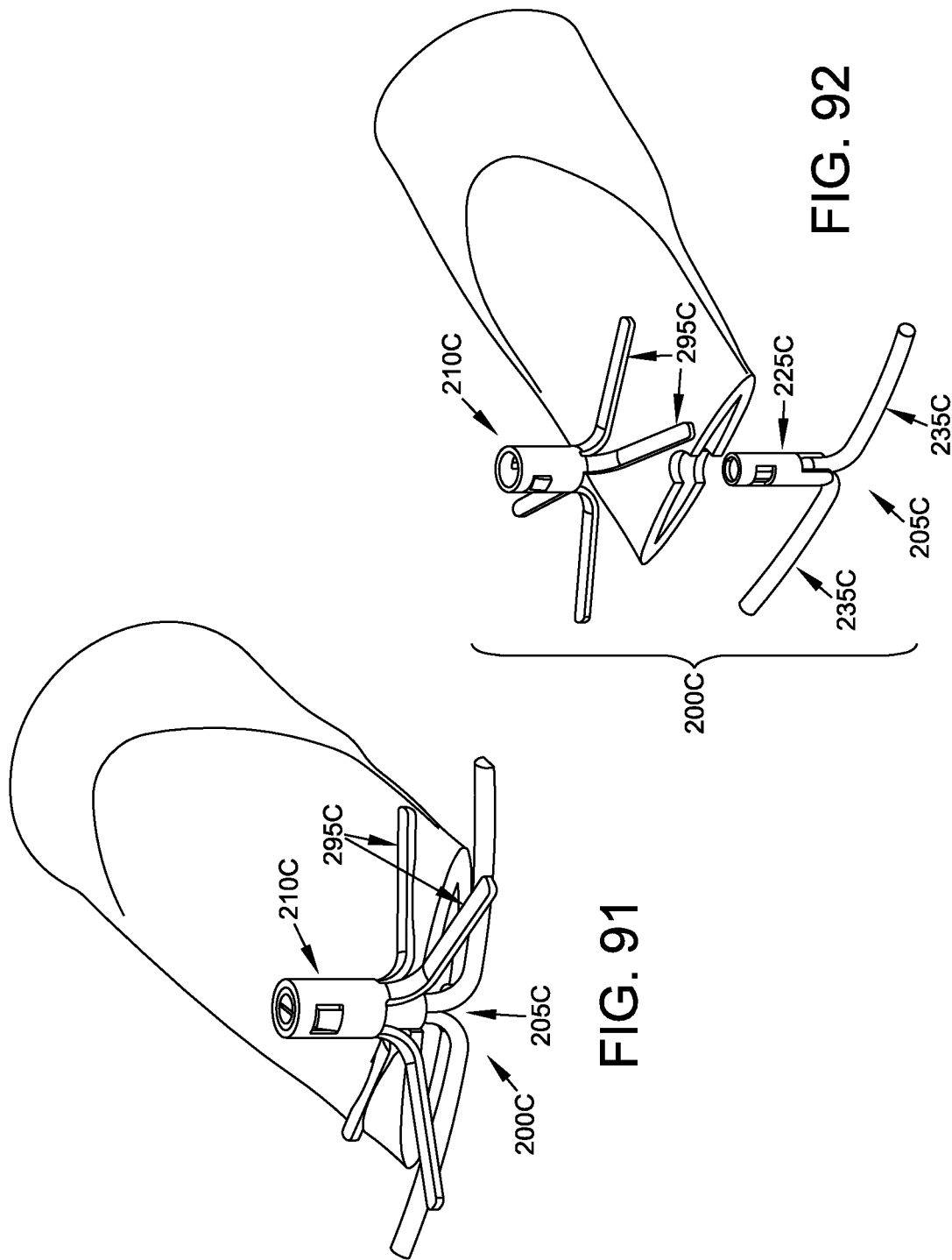

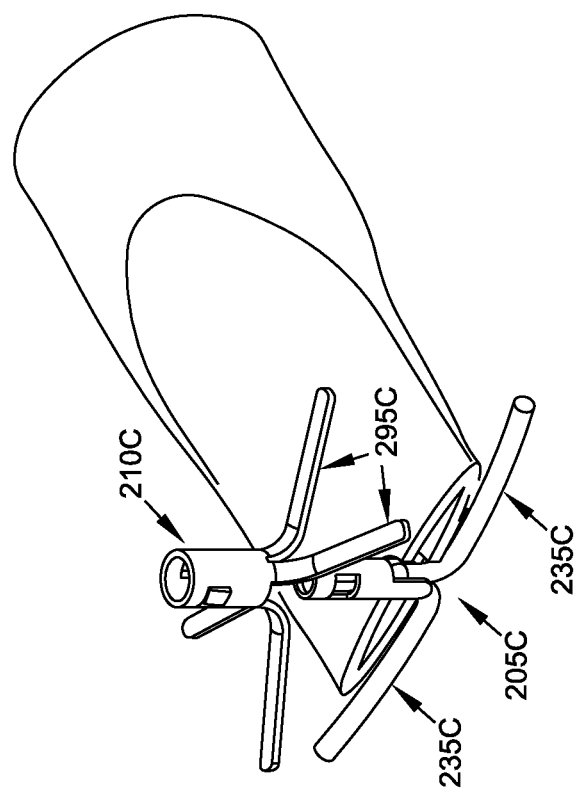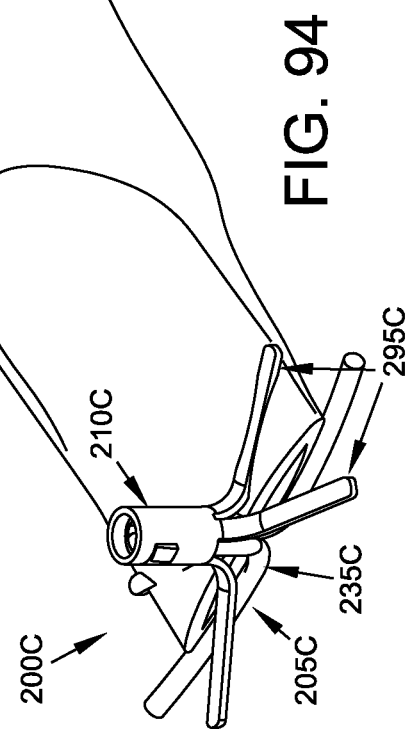

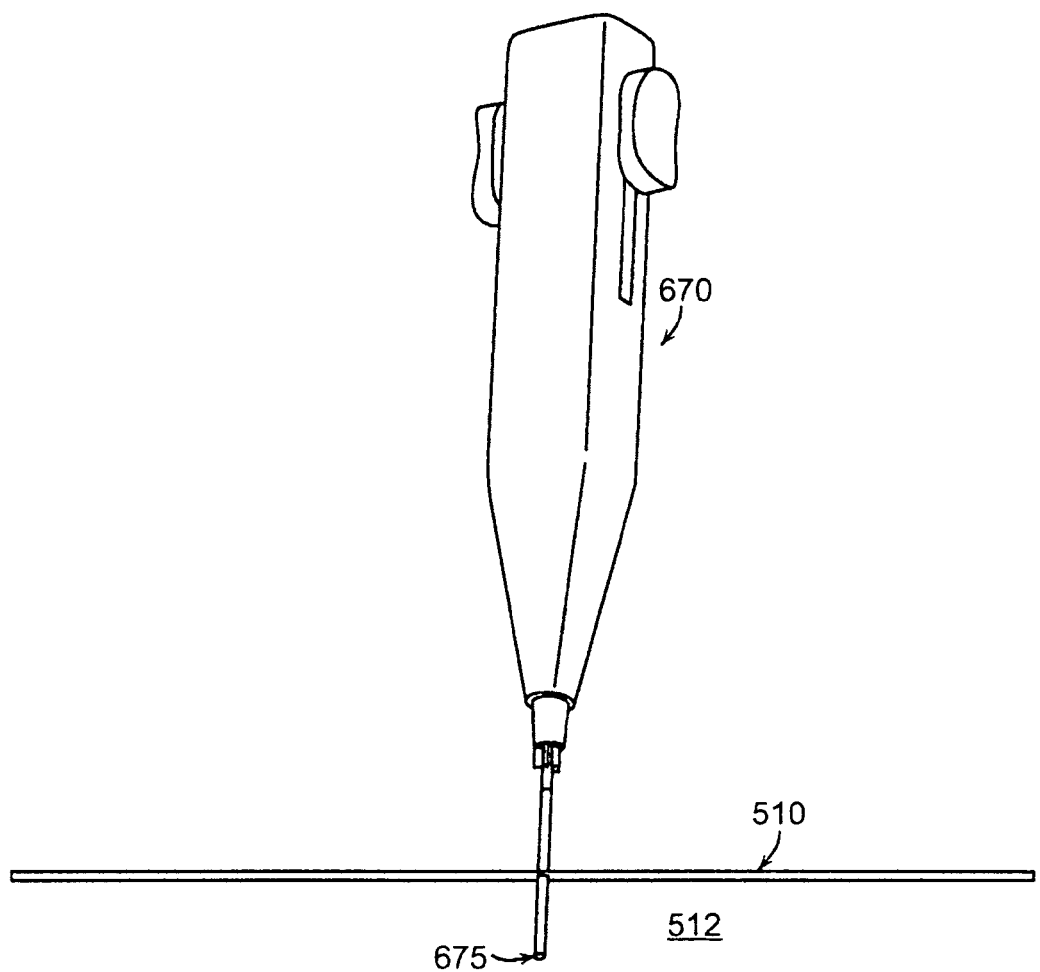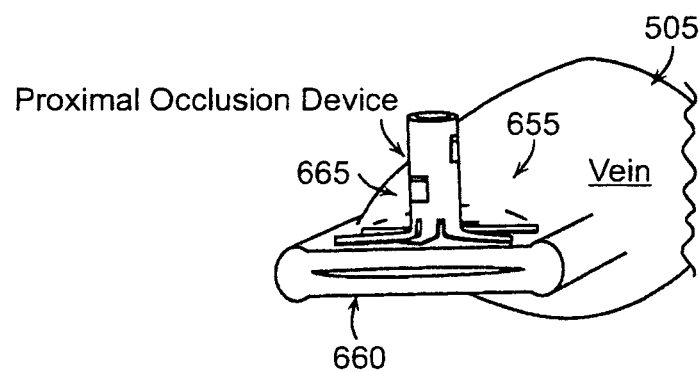
FIG. 127

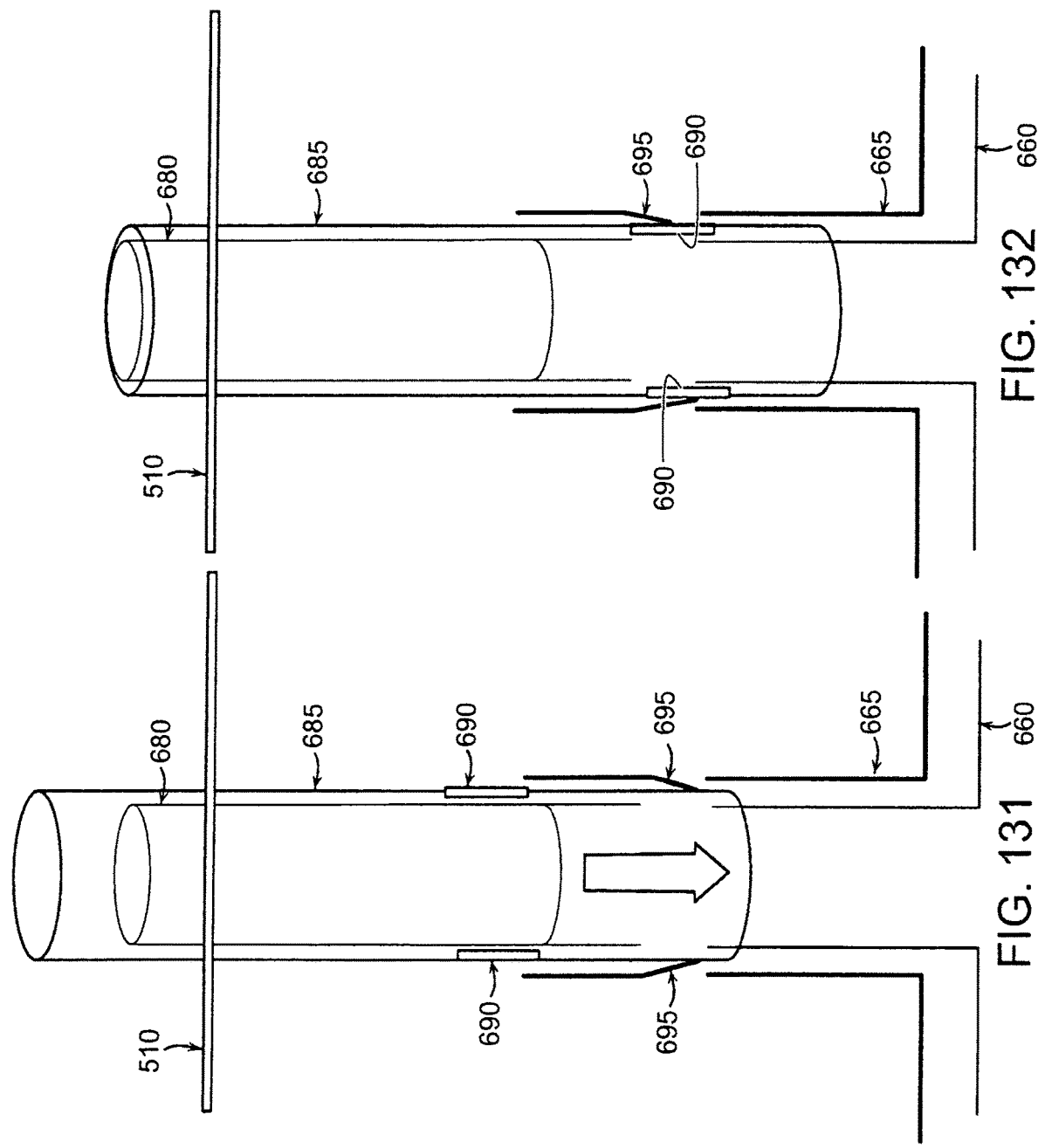

METHOD AND APPARATUS FOR OCCLUDING A BLOOD VESSEL

REFERENCE TO PENDING PRIOR PATENT APPLICATIONS

This application is a continuation of U.S. patent application Ser. No. 13/857,424, filed Apr. 5, 2013, which claims the benefit of and priority to U.S. Provisional Patent Application Ser. No. 61/620,787, filed Apr. 5, 2012, and which is a continuation-in-part of U.S. patent application Ser. No. 13/348,416, filed Jan. 11, 2012, which claims the benefit of and priority to U.S. Provisional Patent Application Ser. No. 61/431,609, filed Jan. 11, 2011, each of which is incorporated by reference herein in its entirety.

FIELD OF THE INVENTION

This invention relates to surgical methods and apparatus in general, and more particularly to surgical methods and apparatus for the occlusion of blood vessels and the treatment of varicose veins. This invention also relates to a minimally invasive means for fastening mechanical structures to tissues or blood vessels, for example, for drug delivery.

BACKGROUND OF THE INVENTION

Varicose Veins in General

There are three sets of veins in the legs:
(i) superficial veins that lie under the skin and may be seen and felt when standing; (ii) deep veins that lie within the muscles and are not seen or felt; and (iii) perforating or connecting veins that join the two systems (i.e., the superficial veins and the deep veins).

Veins lie within all tissues. Veins return blood to the heart. When muscles in the leg contract, blood is pumped back to the heart. Valves inside the veins direct the flow of blood back to the heart.

The veins are relatively weak tubes. Under the skin there is no support for these veins, so that when the pressure in the veins is elevated, areas of weakness occur and the veins enlarge, both in size and length. In some cases the veins can become twisty and bulge significantly. This condition is commonly referred to as varicose veins.

Very small varicose veins are sometimes called spider veins. Unlike the larger varicose veins, these spider veins lie in the skin.

The cause of the increased pressure in the veins is due to the occurrence of "leaky" valves within the veins. The main valve is in the groin region, i.e., in the great saphenous vein near the sapheno-femoral junction. See FIG. 1, which shows a leg 5 of a patient, the femoral vein 10, the great saphenous vein 15, the sapheno-femoral junction 20, and the main valve 25 in the great saphenous vein near the sapheno-femoral junction. Once this main valve in the saphenous vein becomes leaky, the pressure in the vein increases and the veins below the saphenous vein start to enlarge. This causes the next set of valves in the saphenous vein to leak. The raised pressure caused by the leaky valves in the saphenous vein is transmitted to the feeder veins, which distend and their valves also malfunction and become leaky. As this process carries on down the leg, many of the valves in the leg veins become incompetent, with high pressures occurring in the veins, especially on standing.

Initially, the problem is primarily cosmetic. The veins bulge and look unsightly. However, there is commonly also discomfort in the legs upon standing. This discomfort is the result of the veins distending due to the increased pressure.

With time, the high pressure in the veins is transmitted to the surrounding tissues and skin. Small veins within the skin (i.e., spider veins) enlarge and become visible. Blood cells may escape into the tissues and break down, causing areas of discoloration. Because the pressure in the tissues is high, the skin swells and the nutrition of the skin deteriorates. This lowers the local tissue resistance and allows infection to occur. Eventually skin may break down with the development of sores (i.e., ulcers).

Incidence of Varicose Veins

Nearly 40 percent of women and 25 percent of men suffer from lower extremity venous insufficiency and associated visible varicose veins. Primary risk factors include heredity, gender, pregnancy and age. Most of these patients have long-standing leg symptoms which compromise their daily routine, with symptoms worsening during the day while the patients are at work or simply living their lives. Without varicose vein treatment, these symptoms can progress to a lifestyle-limiting condition.

Treatment of Varicose Veins

Treatment of varicose veins is undertaken for relief of the symptoms, i.e., the removal of the unsightly veins and the prevention of the discomfort and late-stage manifestations described above.

1. Non-Surgical Treatment.

The simplest treatment is a non-surgical treatment directed against the high pressure in the varicose veins. More particularly, fitted elastic stockings, strong enough to overcome the increased pressure caused by the "leaky" valves, are used. These fitted elastic stockings control the symptoms and may prevent the veins from further enlargement, however, they are not curative. Good results require consistent, every-day use of the stockings.

2. Surgical/Interventional Treatment.

The aim of the surgical/interventional treatment is (i) the elimination of the cause of the high venous pressure (i.e., the "leaky" valves at the groin); and (ii) the removal of the unsightly veins.

The early approach of "stripping" the saphenous vein (the main vein in the leg) as the sole manner of treatment has now been largely abandoned. This is because the "stripping" approach caused too much trauma and did not remove all of the superficial varicose veins: many of the superficial varicose veins were tributaries of the main superficial vein of the leg (i.e., the saphenous vein) that was stripped, and these tributary veins were not removed by this procedure.

There are currently three basic approaches for treating varicose veins: chemical—sclerorosants and glues; venous ablation using thermal treatments; and open surgery.

A. Sclerotherapy.

Sclerotherapy (the use of sclerosants) is generally used for treating the smaller varicose veins and spider veins that do not appear to be directly associated with "leaky" valves. It is primarily a cosmetic procedure.

In this approach, a sclerosant (i.e., a substance irritating to the tissues) is injected into the smaller varicose veins and spider veins, causing inflammation of the walls of these veins. As a result of this inflammation, the walls of the vein stick together and occlude the lumen of the vein so that no blood can pass through the vein. Eventually these veins shrink and disappear.

The disadvantages of sclerotherapy include:
(i) in the presence of high venous pressure (i.e., with leaky valves and the larger varicose veins), the results are uncertain and the recurrence rate is high; and (ii) the erroneous injection of the sclerosant into the surrounding tissues can result in damage to the surrounding tissues, with areas of discoloration of the skin and even ulceration.

Recently, mixing the sclerosant with air to form a "foam" has been used to destroy the lining of the main vein (i.e., the saphenous vein) of the leg. To date, the results are somewhat unpredictable and there is a danger of the sclerosant escaping through the saphenous vein and into the deep veins and then embolizing into the lungs, which is harmful and dangerous for the patient.

B. Venous Ablation.

Venous ablation for varicose veins can be effected in two ways, i.e. percutaneously and endovenously.

With the percutaneous approach, the superficial smaller varicose veins and spider veins are "heated" and coagulated by shining an external laser light through the skin. However, if the veins are too large, the amount of energy needed to destroy the veins may result in damage to the surrounding tissues. Percutaneous laser treatment is primarily an alternative to the sclerotherapy discussed above, and generally suffers from the same disadvantages described above with respect to sclerotherapy.

With endovenous ablation, a special laser or radio-frequency (RF) catheter is introduced, with local anesthesia, through a needle puncture into the main superficial vein (i.e., the saphenous vein) of the leg. Entry is made in the region around the knee, and the catheter is passed up towards the groin, advancing to the site where the saphenous vein joins the deep veins at the site of the main "leaky" valves. Then, as the catheter is slowly withdrawn back through the vein, the laser light or radio-frequency (RF) energy heats up the wall of the vein, endoluminally coagulating the proteins and destroying the lining surface of the vein. The destruction of the lining surface of the vein causes the vein walls to adhere to one another, thereby eliminating the lumen within the vein and thus preventing the flow of blood. This is a process somewhat similar to sclerotherapy, but no substance is injected into the vein. This procedure takes care of the "leaky" valves and high venous pressures, however, the larger superficial varicose veins in the leg may still need to be removed. This may be done at the same time as the endovenous ablation or at a later time, either by open surgery (phlebectomy) or sclerotherapy. Placement of the laser or radio-frequency (RF) catheter is guided by ultrasound.

The advantages of endovenous laser/radio-frequency (RF) therapy include: (i) it is a minimally invasive procedure and can be done with local anesthesia, either in an operating room or a physician's office; (ii) it does not require hospitalization; (iii) it does not require open surgery with incisions; (iv) recovery is easier than with open surgery, inasmuch as most patients are back at work within a day or two; and (v) some of the prominent varicosities may disappear and may not require a secondary procedure (i.e., either phlebectomy or sclerotherapy).

The disadvantages of endovenous laser/radio-frequency (RF) therapy include: (i) generally, only one leg is done at a time; (ii) the procedure typically requires significant volumes of local anesthetic to be injected into the patient in order to prevent the complications of the heat necessary to destroy the lining of the vein; (iii) if too much heat is applied to the tissue, there can be burning in the overlying skin, with possible disfiguring, including scarring; (iv) prior to the performance of a subsequent phlebectomy procedure, an interval of up to 8 weeks is required in order to evaluate the effectiveness of the venous ablation procedure; and (v) varicosities that remain after this interval procedure still require separate procedures (i.e., phlebectomy or sclerothapy).

C. Open Surgery.

The aim of open surgery is to eliminate the "leaky" valve at the junction of the superficial and deep veins (the cause of the high venous pressure in the leg), as well as the leaky valves in the tributaries of the saphenous vein that may enlarge over the years and result in a recurrence of the varicose veins. This open surgery is directed to removal of some or all of the affected veins.

There is still some controversy as to how much of the saphenous vein needs to be removed for the best results. The current "teaching" is that removing the entire segment of saphenous vein in the thigh reduces the incidence of recurrence. However, the data for this is very weak. Removal of a very short segment of the proximal saphenous vein and the main tributaries at the sapheno-femoral junction is the alternative procedure and, provided that it is combined with removal of all visible varicosities, the results are very similar to removal of the entire thigh segment of the saphenous vein. The advantage of the latter procedure is the increased preservation of the saphenous vein which, in 50-60% or more of varicose vein patients, is not involved in the varicose vein process and is otherwise normal and hence usable for other procedures (such as a bypass graft in the heart or limbs).

The surgery is performed in the operating room under light general or regional (spinal or epidural) anesthesia. An incision (e.g., 1-2 inch) is made in the groin crease and the veins dissected out and the proximal saphenous vein and tributaries excised. The wound is closed with absorbable sutures from within. Once this is completed, small (e.g., 2-4 mm) stab wounds are made over any unsightly varicose veins (these veins are marked out just prior to the surgery with the patient standing) and the varicose veins are completely removed. The small stab wounds associated with removal of the marked-out veins are generally so small that they typically do not require any stitches to close them. When all the previously marked-out veins are removed, the wounds are cleaned and a dressing applied. The leg is wrapped in elastic bandages (e.g., Ace wraps).

In the post-operative care, the dressings and Ace wraps are usually changed in the doctor's office at the first post-operative visit, typically within 24 hours of the open surgical procedure. The patient and a family member or friend is instructed on proper care of the wounds. A simple dressing is applied to cover the small wounds in the legs for the next 2-3 days. After 2-3 days no further treatment is generally required. Recovery is generally rapid, with the patient returning to work within 5-7 days.

The advantages of open surgery include:
(i) varicose veins of both extremities can be done at a single operation, which generally takes 1-2 hours; (ii) the procedure typically does not require hospitalization and is an "out patient" procedure; (iii) the wounds are minimal, with minimal discomfort which is easily managed with oral analgesics (i.e., pain medicine); (iv) the results are generally excellent, with a minimum of recurrence (the results of open surgery remain the "gold standard" against which the sclerotherapy and laser/radio-frequency (RF) venous ablation therapies are compared); (v) recurrent or residual (i.e., those missed at surgery) veins are generally managed with sclerotherapy or phlebectomy under local anesthesia in a doctor's office or in an ambulatory procedure room; and (vi) the saphenous vein, if normal and without varicosities, is preserved and is therefore available for use (e.g., for bypass surgery) in the future if it should be needed.

The disadvantages of open surgery include:
(i) it is an open surgical procedure requiring an anesthetic (either general or regional), with its associated discomfort and with its attendant risks (which may depend on the health or age of the patient); and (ii) recovery generally takes 3-5 days.

Thus it will be seen that varicose veins present a significant problem for many patients which must be addressed, and all of the current procedures for treating varicose veins suffer from a number of significant disadvantages.

SUMMARY OF THE INVENTION

The present invention provides a new and improved approach for treating varicose veins and other blood vessels.

More particularly, the present invention comprises the provision and use of a novel occluder which is used to occlude a vein (e.g., the proximal saphenous vein, the small saphenous vein, tributaries, the perforator veins, etc.) so as to restrict blood flow through the vein and thereby treat varicose veins below the point of occlusion. Significantly, the novel occluder is configured to be deployed using a minimally-invasive approach (i.e., either percutaneously or endoluminally), with visualization being provided by ultrasound and/or other visualization apparatus (e.g., CT, MRI, X-ray etc.). As a result, the novel treatment can be provided in a doctor's office, with minimal local anesthetic, and effectively no post-operative care.

In one form of the invention, there is provided apparatus for occluding a blood vessel, the apparatus comprising:
an occluder, the occluder being configured so that at least a portion of the occluder may assume (i) a diametrically-reduced configuration for disposition within the lumen of a tube, and (ii) a diametrically-expanded configuration for disposition adjacent to the blood vessel, such that when said at least a portion of the occluder is in its diametrically-expanded configuration adjacent to the blood vessel, the occluder will cause occlusion of the blood vessel.

In another form of the invention, there is provided a method for occluding a blood vessel, the method comprising:
providing apparatus comprising:
an occluder, the occluder being configured so that at least a portion of the occluder may assume (i) a diametrically-reduced configuration for disposition within the lumen of a tube, and (ii) a diametrically-expanded configuration adjacent to the blood vessel, such that when said at least a portion of the occluder is in its diametrically-expanded configuration adjacent to the blood vessel, the occluder will cause occlusion of the blood vessel; and
positioning the occluder adjacent to the blood vessel so as to cause occlusion of the blood vessel.

In another form of the invention, there is provided apparatus for delivering a substance to a location adjacent to a blood vessel, the apparatus comprising:
a carrier, the carrier being configured so that at least a portion of the carrier may assume (i) a diametrically-reduced configuration for disposition within the lumen of a tube, and (ii) a diametrically-expanded configuration for disposition adjacent to the blood vessel, such that when the substance is attached to the carrier and said at least a portion of the carrier is in its diametrically-expanded configuration adjacent to the blood vessel, the substance will be disposed adjacent to the blood vessel.

In another form of the invention, there is provided a method for delivering a substance to a location adjacent to a blood vessel, the method comprising:
providing apparatus comprising:
a carrier, the carrier being configured so that at least a portion of the carrier may assume (i) a diametrically-reduced configuration for disposition within the lumen of a tube, and (ii) a diametrically-expanded configuration for disposition adjacent to the blood vessel, such that when the substance is attached to the carrier and said at least a portion of the carrier is in its diametrically-expanded configuration adjacent to the blood vessel, the substance will be disposed adjacent to the blood vessel; and
positioning the carrier adjacent to the blood vessel so that the substance is disposed adjacent to the blood vessel.

In another form of the invention, there is provided apparatus for percutaneously occluding a hollow structure, said apparatus comprising:
an occluder, said occluder comprising a first component and a second component, wherein said first component is configured so that it may assume (i) a diametrically-reduced configuration for disposition within the lumen of a hollow tube, and (ii) a diametrically-expanded configuration for disposition adjacent to the hollow structure, whereby to occlude the hollow structure, and further wherein said second component percutaneously connects said first component to a site remote from said first component.

In another form of the invention, there is provided a method for percutaneously occluding a hollow structure, the method comprising:
providing apparatus comprising:
an occluder, said occluder comprising a first component and a second component, wherein said first component is configured so that it may assume (i) a diametrically-reduced configuration for disposition within the lumen of a hollow tube, and (ii) a diametrically-expanded configuration for disposition adjacent to the hollow structure, whereby to occlude the hollow structure, and further wherein said second component percutaneously connects said first component to a site remote from said first component; and
positioning said occluder adjacent to the hollow structure so as to occlude the hollow structure.

In another form of the invention, there is provided an occluder for occluding a hollow structure, wherein the occluder is configured to be percutaneously delivered to an internal site and thereafter expanded so as to cause complete or partial occlusion of the hollow structure, and further wherein the occluder is configured so that the expansion of the occluder may thereafter be reversed in full or in part so as to completely or partially restore the hollow structure to its original condition.

In another form of the invention, there is provided a method for occluding a hollow structure, wherein an occluder is percutaneously delivered to an internal site and thereafter expanded so as to cause complete or partial occlusion of the hollow structure, and further wherein the occluder is configured so that the expansion of the occluder may thereafter be reversed in full or in part so as to completely or partially restore the hollow structure to its original condition.

In another form of the invention, there is provided apparatus for occluding a hollow structure, wherein the apparatus comprises an occluder, a device for percutaneously delivering the occluder to an internal site and deploying the occluder so that it completely or partially occludes the hollow structure, and a device for removing some or all of the occluder so as to completely or partially restore the hollow structure to its original condition.

In another form of the invention, there is provided a method for treating a patient, wherein the method comprises percutaneously delivering an occluder to an internal site so that it completely or partially occludes the hollow structure, and further wherein the method comprises thereafter removing some or all of the occluder so as to completely or partially restore the hollow structure to its original condition.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 2-4 are schematic views showing an occluder occluding a blood vessel in accordance with one form of the present invention;

FIGS. 6 and 7 are schematic views showing an exemplary syringe-type inserter which may be used to deploy the occluder shown in FIGS. 2-4;

FIGS. 8-10 are schematic views showing an occluder occluding a blood vessel in accordance with another form of the present invention;

FIGS. 18-20 are schematic views showing the occluders of the types shown in FIGS. 15-17 occluding a blood vessel in accordance with yet another form of the present invention;

FIGS. 21-24 are schematic views showing an occluder occluding a blood vessel in accordance with another form of the present invention;

FIGS. 25-27 are schematic views showing an occluder occluding a blood vessel in accordance with still another form of the present invention;

FIGS. 34 and 35 are schematic views showing a drug/cellular delivery body being attached to a blood vessel in accordance with one form of the present invention;

FIGS. 36 and 37 are schematic views showing a drug/cellular delivery body being attached to a blood vessel in accordance with another form of the present invention;

FIGS. 38 and 39 are schematic views showing a drug/cellular delivery body being attached to a blood vessel in accordance with still another form of the present invention;

FIGS. 40 and 41 are schematic views showing a drug/cellular delivery body being attached to a blood vessel in accordance with yet another form of the present invention;

FIGS. 42-48 are schematic views showing a two-part occluder formed in accordance with another form of the present invention;

FIGS. 59-82 are schematic views showing the two-part occluder of FIGS. 42-48 being deployed across a blood vessel using the installation apparatus of FIGS. 49-58;

FIGS. 91-94 are schematic views showing yet another two-part occluder formed in accordance with the present invention;

FIGS. 127-142 are schematic views showing another temporary occluder formed in accordance with the present invention;

DETAILED DESCRIPTION OF THE PREFERRED EMBODIMENTS

The present invention provides a new and improved approach for treating varicose veins and other blood vessels.

More particularly, the present invention comprises the provision and use of a novel occluder which is used to occlude a vein (e.g., the proximal saphenous vein, the small saphenous vein, tributaries, the perforator veins, etc.) so as to restrict blood flow through the vein and thereby treat varicose veins below the point of occlusion. Significantly, the novel occluder is configured to be deployed using a minimally-invasive approach (i.e., either percutaneously or endoluminally), with visualization being provided by ultrasound and/or other visualization apparatus (e.g., CT, MRI, X-ray etc.). As a result, the novel treatment can be provided in a doctor's office, with minimal local anesthetic, and effectively no post-operative care.

Percutaneous Approach

In the percutaneous approach, the occluder is delivered by percutaneously advancing the occluder through the skin, through intervening tissue and then across some or all of the blood vessel (e.g., the great saphenous vein near the sapheno-femoral junction) so as to occlude the blood vessel. This occlusion (or multiple of these occlusions) will thereby treat varicose veins. In one form of the invention, the occluder is configured to occlude the vein by compressing the vein and closing down its lumen; and in another form of the invention, the occluder is configured to occlude the vein by depositing a mass within the lumen of the vein so as restrict blood flow through the lumen of the vein. The occlusion of the lumen may be complete or partial. If the occlusion is partial, some blood may continue to flow in the vein. Such partial occlusion can act to relieve some of the pressure on the valve, thereby improving its function. In some applications, an occlusion of 70% or greater of the lumen may be desired and realized based on the current invention. In other applications, an occlusion of 80% or greater of the lumen may be desired and realized based on the current invention. In one embodiment, the occlusion pressure applied may be greater than 40 mm of mercury. In another embodiment of the present invention, the occlusion pressure may be greater than the pressure of the typical blood flow in the vein.

Figure 4:
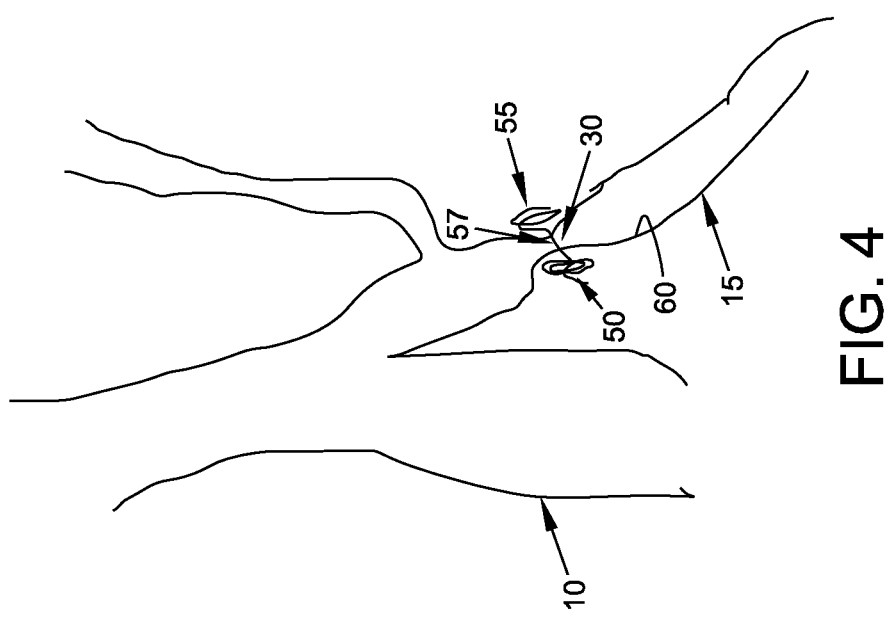
Figure 11:
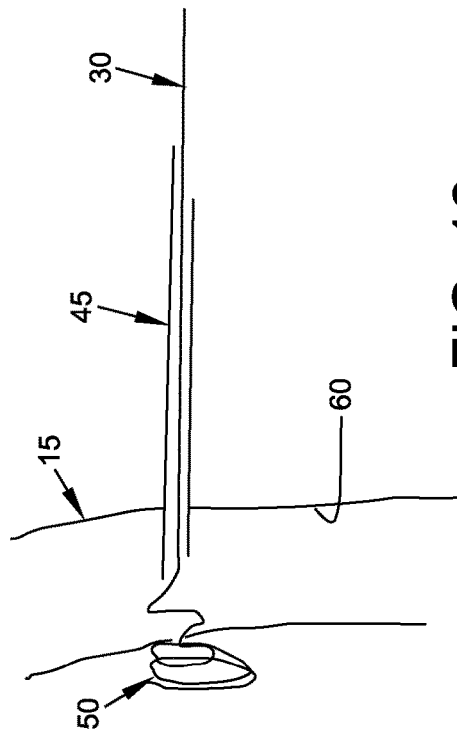
FIGS. 11-14 are schematic views showing an occluder occluding a blood vessel in accordance with still another form of the present invention.
Figure 12:
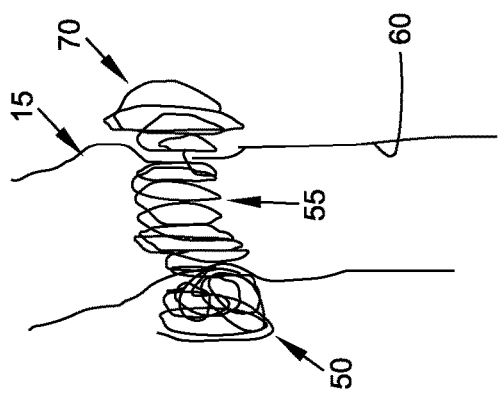
Figure 13:
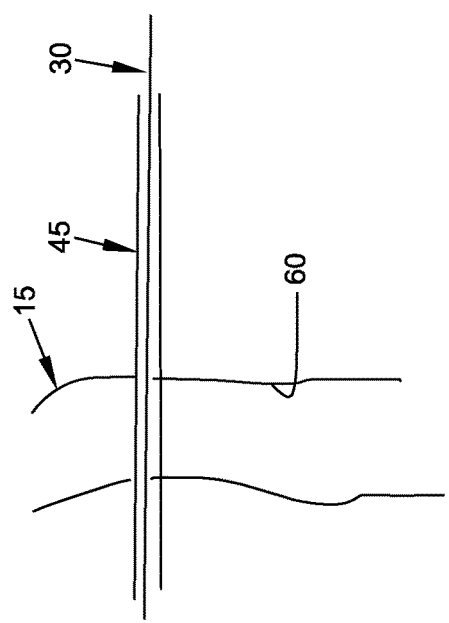

Looking first at FIGS. 2-4, in one form of the invention, there is provided an occluder 30. Occluder 30 comprises an elastic filament 35 which, in an unconstrained condition, comprises a generally non-linear configuration (e.g., a coiled mass) but which, when properly restrained, can maintain a linear configuration (e.g., in the narrow lumen 40 of a needle 45, or where the filament is formed out of a shape memory material, by appropriately controlling its temperature and hence its shape); when the restraint is removed (e.g., the elastic filament 35 is extruded from the constraining lumen 40 of the needle 45, or the temperature of the shape memory material is elevated such as by body heat), elastic filament 35 will return to its generally non-linear configuration, whereby to provide enlarged masses for occluding the vein.

In one form of the invention, the occluder is formed out of a shape memory material (e.g., a shape memory alloy such as Nitinol, or a shape memory polymer), with the shape memory material being configured to provide superelasticity, or temperature-induced shape changes, or both).

In one preferred method of use, the occluder 30 is installed in the narrow lumen 40 of a needle 45 (FIG. 2), the needle is introduced percutaneously and advanced across the vein which is to be occluded (e.g., the great saphenous vein 15), a first length of the occluder is extruded from the needle on the far side of the vein so that a portion of the occluder is restored to a coiled mass configuration 50 on the far side of the vein (FIG. 3), the needle is withdrawn back across the vein, and then the remainder of the occluder is extruded on the near side of the vein (FIG. 4), whereupon the remainder of the occluder is restored to a coiled mass configuration 55, with a portion 57 of the occluder extending across the lumen 60 of the vein 15, and with the portions of the occluder on the far and near sides of the vein (i.e., the coiled masses 50 and 55, respectively) being drawn toward one another under the coiling force inherent in the elastic filament so as to compress the vein there between and occlude its lumen 60, whereby to restrict blood flow through the vein and thereby treat the varicose veins.

As noted above, occluder 30 may be formed out of a shape memory material (e.g., a shape memory alloy such as Nitinol, or a shape memory polymer, etc.), with the shape memory material being configured to provide superelasticity, or temperature-induced shape changes, or both).

Figure 1:
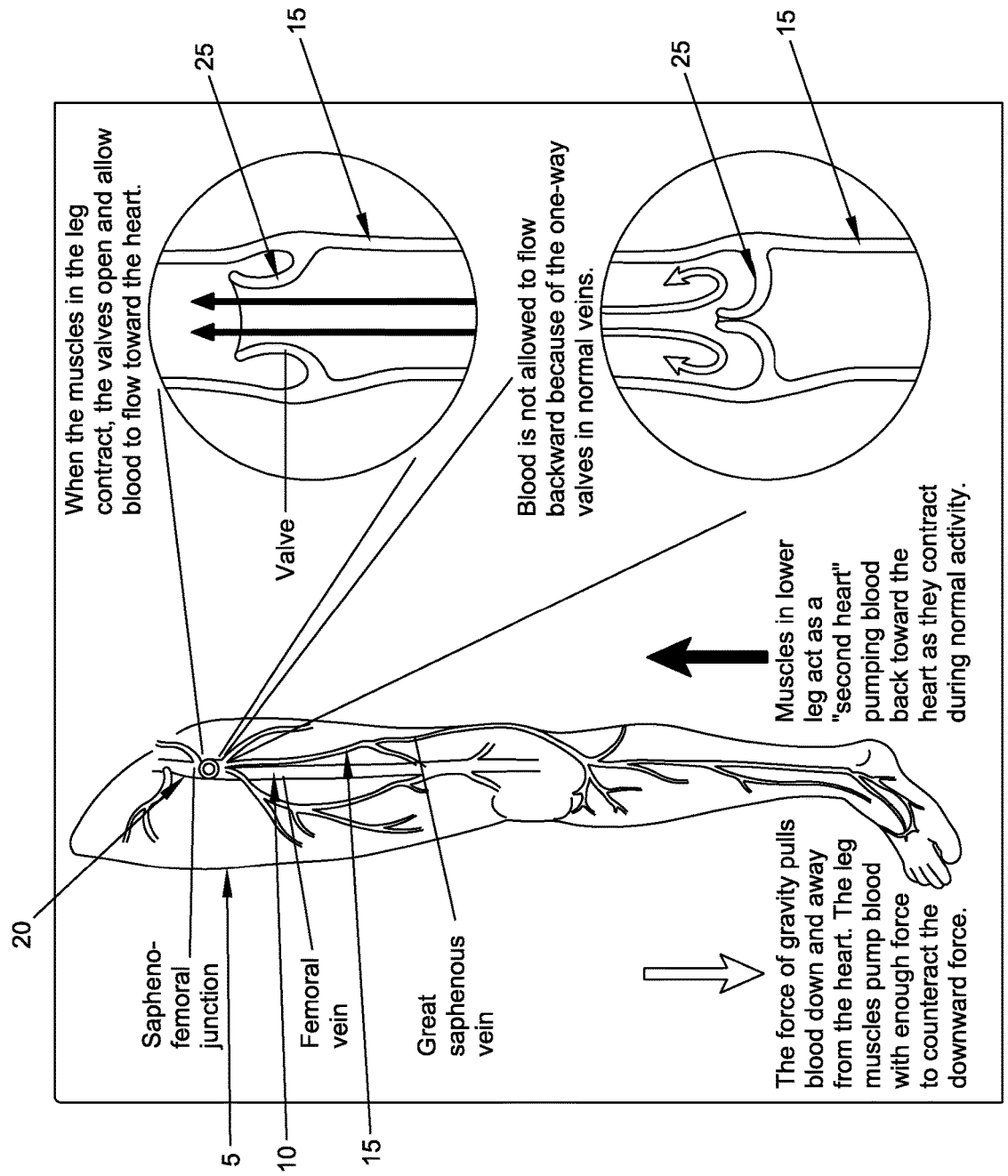
FIG. 1 is a schematic view showing various aspects of the venous system of the leg.
Figure 5:
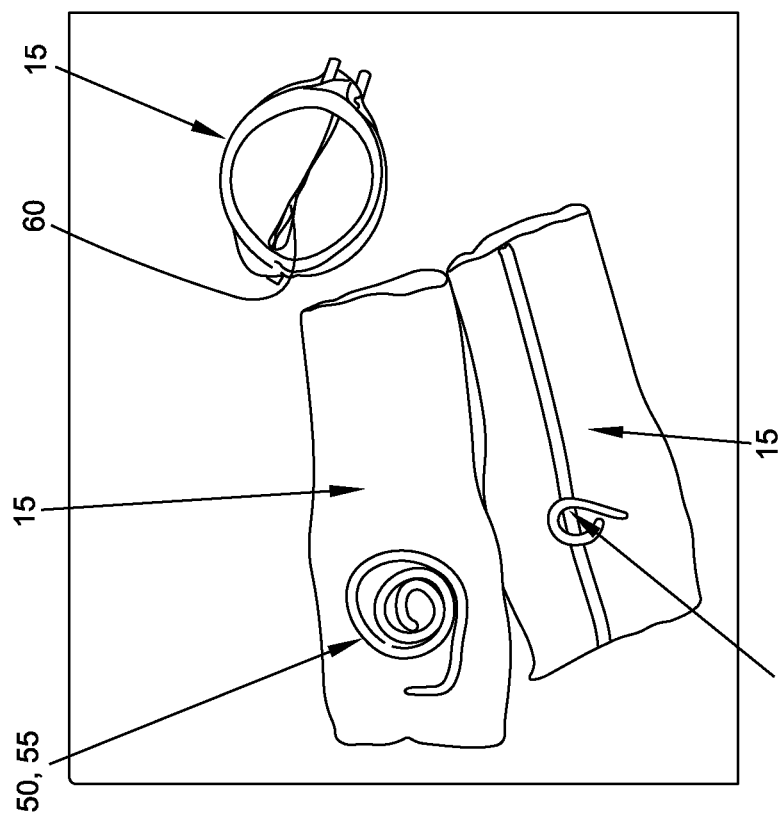
FIG. 5 is a schematic view showing one possible construction for the occluder shown in FIGS. 2-4.

In the form of the invention shown in FIGS. 2-4, occluder 30 is formed out of a single elastic filament 35, and a shape transition (i.e., from substantially linear to a pair of opposing coiled masses 50, 55) is used to cause occlusion of the target blood vessel. In this respect it should be appreciated that the aforementioned coiled masses 50, 55 may comprise substantially random turns of the elastic filament arranged in a substantially three-dimensional structure (i.e., somewhat analogous to a ball of string), or the coiled masses 50, 55 may comprise highly reproducible structures such as loops, coils, etc., and these loops, coils, etc. may or may not assume a substantially planar structure. See, for example, FIG. 5, where coiled masses 50, 55 comprise highly reproducible loops and coils.

FIGS. 6 and 7 show an exemplary syringe-type inserter 65 which may be used to deploy the novel occluder of the present invention. The syringe-type inserter 65 may contain one occluder 30 or multiple pre-loaded occluders 30, e.g., where syringe-type inserter 65 comprises multiple occluders 30, the occluders may be disposed serially within the syringe-type inserter, or they may be disposed parallel to one another within the syringe-type inserter (i.e., in the manner of a "Gatling gun" disposition), etc. When the syringe-type inserter 65 is activated, an occluder 30 is deployed out of the distal end of needle 45.

In FIGS. 2-4, occluder 30 is shown occluding the vein by compressing the vein between the two coiled masses 50, 55, whereby to close down its lumen 60. However, in another form of the invention, the occluder 30 can be used to occlude the vein without compressing the vein. This is done by depositing a coiled mass within the lumen of the vein, whereby to restrict blood flow through the lumen of the vein. More particularly, and looking now at FIGS. 8-10, in this form of the invention, the needle 45 is passed into the interior of the vein 15 and one coiled mass 50 of the occluder 30 is extruded into the lumen 60 of the vein (FIG. 8) so as to occlude the lumen of the vein, the needle 45 is withdrawn to the near side of the vein (FIG. 9), and then another coiled mass 55 is disposed on the near side of the vein (FIG. 10), with the portion 57 of the occluder extending through the side wall of the vein so as to stabilize the occluder relative to the vein (i.e., so as to attach the occluder to the vein and prevent the occluder from moving relative to the vein).

Figure 14:
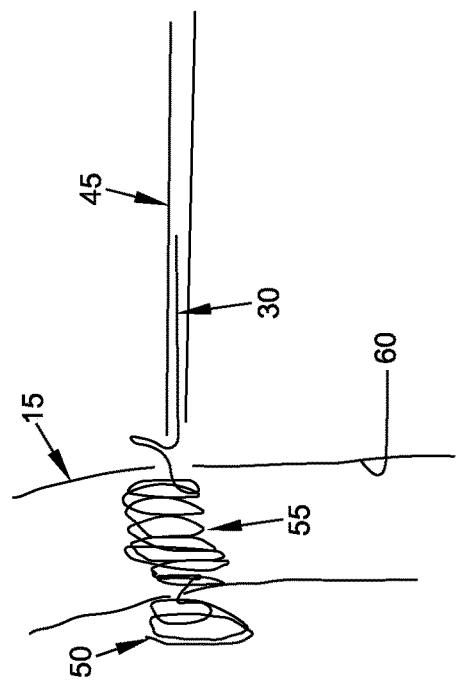

FIGS. 11-14 show another approach where a coiled mass of the occluder 30 is deposited within the interior of the blood vessel so as to obstruct blood flow through the vessel. More particularly, in this form of the invention, the needle 45 is passed completely through the vein (FIG. 11), a coiled mass 50 of the occluder is deposited on the far side of the vein (FIG. 12), the needle is withdrawn into the interior of the vein where another coiled mass 55 of the occluder is deposited (FIG. 13), and then the needle is withdrawn to the near side of the vein where another coiled mass 70 of the occluder 30 is deposited (FIG. 14). In this form of the invention, coiled mass 55 resides within the lumen 60 of the vein and obstructs blood flow while coiled masses 50 and 70 compress the vein inwardly and stabilize the disposition of the intraluminal coiled mass 55.

Figure 15:
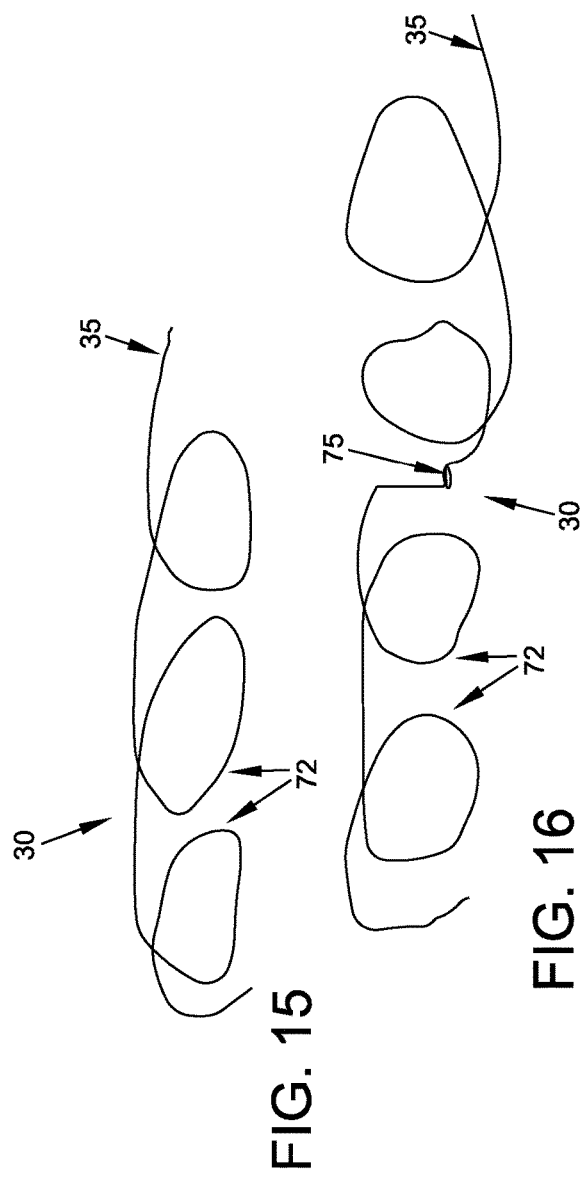
FIGS. 15-17 are schematic views showing other possible constructions for the occluder of the present invention.
Figure 16:
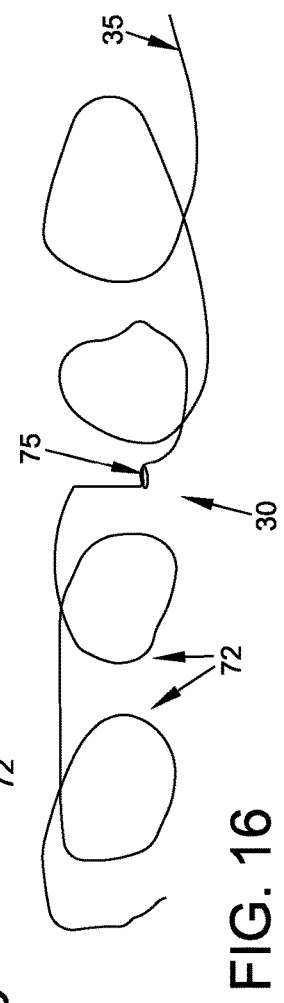

FIGS. 15 and 16 show occluders 30 formed out of a single strand of elastic filament. In FIG. 15, the occluder 30 comprises a relatively ordered coil where the turns 72 of the coil are unidirectional. In FIG. 16, the occluder 30 comprises another relatively ordered coil but where the turns rotate in opposite directions on different sides of a midpoint 75. Of course, it should also be appreciated that the occluder 30 can be constructed so as to form a relatively disordered coil, i.e., where the strand of the filament follows a relatively random pattern (see, for example, the disordered coils illustrated in FIGS. 8-10). Indeed, where it is desired that the mass of the reformed coil itself provide a flow obstruction (e.g., where the reformed coil is disposed intraluminally so as to impede blood flow through the vein), it is generally preferred that the elastic filament reform into a relatively disordered coil having a relatively random disposition, since this can provide a denser filament configuration.

Figure 17:
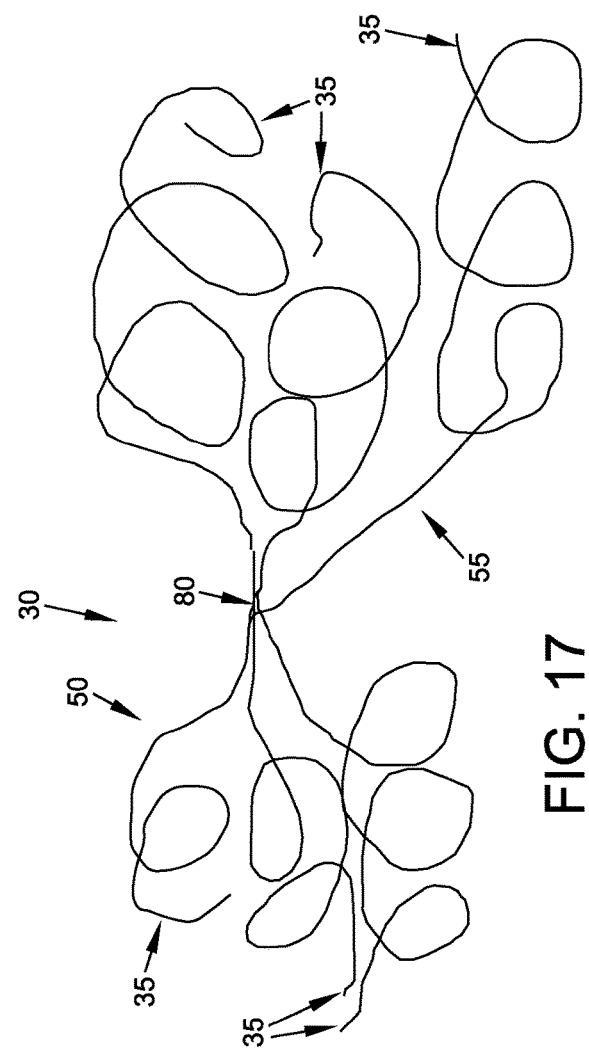

FIG. 17 shows an occluder 30 formed out of multiple strands of elastic filaments 35. In one form of the invention, these multiple strands are joined together at a joinder 80. Again, the coils (e.g., the aforementioned coiled masses 50, 55, 70) formed by these multiple strands can be relatively ordered or relatively disordered. FIGS. 18 and 19 show how the multistrand occluder of FIG. 17 can be used to occlude a vein by forming coiled masses 50, 55 to compress the side wall of the vein inwardly so as to restrict blood flow through the vein. FIG. 20 shows how the multistrand occluder 30 of FIG. 17 can be used to occlude a vein by depositing a coiled mass 55 within the lumen 60 of the vein, whereby to restrict blood flow through the lumen of the vein. In FIG. 20, a number of the elastic filaments 35 are shown piercing the side wall of the vein so as to hold the coiled mass 55 in position within the lumen of the blood vessel.

FIGS. 21-24 show another form of occluder 30 where the occluder is formed by structures other than a filament. By way of example but not limitation, the occluder 30 may comprise a transluminal section 85, a far side lateral projection 90 and a near side lateral projection 95, with the far side lateral projection 90 and the near side lateral projection 95 being held in opposition to one another so as to close down the lumen 60 of the vein 15. Such an arrangement may be provided by many different types of structures, e.g., such as the "double T-bar" structure shown in FIGS. 25-27 where the transluminal section 85 of the occluder 30 is formed out of an elastic material which draws the two opposing T-bars 90, 95 of the occluder together so as to provide vessel occlusion. Still other arrangements for connecting and drawing together a far side lateral projection 90 and a near side lateral projection 95 will be apparent to those skilled in the art in view of the present disclosure. By way of further example but not limitation, far side lateral projection 90 and near side lateral projection 95 may be connected together by a loop of suture, with the loop of suture being lockable in a reduced size configuration (i.e., so as to maintain occlusion) with a sliding locking knot.

Furthermore, multiple occluders 30 may be used on a single blood vessel or tissue to occlude the blood vessel more completely, or to occlude a blood vessel in multiple regions, or to attach a material (e.g., a drug or cellular delivery element) in multiple places to the blood vessel. The occluders may be coated with a drug-eluting compound, or the occluders may be electrically charged to enhance or prevent clotting or to deliver a desired compound or agent to the blood vessel, etc. If desired, the location of the occluding or attachment element may be precisely controlled to deliver the desired compound or agent at a specific anatomical location.

Endoluminal Approach

In the endoluminal approach, the occluder 30 is delivered to the occlusion site by endoluminally advancing the occluder up the vein using a catheter, and then deploying the occluder in the vein, with the occluder acting to occlude the vein and thereby treat varicose veins. In this form of the invention, the occluder is preferably passed through one or more side walls of the vein so as to stabilize the occluder relative to the vein. In one form of the invention, the occluder is configured to occlude the vein by depositing a mass within the lumen of the vein so as to restrict blood flow through the lumen of the vein; and in another form of the invention, the occluder is configured to occlude the vein by compressing the vein and closing down its lumen.

Figure 28:
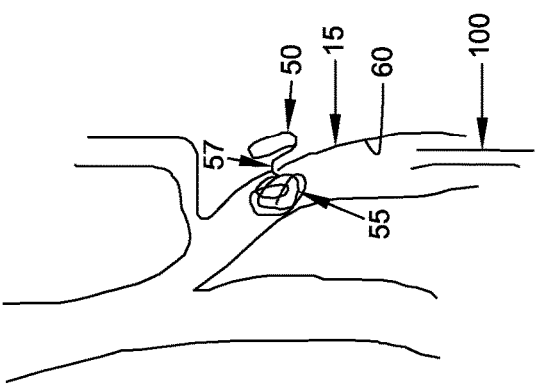
FIGS. 28 and 29 are schematic views showing an occluder occluding a blood vessel in accordance with yet another form of the present invention.
Figure 29:
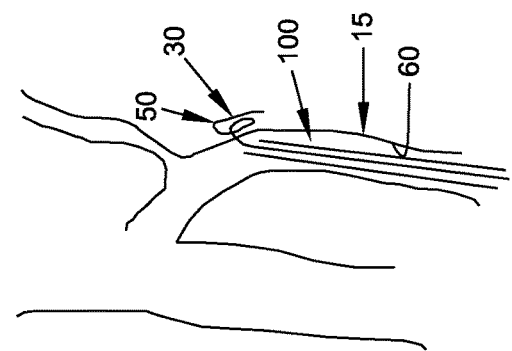

More particularly, and looking now at FIGS. 28 and 29, a catheter 100 is used to endoluminally advance the occluder 30 up the interior of the vein 15 to a deployment site. Then one end of the occluder is passed through the side wall of the vein so as to deposit a coiled mass 50 of the occluder 30 outside the vein, and the remainder of the occluder is deposited as a coiled mass 55 within the lumen 60 of the vein, with a portion 57 of the occluder extending through the side wall of the vein so as to attach the occluder to the side wall of the vein and thereby stabilize the occluder relative to the vein. Thus, in this form of the invention, a coiled mass 55 of the occluder is deposited within the interior of the vein so as to restrict blood flow through the vein and thereby treat varicose veins.

Figure 30:
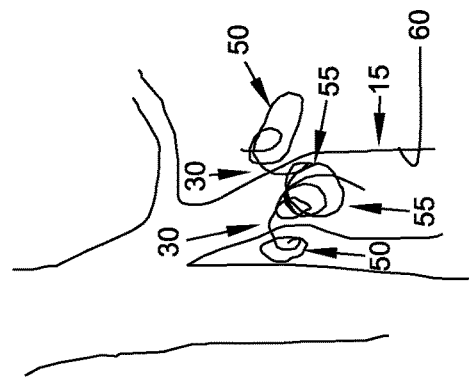
FIGS. 30 and 31 are schematic views showing an occluder occluding a blood vessel in accordance with another form of the present invention.
Figure 31:
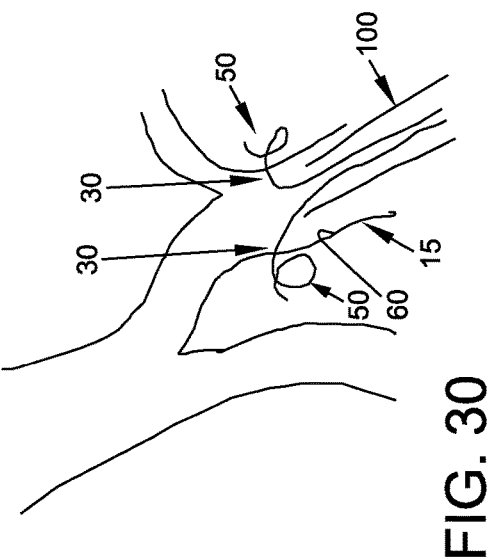

FIGS. 30 and 31 show how two separate occluders 30, each used in the manner shown in FIGS. 28 and 29, can be used to increase the coiled mass of occluder contained within the lumen of the vein, whereby to increase the extent of occlusion of the lumen of the vein.

Figure 33:
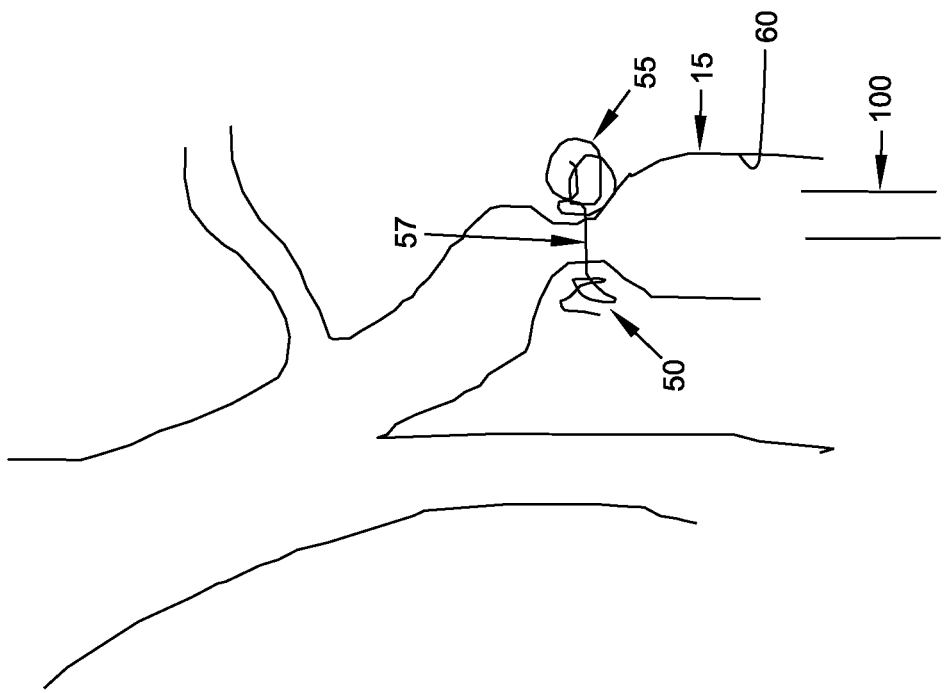
FIGS. 32 and 33 are schematic views showing an occluder occluding a blood vessel in accordance with still another form of the present invention.
Figure 32:
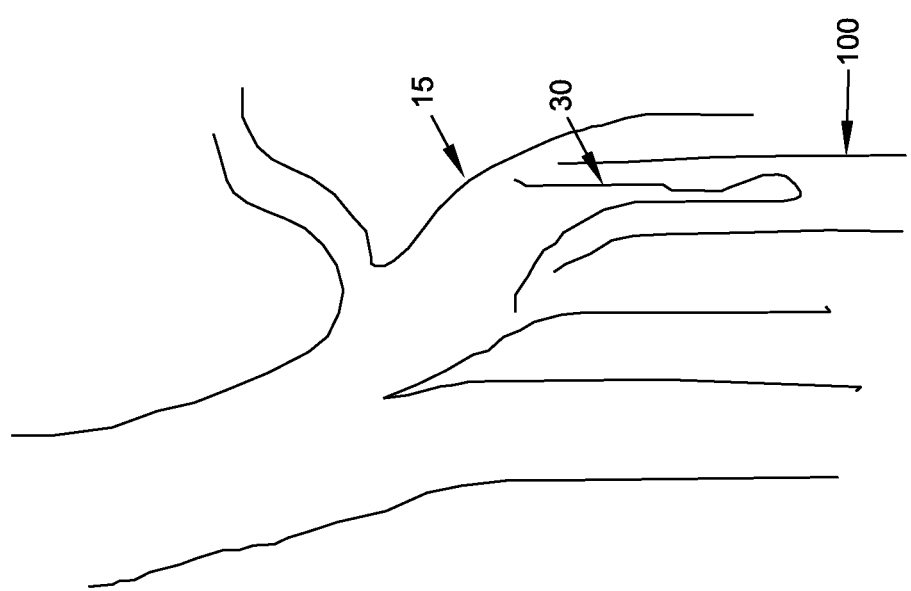

FIGS. 32 and 33 show how an occluder 30 can be delivered endoluminally and used to compress the outer walls of the vein so as to occlude blood flow through the lumen of the vein. More particularly, in this form of the invention, the occluder 30 is advanced endoluminally through the vein to the deployment site, one end of the occluder is passed through one side wall of the vein so as to deposit a coiled mass 50 on one side of the vein and the other end of the occluder is passed through the other side wall of the vein so as to deposit another coiled mass 55 on the other side of the vein, with the two coiled masses being connected together by the intermediate portion 57 of the occluder and with the two coiled masses being drawn toward one another under the coiling force inherent in the elastic filament so as to apply compressive opposing forces on the two sides of the vein, whereby to compress the vein and close down its lumen.

Occlusion in Combination with Phlebectomy

If desired, the novel occluder of the present invention can be used in conjunction with the removal of the large varicose veins (i.e., phlebectomy). The phlebectomy can be done at the same time as the occlusion of the vein or at another time. For this surgical procedure, minimal local anesthetic is needed.

Occluding Tubular Structures for Purposes Other than Treating Varicose Veins

It will be appreciated that the novel occluder of the present invention can also be used to occlude tubular structures for purposes other than treating varicose veins. By way of example but not limitation, the novel occluder of the present invention can be used to occlude other vascular structures (e.g., to occlude arteries so as to control bleeding), or to occlude other tubular structures within the body (e.g., phallopian tubes, so as to induce infertility), etc.

Drug/Cellular Delivery Applications

Furthermore, using the foregoing concept of minimally-invasive hollow tube penetration, and attachment and fixation of the device to the vessel wall, either percutaneously or endoluminally, the occluder 30 may be modified so as to allow drug/cellular delivery at fixed points within or adjacent to the vasculature or other hollow bodily structure. In this form of the invention, the device functions as a drug/cellular delivery stabilizer, and may or may not function as an occluder. See, for example, FIGS. 34 and 35, where an elastic filament 35, having a drug/cellular delivery body 105 attached thereto, is advanced across a blood vessel 110 using a needle 115, with the distal end of the elastic filament forming a coiled mass 120 on the far side of the blood vessel and the drug/cellular delivery body 105 being securely disposed within the lumen 125 of the blood vessel. FIGS. 36 and 37 show a similar arrangement where a catheter 130 is used to deliver the device endoluminally. FIGS. 38 and 39 show another arrangement wherein the device is delivered percutaneously so that the coiled mass is disposed inside lumen 125 of the blood vessel and the drug/cellular delivery body 105 is disposed outside the blood vessel, and FIGS. 40 and 41 show how the device is delivered endoluminally so that the coiled mass is disposed inside lumen 125 of the blood vessel and the drug/cellular delivery body 105 is disposed outside the blood vessel. These drug/cellular delivery devices may be passive or active polymers or silicon-based or micro- and nanotechnology devices, or matrices of materials, etc.

Two-Part Occluder

Figure 42:
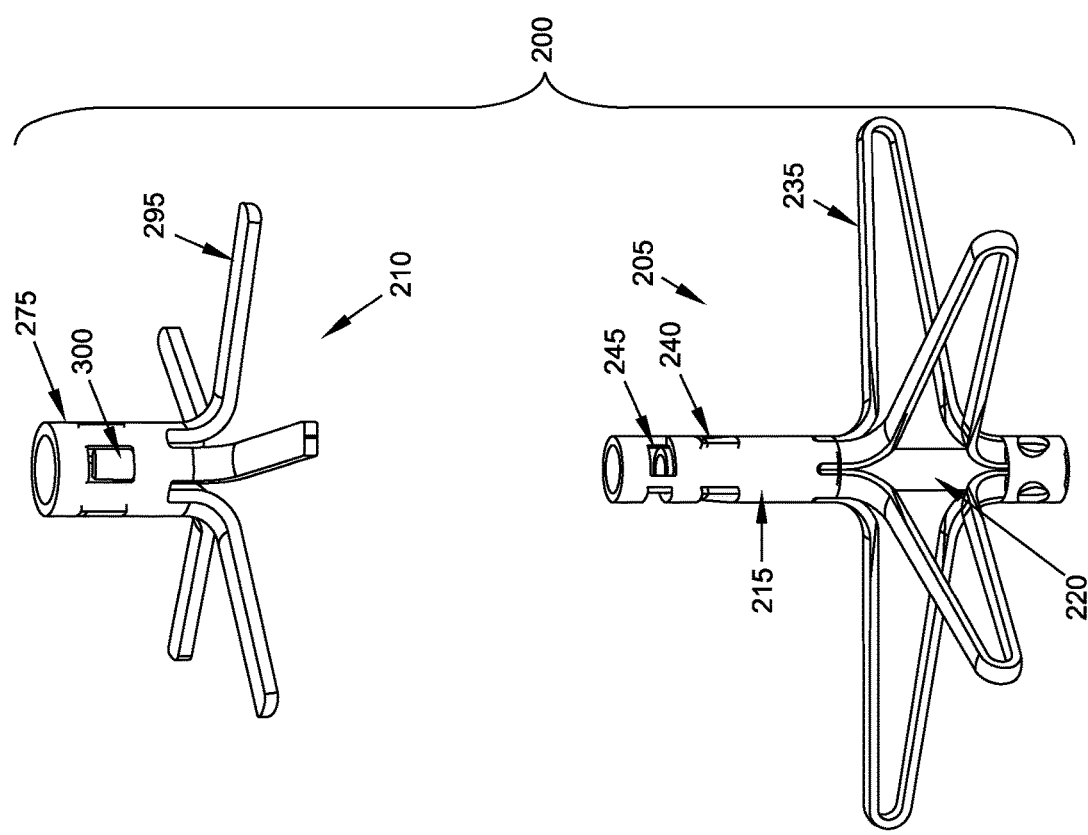

Looking next at FIG. 42, there is shown a two-part occluder 200 formed in accordance with the present invention. Two-part occluder 200 generally comprises a distal implant 205 and a proximal implant 210.

Distal implant 205 is shown in further detail in FIGS. 43-46. Distal implant 205 comprises a distal implant body 215 and a distal implant locking tube 220. Distal implant body 215 comprises a tube 225 having a distal end 226, a proximal end 227, and a lumen 230 extending therebetween. Tube 225 is slit intermediate its length so as to define a plurality of legs 235. A set of inwardly-projecting tangs 240 are formed in tube 225 between legs 235 and proximal end 227. A set of windows 245 are formed in tube 225 between inwardly-projecting tangs 240 and proximal end 227. Distal implant body 215 is preferably formed out of an elastic material (e.g., a shape memory material having superelastic properties such as Nitinol or superelastic polymers, including superelastic plastics) and constructed so that its legs 235 normally project laterally away from the longitudinal axis of tube 225 (e.g., in the manner shown in FIGS. 43 and 44), however, due to the elastic nature of the material used to form distal implant body 215, legs 235 can be constrained inwardly (e.g., within the lumen of a delivery needle, as will hereinafter be discussed) so that distal implant body 215 can assume a substantially linear disposition. See, for example, FIG. 46, which shows legs 235 moved inwardly relative to the position shown in FIGS. 43 and 44. However, when any such constraint is removed, the elastic nature of the material used to form distal implant body 215 causes legs 235 to return to the position shown in FIGS. 43 and 44.

Distal implant locking tube 220 (FIG. 45) comprises a generally tubular structure having a distal end 250, a proximal end 260 and a lumen 262 extending therebetween. A set of windows 265 are formed in the distal implant locking tube 220, with windows 265 being disposed distal to proximal end 260.

Distal implant locking tube 220 is disposed within lumen 230 of distal implant body 215. When distal implant 205 is in its aforementioned substantially linear condition (i.e., with legs 235 restrained in an in-line condition), distal implant locking tube 220 terminates well short of tangs 240 of distal implant body 215, so that the proximal end 227 of distal implant body 215 can move longitudinally relative to distal end 226 of distal implant body 215. However, when the proximal end 227 of distal implant body 215 is moved distally a sufficient distance to allow full radial expansion of legs 235 (see FIG. 42), locking tangs 240 of distal implant body 215 will be received within windows 265 of distal implant locking tube 220, whereby to lock distal implant 205 in its radially-expanded condition (i.e., with legs 235 projecting laterally away from the longitudinal axis of tube 225, e.g., in the manner shown in FIGS. 43 and 44). Spot welds applied via openings 270 formed in the distal end 226 of distal implant body 215 serve to lock distal implant locking tube 220 to distal implant body 215, whereby to form a singular structure (see FIGS. 43 and 46).

Looking next at FIGS. 47 and 48, proximal implant 210 comprises a tube 275 having a distal end 280, a proximal end 285, and a lumen 290 extending therebetween. Tube 275 is slit at its distal end so as to define a plurality of legs 295. A set of inwardly-projecting tangs 300 are formed in tube 275 between legs 295 and proximal end 285. Proximal implant 210 is preferably formed out of an elastic material (e.g., a shape memory material having superelastic properties such as Nitinol) and constructed so that its legs 295 normally project laterally away from the longitudinal axis of tube 275 (e.g., in the manner shown in FIG. 47), however, legs 295 can be constrained inwardly (e.g., within the lumen of a delivery tube, as will hereinafter be discussed) so that proximal implant 210 can assume a substantially linear disposition. See, for example, FIG. 48, which shows legs 295 moved inwardly relative to the position shown in FIG. 47. However, when any such constraint is removed, the elastic nature of the material used to form proximal implant 210 causes legs 295 to return to the position shown in FIG. 47.

Figure 82:
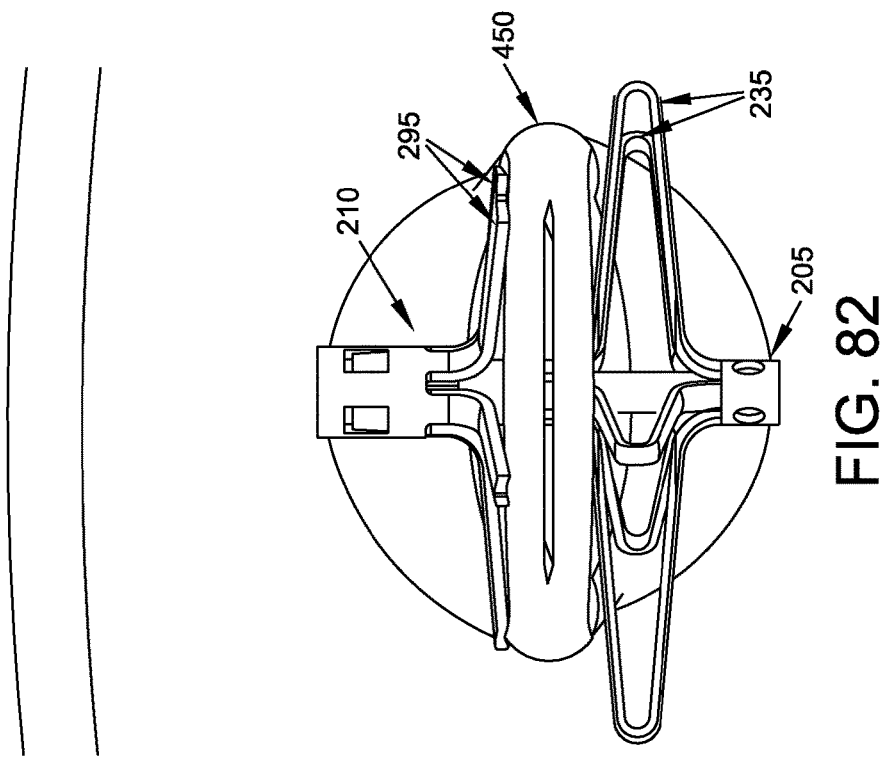

As will hereinafter be discussed, distal implant 205 and proximal implant 210 are configured and sized so that tube 225 of distal implant body 215 can be received in lumen 290 of proximal implant 210, with the expanded legs 235 of distal implant 205 opposing the expanded legs 295 of proximal implant 210 (see, for example, FIG. 82), whereby to impose a clamping action on the side wall of a blood vessel (e.g., vein) disposed therebetween and thereby occlude the blood vessel, as will hereinafter be discussed in further detail (or, as an alternative, the opposing expanded legs of the proximal and distal implants could interdigitate to impose the clamping action). Furthermore, distal implant 205 and proximal implant 210 are configured and sized so that they may be locked in this position, inasmuch as inwardly-projecting tangs 300 of proximal implant 210 will project into windows 245 of distal implant 205.

Two-part occluder 200 is intended to be deployed using associated installation apparatus. This associated installation apparatus preferably comprises a hollow needle 305 (FIG.

Figure 50:
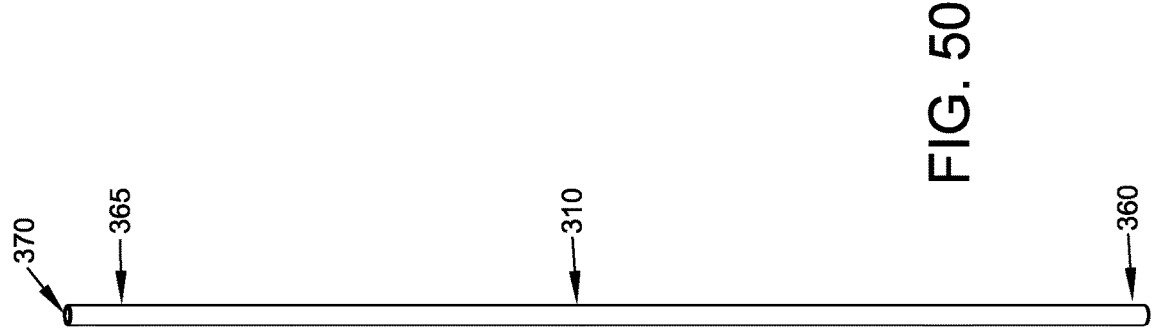
FIGS. 49-58 are schematic views showing installation apparatus which may be used to deploy the two-part occluder of FIGS. 42-48.
Figure 58:
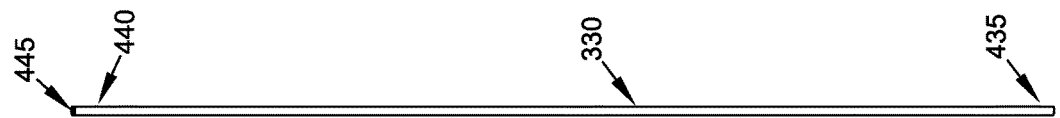
Figure 57:
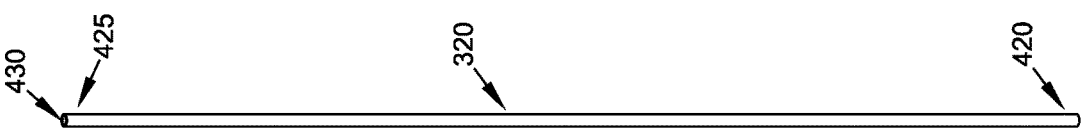
Figure 56:
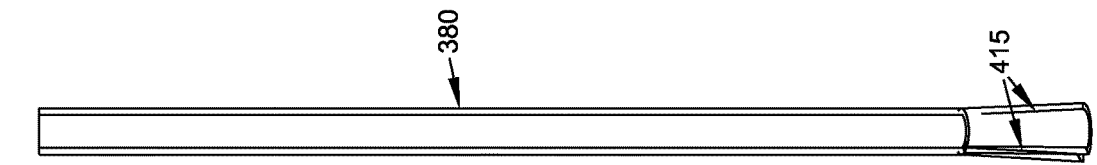
Figure 55:
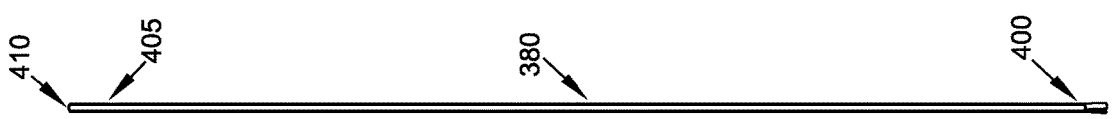

49) for penetrating tissue, a distal implant delivery tube 310 (FIG. 50) for delivering distal implant 205 through hollow needle 305 to the far side of the blood vessel which is to be occluded, a composite guidewire 315 (FIGS. 51-56) for supplying support to various components during delivery and deployment, a push rod 320 (FIG. 57) for delivering various components over composite guidewire 315, and a proximal implant delivery tube 330 (FIG. 58) for delivering proximal implant 210 for mating with distal implant 205, as will hereinafter be discussed.

Figure 49:
Figures 53, 54:
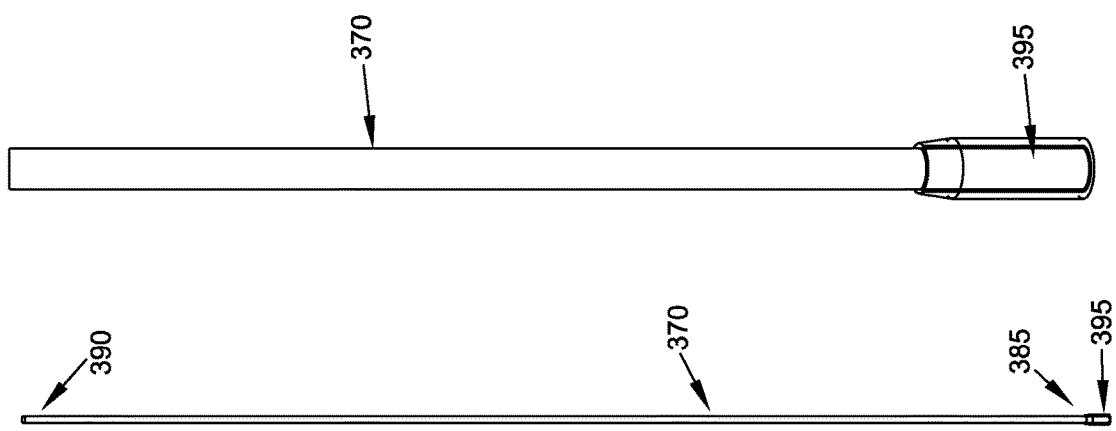
Figures 51, 52:
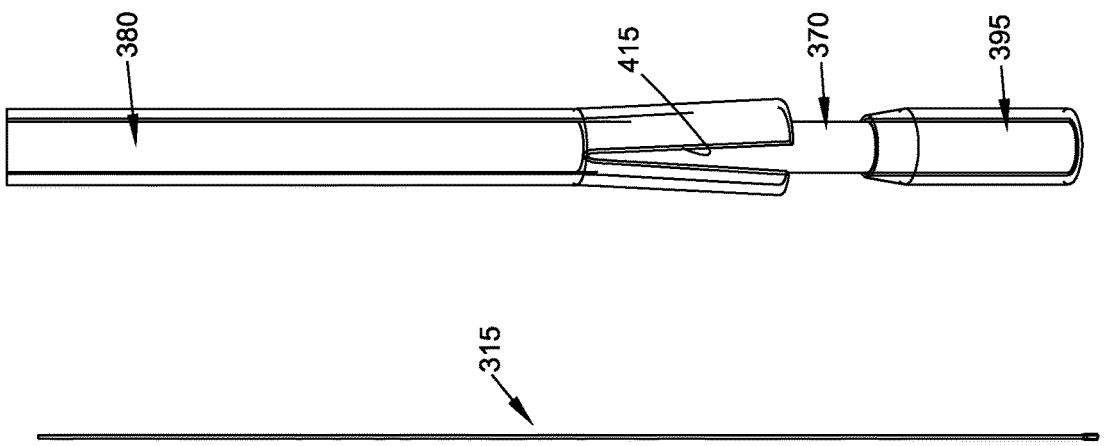

Hollow needle 305 (FIG. 49) comprises a distal end 335, a proximal end 340 and a lumen 345 extending therebetween. Distal end 335 terminates in a sharp point 350. In one preferred form of the invention, hollow needle 305 comprises a side port 355 which communicates with lumen 345.

Distal implant delivery tube 310 (FIG. 50) comprises a distal end 360, a proximal end 365 and a lumen 370 extending therebetween.

Composite guidewire 315 (FIGS. 51-56) comprises a guidewire rod 370 and a guidewire sheath 380. Guidewire rod 370 comprises a distal end 385 and a proximal end 390. Distal end 385 terminates in an enlargement 395. Guidewire sheath 380 comprises a distal end 400, a proximal end 405 and a lumen 410 extending therebetween. The distal end 400 of guidewire sheath 380 comprises at least one, and preferably a plurality of, proximally-extending slits 415. Proximally-extending slits 415 open on the distal end of guidewire sheath 380 and allow the distal end of guidewire sheath 380 to radially expand somewhat. As will hereinafter be discussed, guidewire rod 370 and guidewire sheath 380 are configured and sized so that guidewire rod 370 can be received in lumen 410 of guidewire sheath 380. Furthermore, when guidewire rod 370 is forced proximally relative to guidewire sheath 380, the proximally-extending slits 415 in guidewire sheath 380 allow the distal end of the guidewire sheath 380 to expand somewhat so as to receive at least some of the enlargement 395 formed on the distal end of guidewire rod 370. As this occurs, the distal end of guidewire sheath 380 will expand radially.

Push rod 320 (FIG. 57) comprises a distal end 420, a proximal end 425 and a lumen 430 extending therebetween.

Proximal implant delivery tube 330 (FIG. 58) comprises a distal end 435, a proximal end 440 and a lumen 445 extending therebetween.

Two-part occluder 200 and its associated installation apparatus are preferably used as follows.

First, hollow needle 305 (carrying distal implant delivery tube 310 therein, which in turn contains the composite guidewire 315 therein, upon which is mounted distal implant 205) is passed through the skin of the patient, through intervening tissue, and across the blood vessel (e.g., vein 450) which is to be occluded. See FIGS. 59-61. As this is done, any blood flowing out side port 355 can be monitored—excessive or pulsatile blood flow can indicate that hollow needle has accidentally struck an artery.

Figure 62:
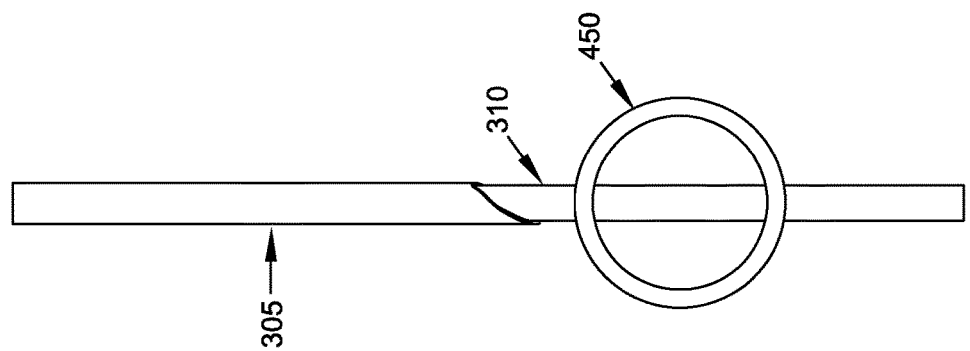

Next, hollow needle 305 is retracted, leaving distal implant delivery tube 310 extending across the blood vessel. See FIG. 62.

Figure 63:
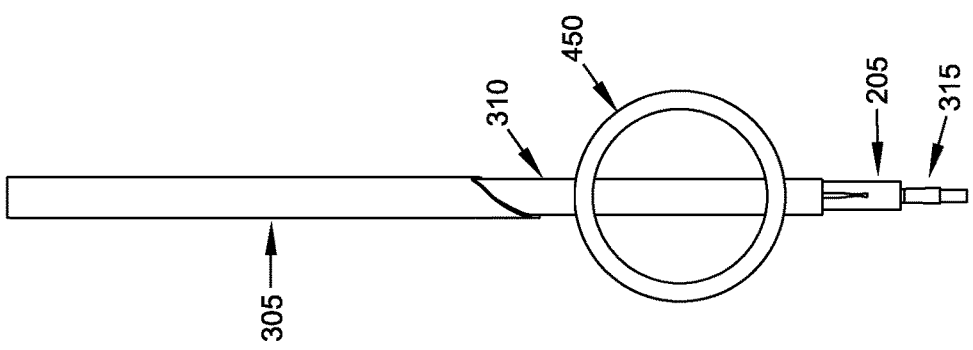

Then distal implant delivery tube 310 is retracted somewhat so as to expose the distal ends of composite guidewire, or rod, 315 and distal implant 205. See FIG. 63.

Figure 64:
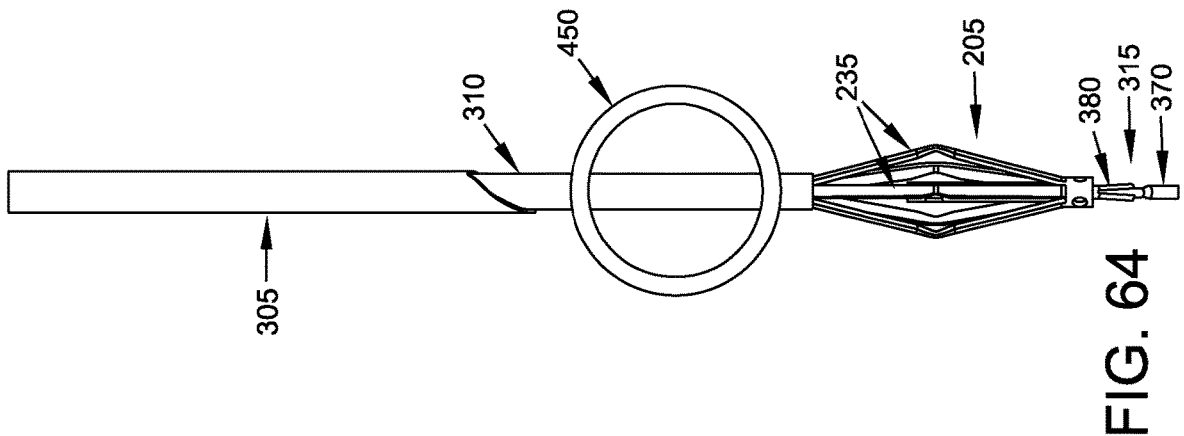

Next, composite guidewire 315, push rod 320 and distal implant 205 are all moved distally, so as to advance the distal ends of composite guidewire 315 and the distal implant 205 out of the distal end of distal implant delivery tube 310. As this occurs, legs 235 of distal implant 205 are released from the constraint of distal implant delivery tube 310 and expand radially. See FIGS. 64 and 65.

Then, with push rod 320 being held in place against the proximal end of distal implant 205, composite guidewire 315 is pulled proximally so as to bring the distal end of distal implant 205 toward the proximal end of distal implant 205, whereby to cause locking tangs 240 of distal implant body 215 to enter windows 265 of distal implant locking tube 220, whereby to lock legs 235 in their radially-expanded condition (see FIG. 66).

Figure 67:
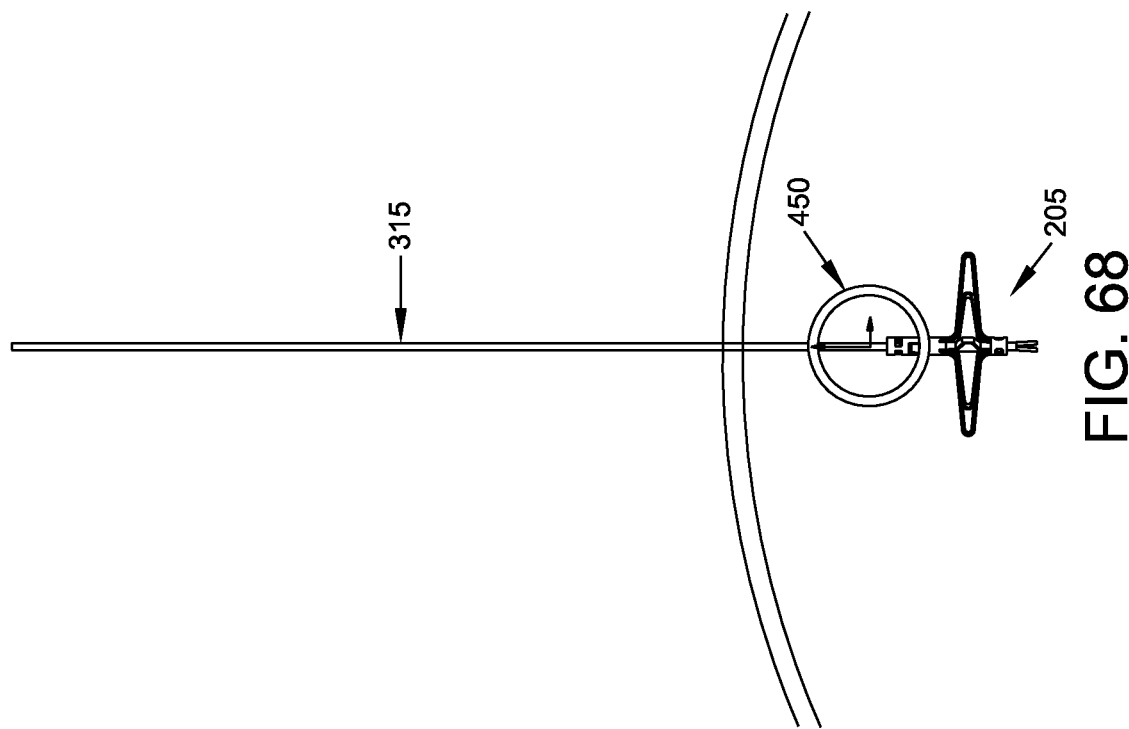
Figure 68:
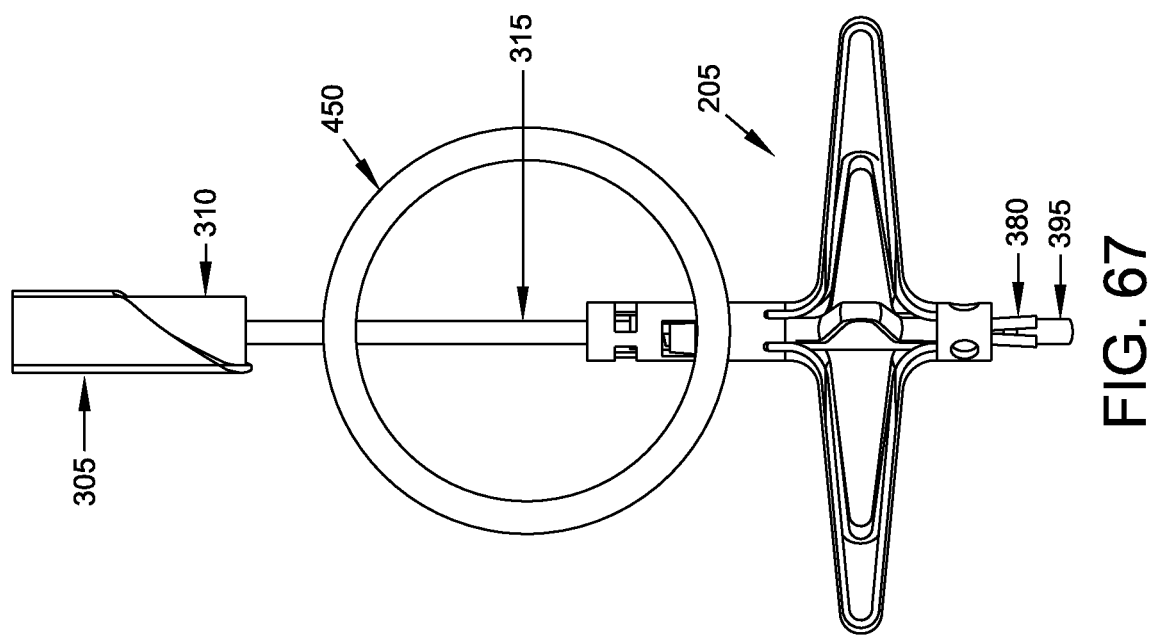
Figure 70:
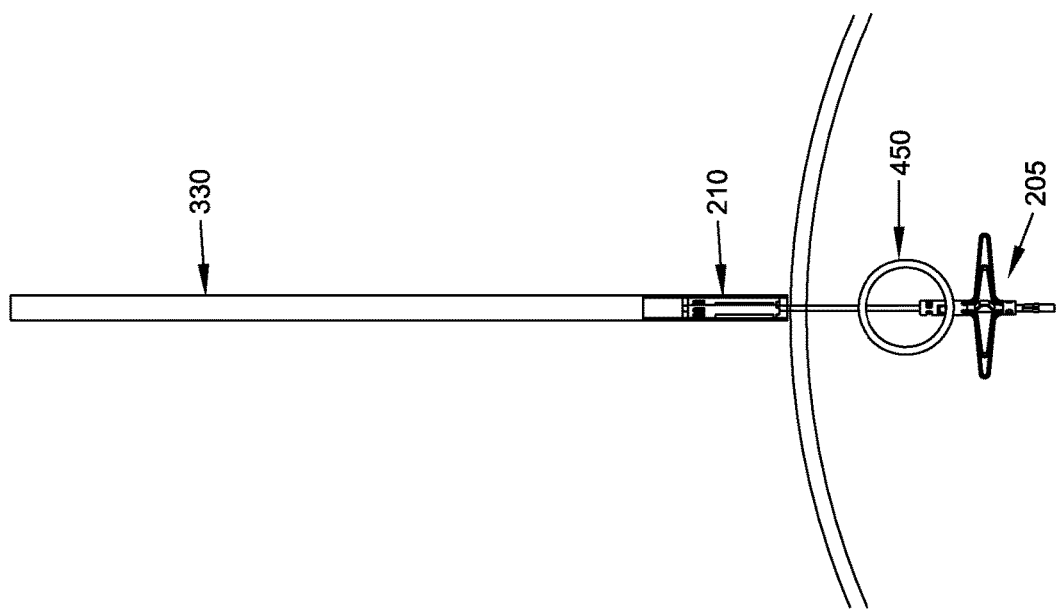
Figure 69:
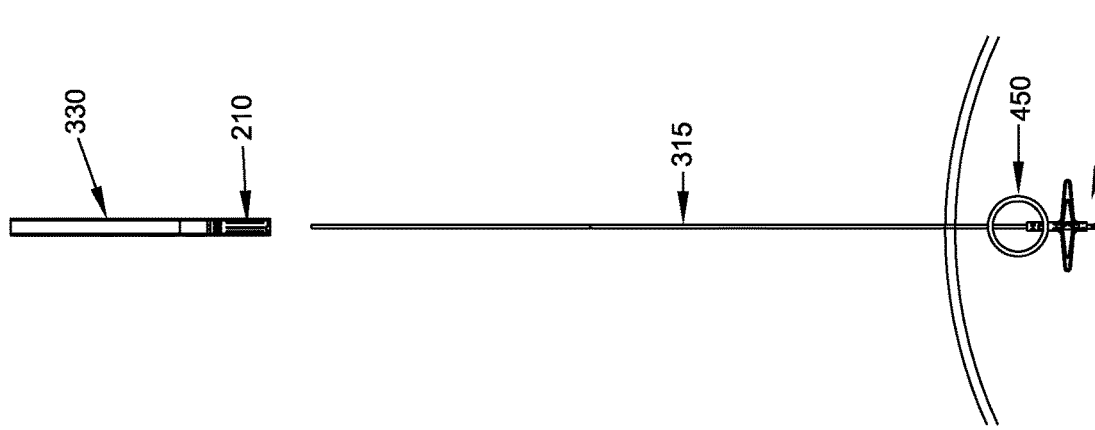
Figure 71:
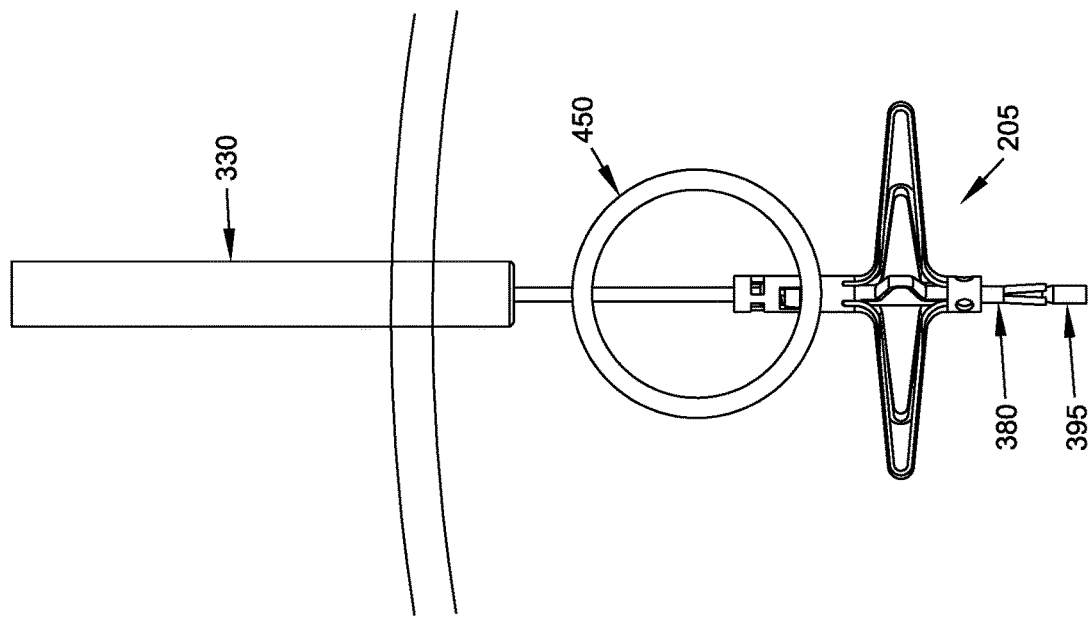
Figure 72:
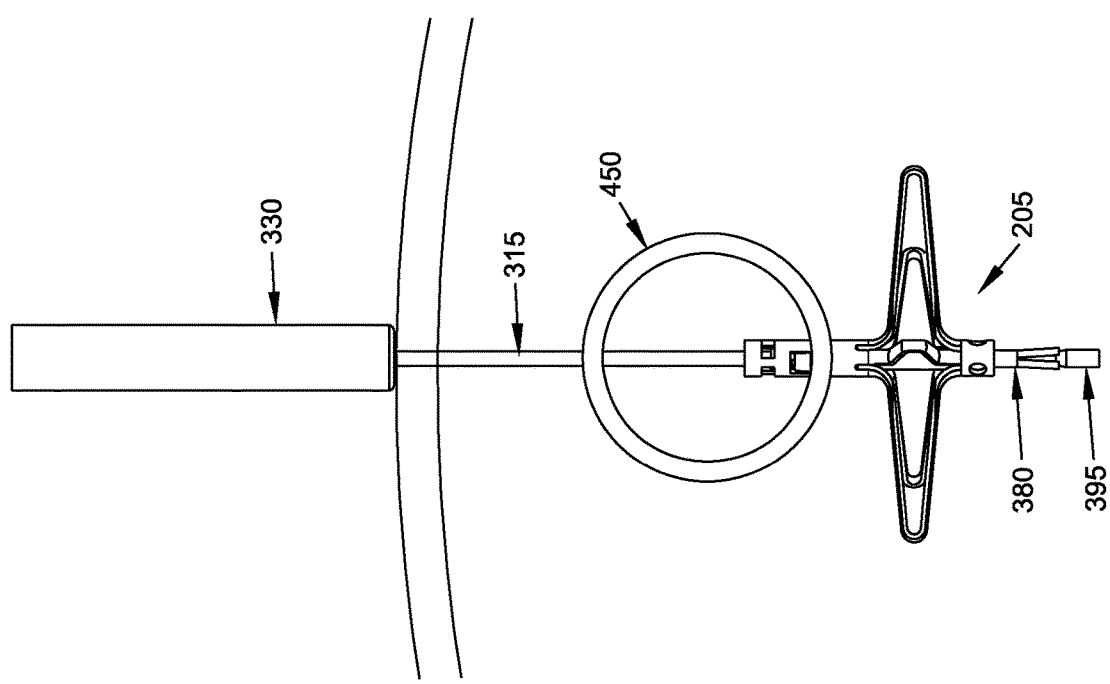
Figure 74:
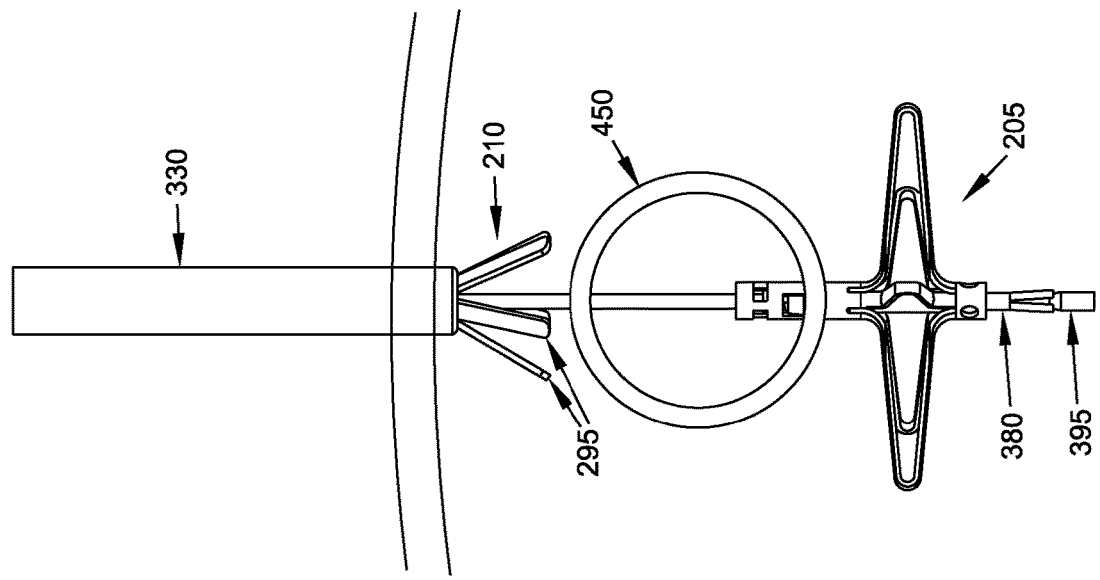
Figure 73:
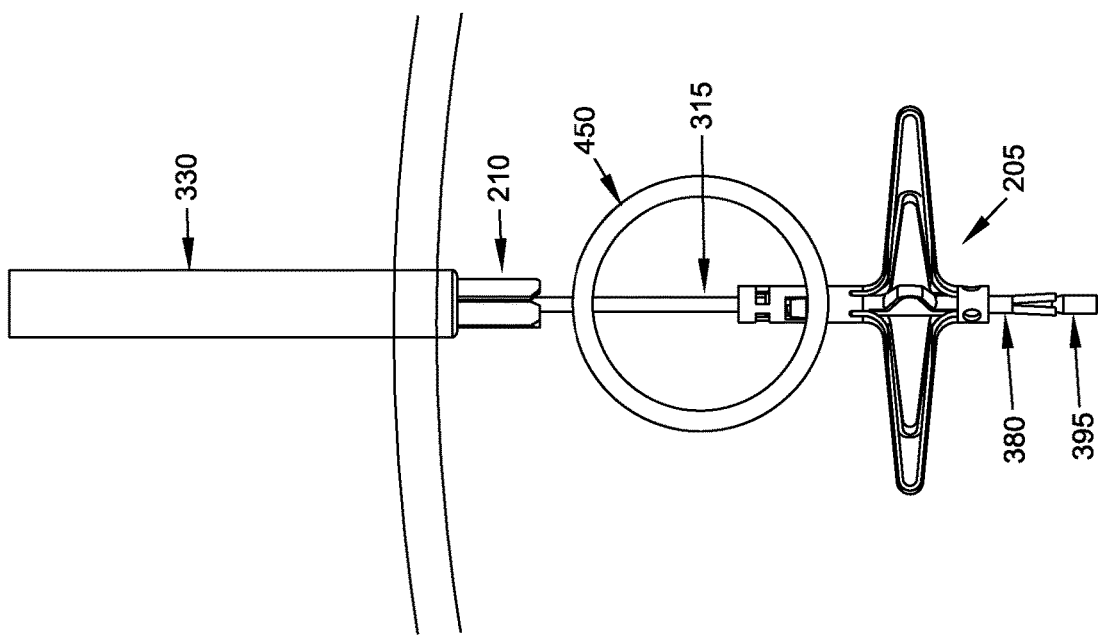
Figure 76:
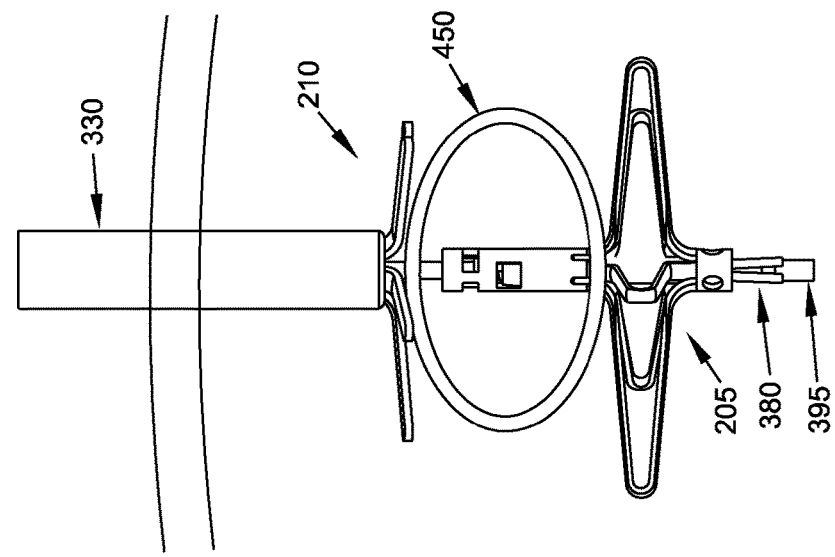
Figure 75:
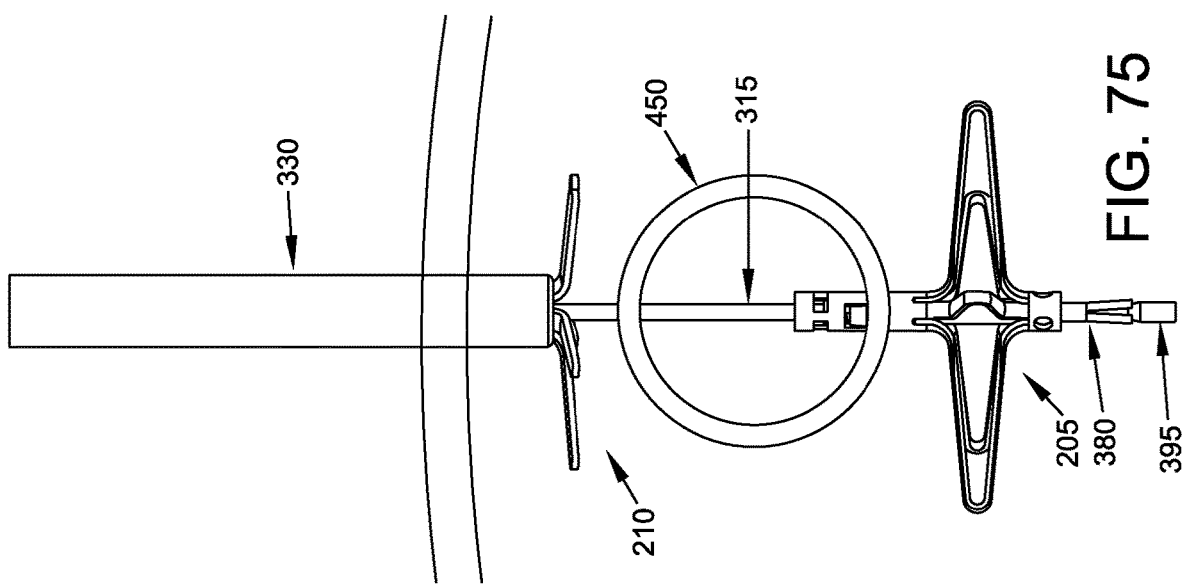

At this point, hollow needle 305, distal implant delivery tube 310 and push rod 320 may be removed (FIG. 67), leaving distal implant 205 mounted on composite guidewire 315, with the legs 235 fully deployed on the far side of the blood vessel and the proximal end of distal implant 205 extending into the interior of the blood vessel (FIG. 68).

Next, proximal implant delivery tube 330 (carrying proximal implant 210 therein) is advanced down composite guidewire 315, until the distal end of proximal implant delivery tube 330 sits just proximal to the blood vessel (FIGS. 69-72).

Then push rod 320 is used to advance the distal end of proximal implant 210 out of the distal end of proximal implant delivery tube 330. As this occurs, legs 295 are released from the constraint of proximal implant delivery tube 330 and open radially. See FIGS. 73-76.

Figure 77:
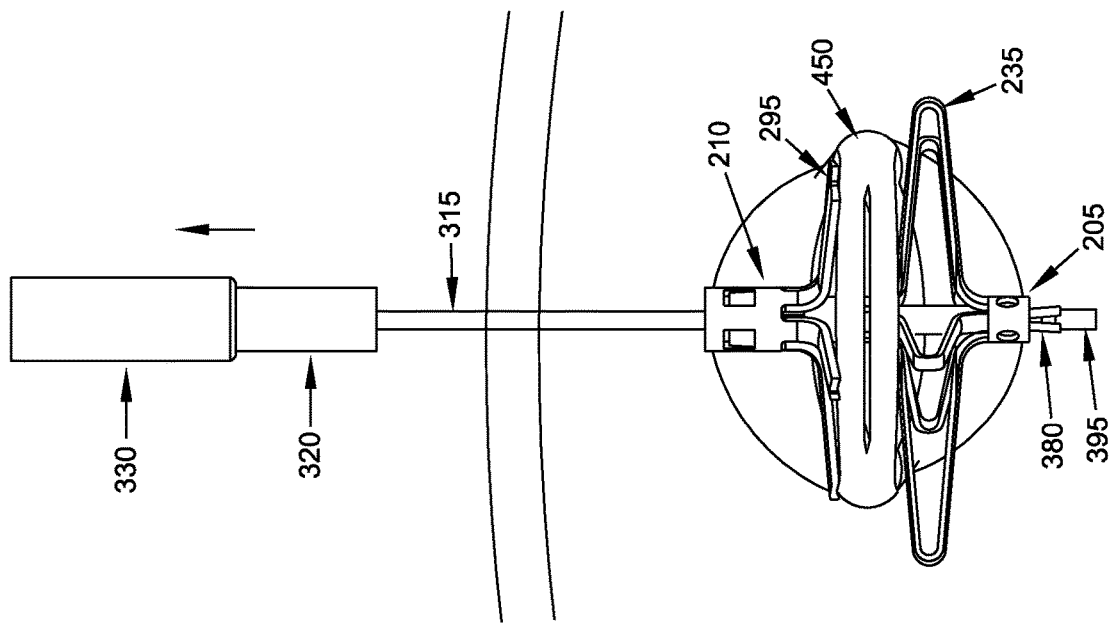

Next, using push rod 320, proximal implant 210 is pushed distally as distal implant 205 is pulled proximally using composite guidewire 315. More particularly, guidewire rod 370 is pulled proximally, which causes enlargement 395 on the distal end of guidewire rod 370 to expand guidewire sheath 380 to a size larger than lumen 262 in distal implant locking tube 220, which causes guidewire sheath 380 to move proximally, which causes proximal movement of distal implant 205. As distal implant 205 and proximal implant 210 move together, their legs 235, 295 compress the blood vessel, thereby occluding the blood vessel. Distal implant 205 and proximal implant 210 continue moving together until inwardly-projecting tangs 300 of proximal implant 210 enter windows 245 of distal implant 205, thereby locking the two members into position relative to one another. See FIG. 77.

Figure 78:
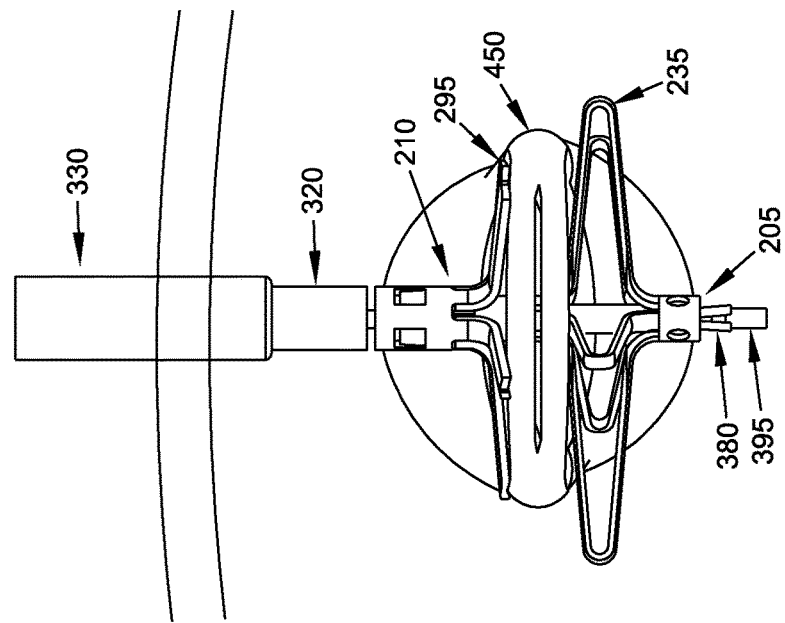

At this point push rod 320 and proximal implant delivery tube 330 are removed. See FIG. 78.

Figure 80:
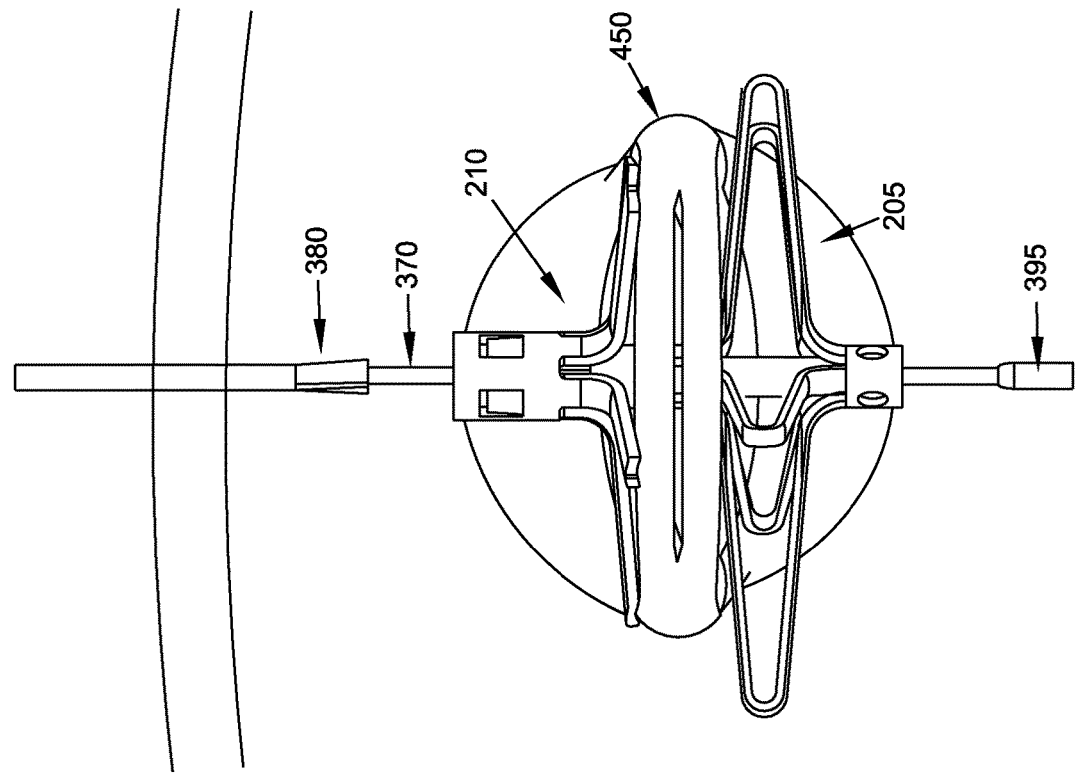
Figure 79:
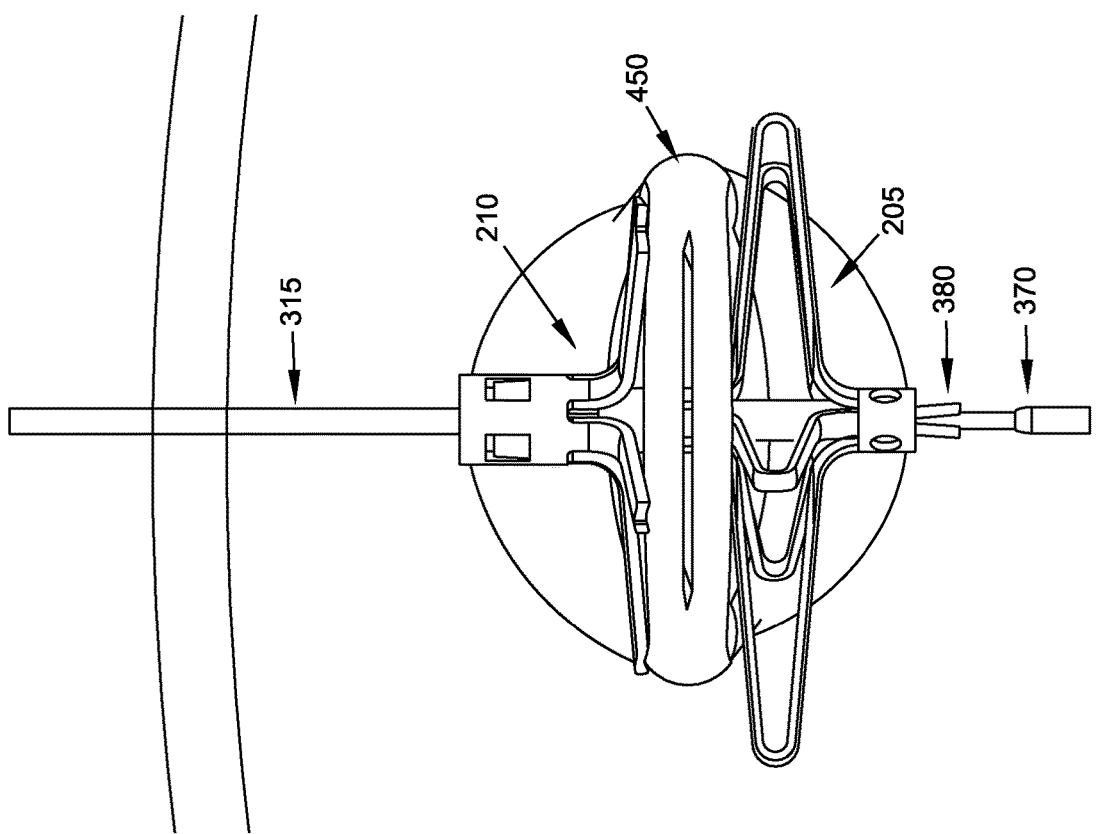
Figure 81:
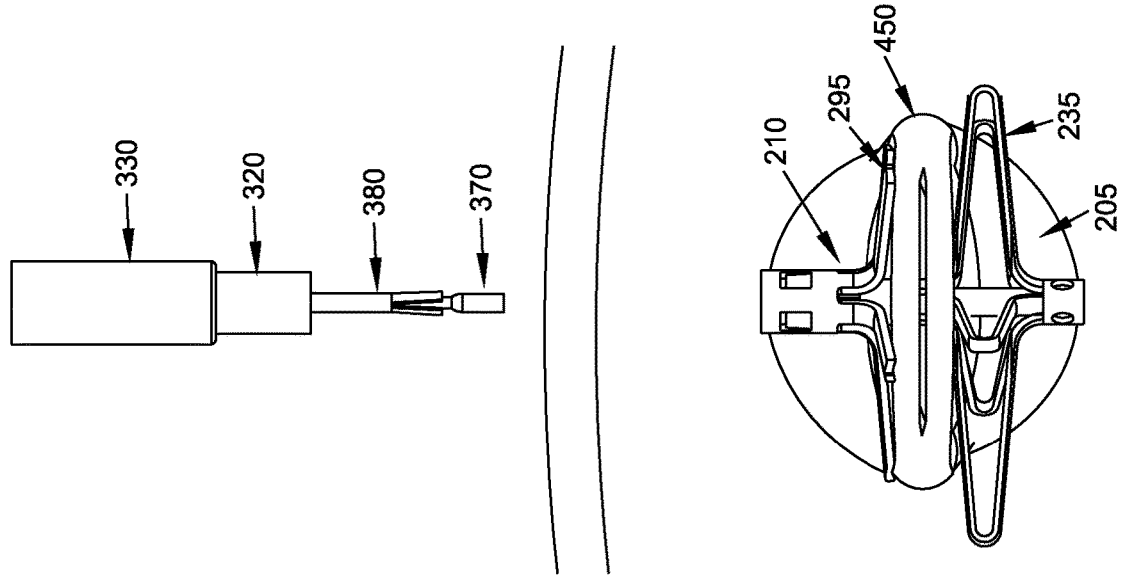
Figure 84:
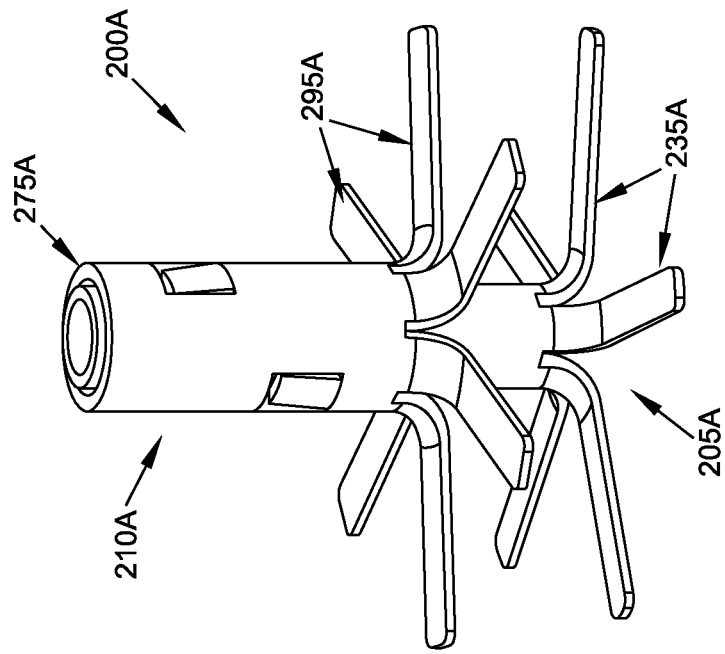
FIGS. 83-86 are schematic views showing another two-part occluder formed in accordance with the present invention.
Figure 83:
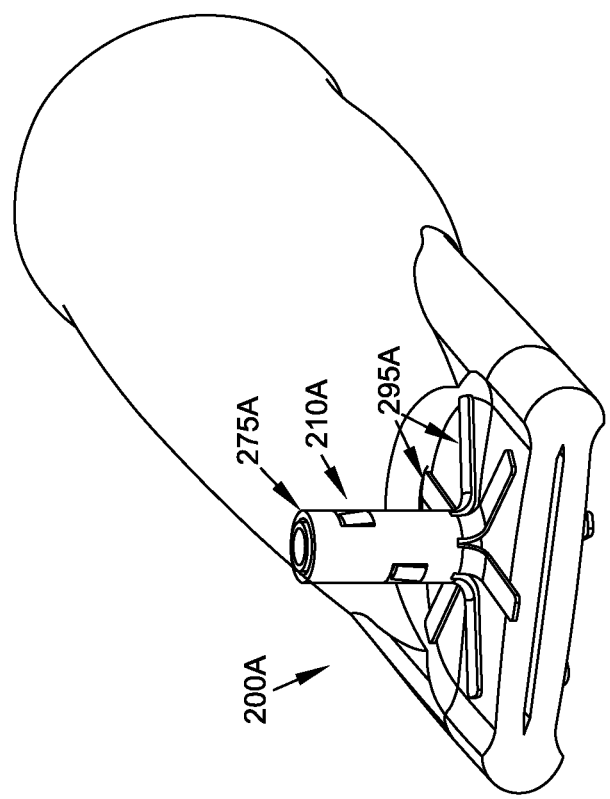
Figure 86:
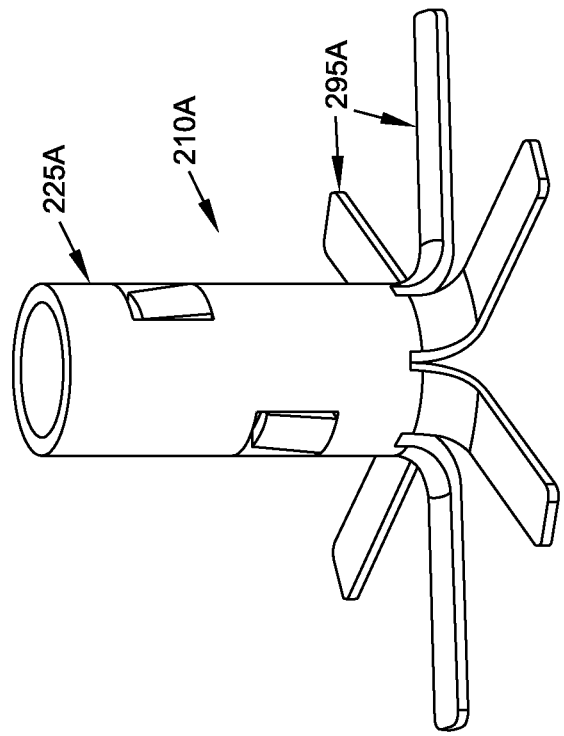
Figure 85:
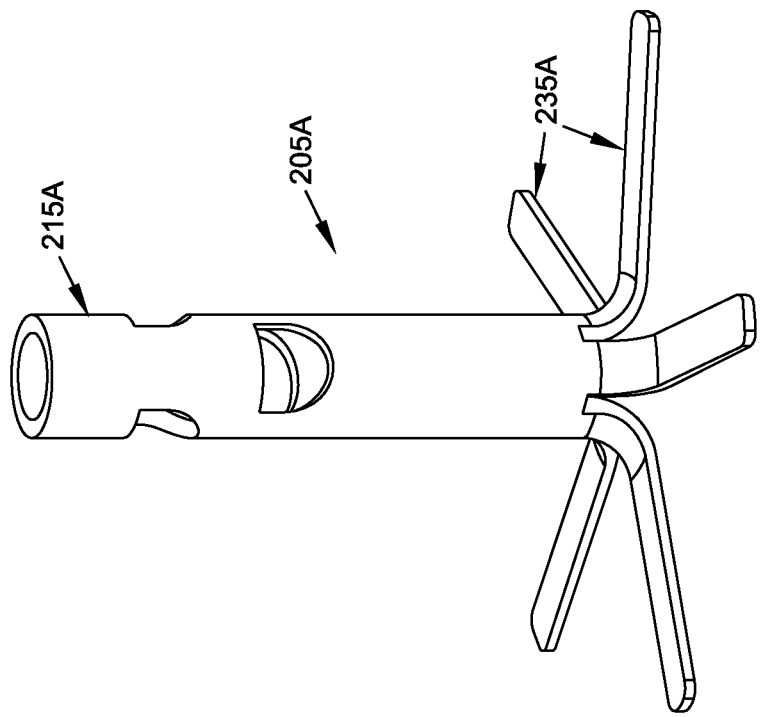
Figure 88:
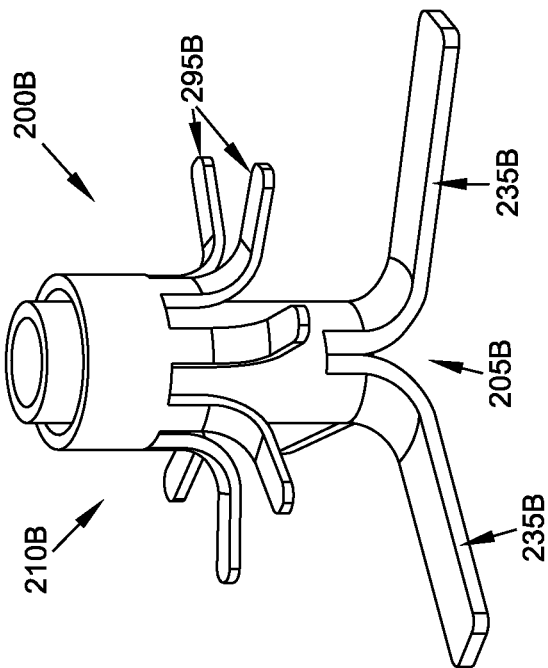
FIGS. 87-90 are schematic views showing still another two-part occluder formed in accordance with the present invention.
Figure 87:
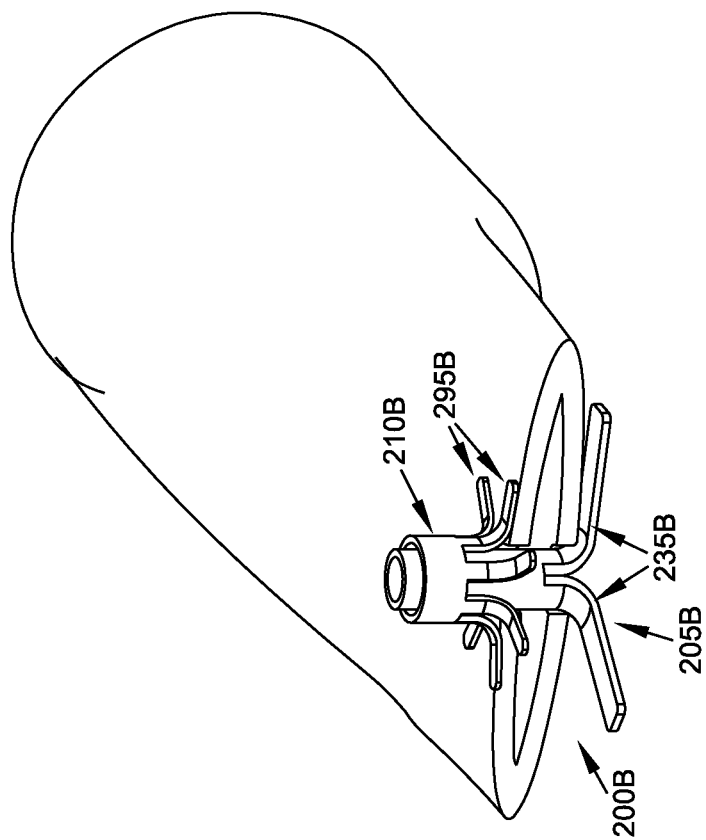
Figure 90:
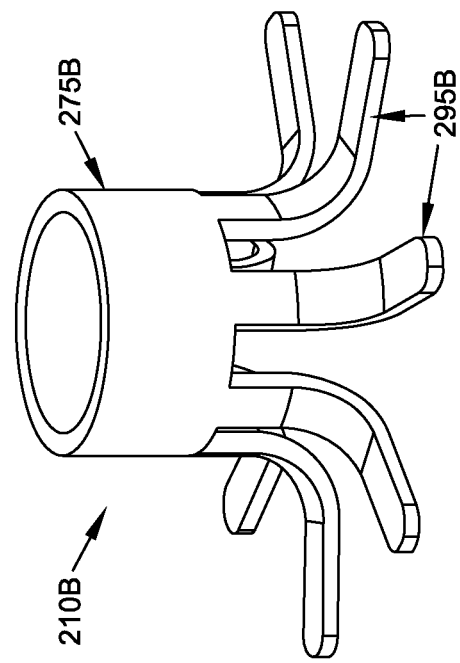
Figure 89:
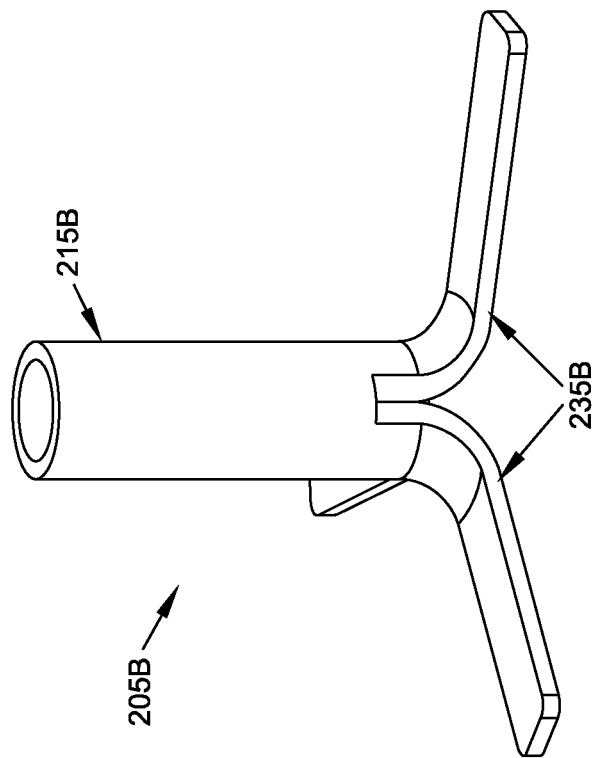
Figure 96:
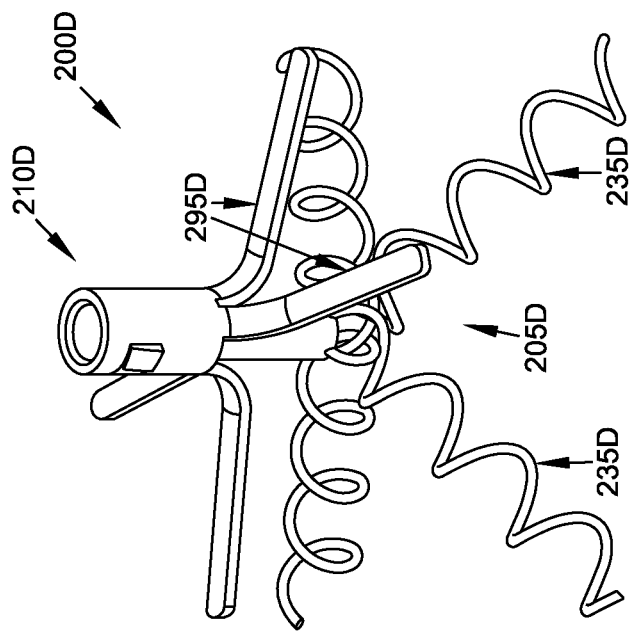
FIGS. 95-100 are schematic views showing another two-part occluder formed in accordance with the present invention.
Figure 95:
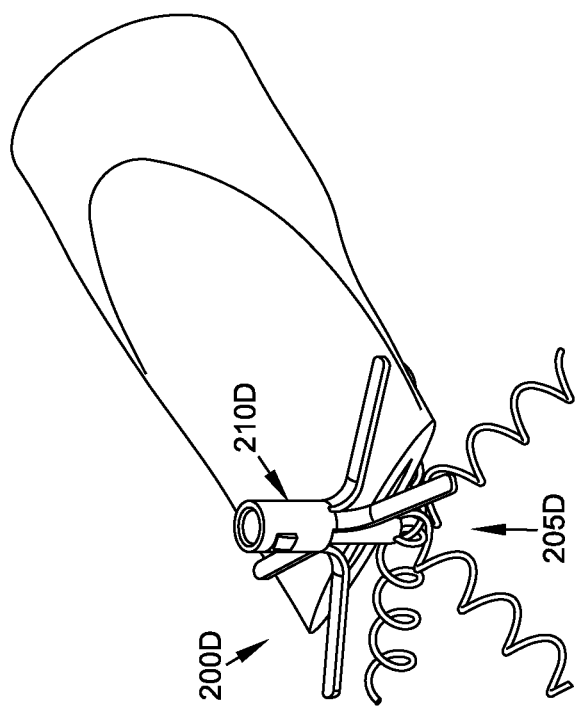
Figure 98:
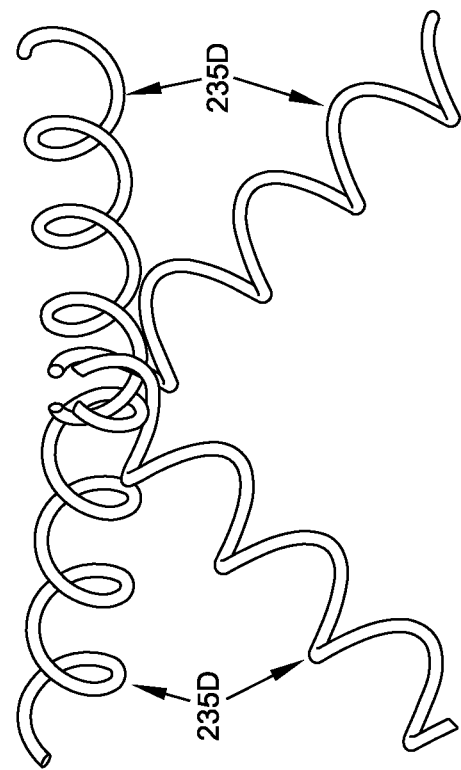
Figure 97:
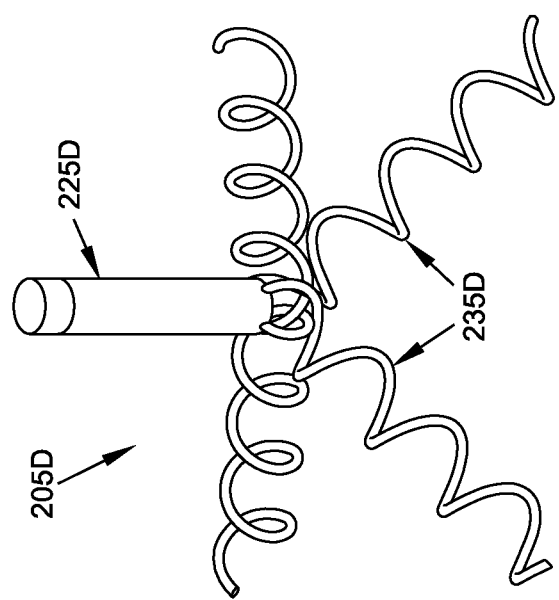
Figure 99:
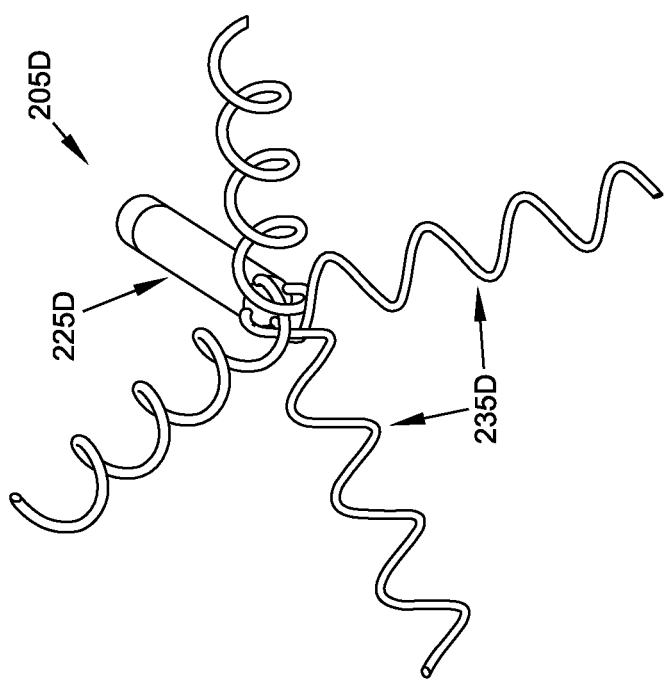
Figure 100:
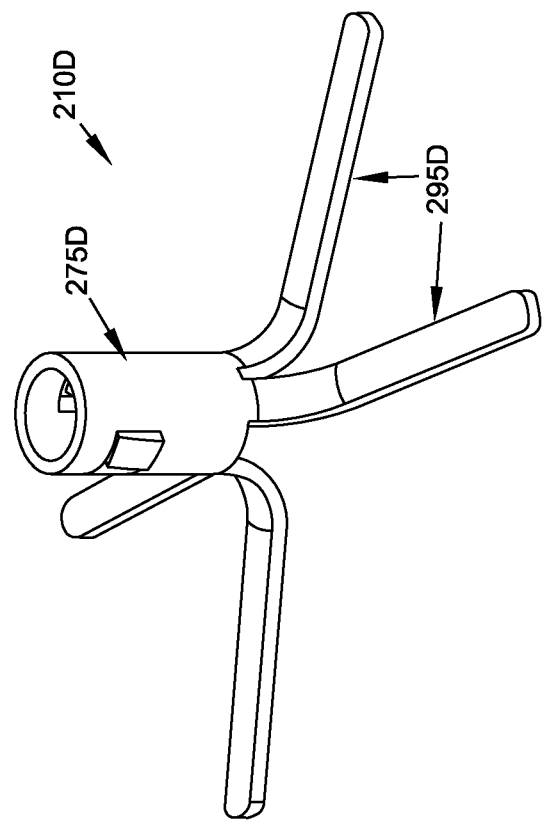

Next, composite guidewire 315 is removed. This is done by first advancing guidewire rod 370 distally (FIG. 79), which allows the distal end of guidewire sheath 380 to relax inwardly, thereby reducing its outer diameter to a size smaller than lumen 262 in distal implant locking tube 220. As a result, guidewire sheath 380 can then be withdrawn proximally through the interior of two-part occluder 200. See FIG. 80. Then guidewire rod 370 can be withdrawn proximally through the interior of two-part occluder 200. See FIG. 81.

The foregoing procedure leaves two-part occluder 200 locked in position across the blood vessel, with the opposing legs 235, 295 compressing the blood vessel, whereby to occlude the blood vessel.

FIGS. 83-86 illustrate another two-part occluder 200A having a distal implant 205A and a proximal implant 210A. Two-part occluder 200A is generally similar to the aforementioned two-part occluder 200, except that distal implant 205A utilizes a unibody construction.

FIGS. 87-90 illustrate another two-part occluder 200B. Two-part occluder 200B is generally similar to the aforementioned two-part occluder 200A, except that distal implant 205B utilizes a friction fit to lock distal implant 205B to proximal implant 210B.

FIGS. 91-94 illustrate another two-part occluder 200C having a distal implant 205C and a proximal implant 210C. Two-part occluder 200C is generally similar to the aforementioned two-part occluder 200, except that distal implant 205C comprises a tube 225C which receives and secures the proximal ends of legs 235C. Legs 235C are preferably elongated elements (e.g., bent wires) formed out of a superelastic shape memory material so as to provide the legs 235C with the desired degree of elasticity.

FIGS. 95-100 illustrate another two-part occluder 200D having a distal implant 205D and a proximal implant 210D. Two-part occluder 200D is generally similar to the aforementioned two-part occluder 200, except that distal implant 205D comprises a tube or rod 225D which receives and secures the proximal ends of legs 235D. Legs 235D are preferably coils formed out of a superelastic shape memory material so as to provide the legs 235D with the desired degree of elasticity.

In the foregoing disclosure, there is a disclosed a composite guidewire 315 for use in delivering distal implant 205 and proximal implant 210 to the anatomy. As noted above, composite guidewire 315 is formed from two parts, i.e., a guidewire rod 370 and a guidewire sheath 380. By providing composite guidewire 315 with this two-part construction, composite guidewire 315 can have its distal diameter enlarged or reduced as desired so as to permit composite guidewire 315 to bind to distal implant 205, or be separable from the distal implant 205, respectively. However, if desired, composite guidewire 315 can be replaced by an alternative guidewire which includes a mechanism for releasably binding the alternative guidewire to distal implant 205. By way of example but not limitation, such an alternative guidewire may include screw threads, and distal implant 205 may include a screw recess, so that the alternative guidewire can be selectively secured to, or released from, the distal implant 205, i.e., by a screwing action.

Temporary Blood Vessel Occlusion for Extremity Trauma

Uncontrolled hemorrhage remains the most significant cause of death in victims who survive a major initial trauma, particularly in truncal and extremity injuries. A loss of 50% of blood volume without replenishment is frequently fatal, and a hypotensive patient, who has lost 30%-35% of blood volume and is in uncompensated shock, is generally close to death.

Establishing and maintaining hemostasis at the site of an injury is an important consideration in the acute management of trauma patients. The tourniquet, with or without local compression, remains the time-honored method for controlling extremity bleeding following trauma. However, tourniquets are generally only useful for controlling bleeding in limbs, and even then tourniquets suffer from the disadvantage that they limit blood flow to the entire limb and cannot target individual blood vessels within the limb. It is estimated that of all military wounded whom ultimately succumb to their wounds, approximately 10-20% die from blood loss due to inadequate compression or tourniquet application.

Thus there is also a need for effective temporary blood vessel occlusion for military and civilian trauma cases.

In addition to trauma applications, there are many instances where an occlusion device may be implanted and then, at a later time (e.g., days, months, years), may be removed. Examples of such uses of temporary occlusion devices include reversible occlusion of fallopian tubes, temporary occlusion of the saphenous vein during pregnancy and subsequent removal of the occlusion device at the conclusion of pregnancy so as to restore blood flow through, etc.

The present invention also envisions deployment of temporary occlusion devices that can be left in the body permanently.

The present invention also provides a novel temporary occlusion device (hereinafter sometimes referred to as a "temporary occluder") that can be deployed percutaneously to temporarily occlude major blood vessels (e.g., arteries) until specialized care can be obtained to surgically control massive hemorrhage following civilian or military trauma. The novel temporary occluder of the present invention may be used as an alternative to a conventional tourniquet to control major extremity bleeding following trauma, providing a more effective, reliable and highly targeted method to control major blood vessel hemorrhage. Furthermore, unlike a conventional tourniquet, the temporary occluder of the present invention may be used even in the presence of soft tissue injury with minimal patient discomfort. Once deployed, minimal post-deployment supervision is required during the time required to transport the patient to the specialized care required to surgically repair the damaged blood vessel. The present invention requires accessing the damaged blood vessel (e.g., major artery) with a needle or other device, but this is typically within the level of expertise expected of the average military medic or civilian emergency medical technician. The utilization of ultrasound to identify and access the damaged blood vessel significantly simplifies the temporary occlusion procedure. Deployment comprises passing a portion of the temporary occluder across the blood vessel (e.g., artery) so that a distal portion of the temporary occluder bears against the outside surface of the blood vessel on the far side of the blood vessel, and positioning a proximal portion of the temporary occluder against the outside surface of the blood vessel on the near side of the blood vessel, or against the outside surface of the skin, whereby to establish an occluding compression across the blood vessel. Once deployed, removal of the temporary occluder may be performed in the specialized care center at the appropriate time. Following removal of the temporary occluder, hemostasis of the punctures caused by deployment of the temporary occluder across the blood vessel may be obtained with standard manual compression of the blood vessel, thus minimizing the need for further blood vessel repair. Alternatively, other means such as cauterization of the tissue, deploying a polymeric sealant, or deploying gauze or a pad, or positioning a coated stent in the vessel, may be used to arrest blood flow.

Figure 101:
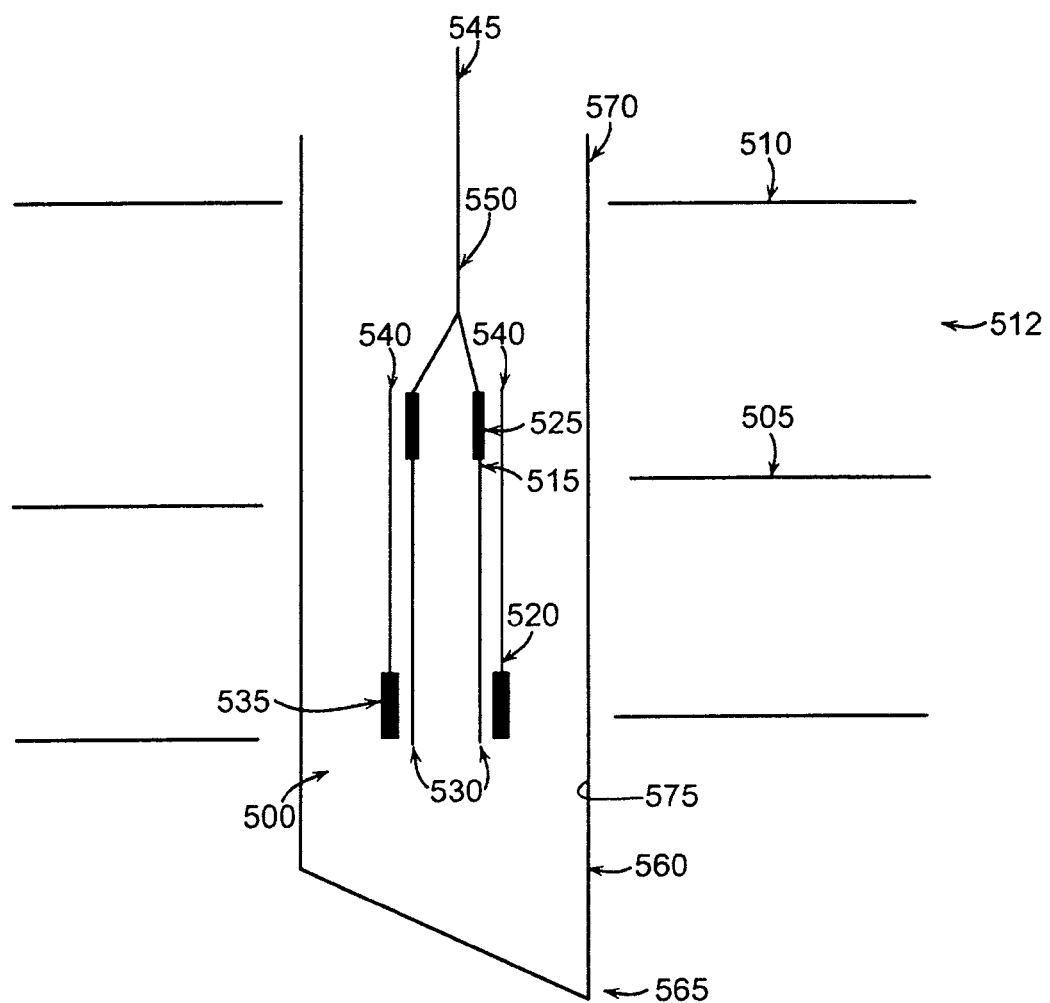
FIGS. 101-103 are schematic views showing a temporary occluder formed in accordance with the present invention.
Figure 102:
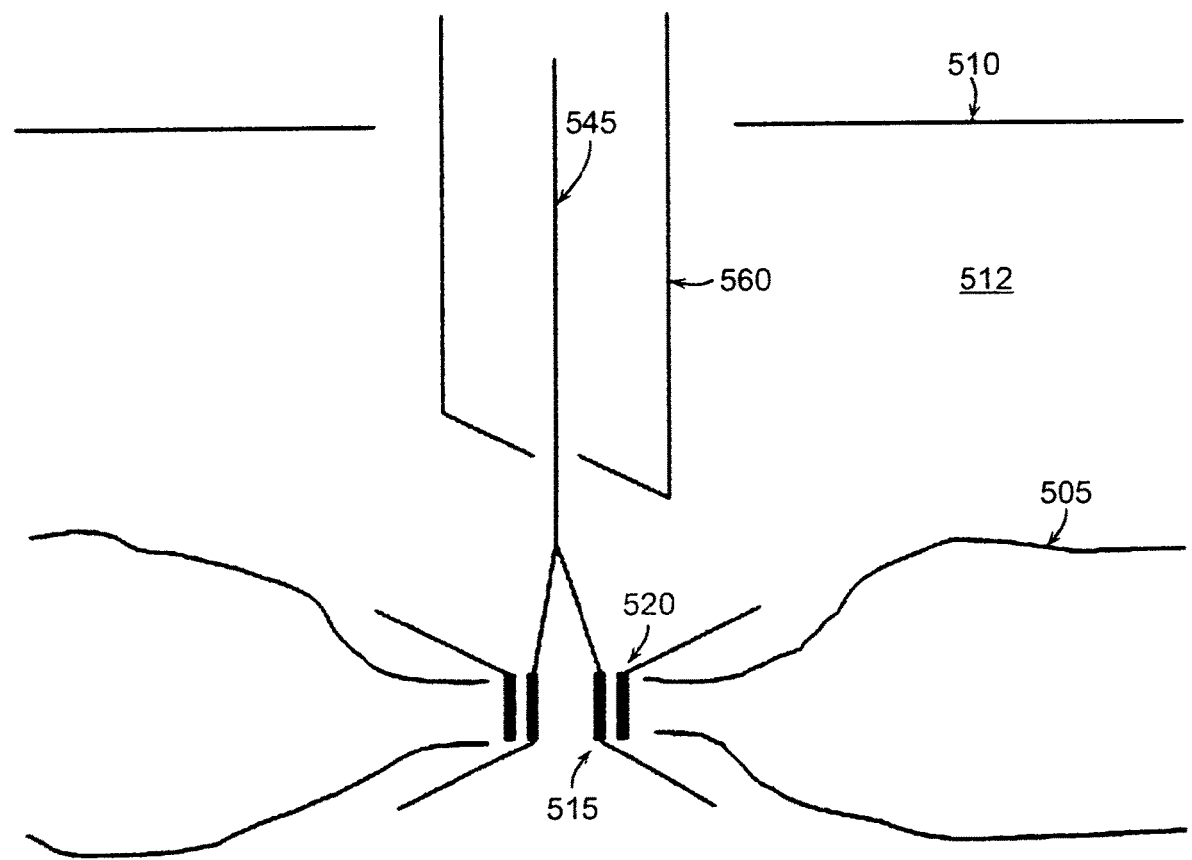
Figure 103:
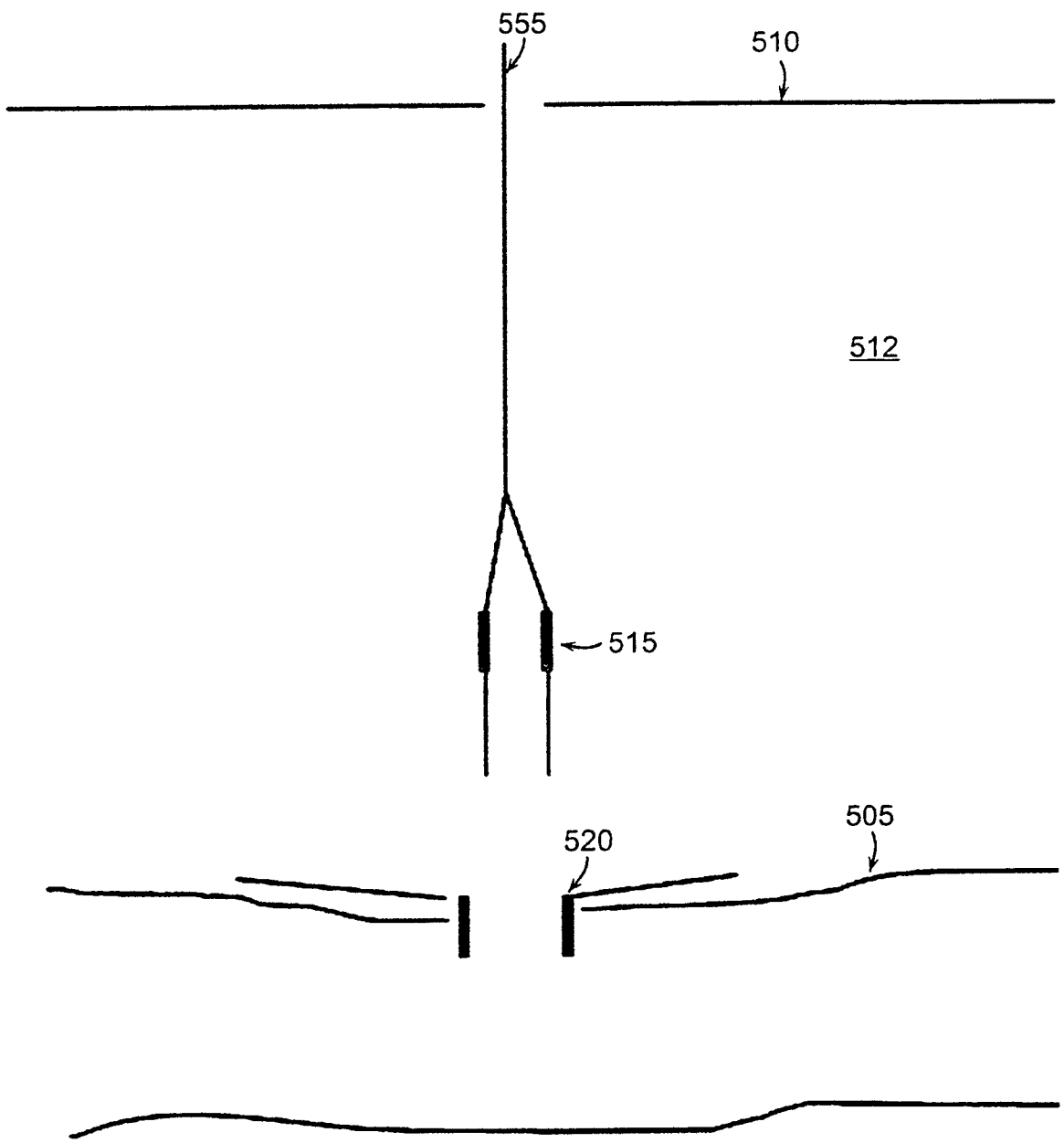

Looking now at FIGS. 101-103, there is shown a temporary occluder 500 formed in accordance with the present invention. Temporary occluder 500 may be used percutaneously to temporarily occlude a blood vessel 505 disposed beneath the surface of skin 510, wherein intervening tissue 512 is disposed between the surface of skin 510 and blood vessel 505.

Temporary occluder 500 generally comprises a distal portion 515 and a proximal portion 520. Distal portion 515 generally comprises a cylindrical body 525 having a plurality of laterally-expandable legs 530 connected thereto. By way of example but not limitation, distal portion 515 may be formed out of a Nitinol cylinder having distal slits formed therein, whereby to form cylindrical body 525 and laterally-expandable legs 530. Proximal portion 520 generally comprises a cylindrical body 535 having a plurality of laterally-expandable legs 540 connected thereto. By way of example but not limitation, proximal portion 520 may be formed out of a Nitinol cylinder having proximal slits formed therein, whereby to form cylindrical body 535 and laterally-expandable legs 540. In one embodiment, each laterally-expandable leg 530, 540 is designed with an appropriate length to minimize penetration into any tissues which may reside adjacent to the blood vessel. In one embodiment, each laterally-expandable leg 530, 540 is less than about 20 mm in length. In one embodiment, the cylindrical bodies 525, 535 are both less than about 18 gauge. Distal portion 515 is sized to be concentrically received within proximal portion 520 (see FIG. 101). In one preferred form of the invention, cylindrical body 535 of proximal portion 520 is approximately aligned with the distal ends of laterally-expandable legs 530 of distal portion 515, and cylindrical body 525 of distal portion 515 is approximately aligned with the proximal ends of laterally-expandable legs 540 of proximal portion 520.

Temporary occluder 500 also comprises a flexible filament 545 having a distal end 550 and a proximal end 555 (FIG. 103). Distal end 550 of flexible filament 545 is secured to cylindrical body 525 of distal portion 515.

Temporary occluder 500 is intended to be deployed using a needle 560, or other tubular element. Needle 560 comprises a distal end 565, a proximal end 570 and a lumen 575 extending therebetween. Needle 560 is sized to slidably receive temporary occluder 500 within its lumen 575.

In use, and looking now at FIG. 101, needle 560, carrying temporary occluder 500 therein, with flexible filament 545 extending from proximal end 570 of needle 560, is advanced through the skin 510 of the patient, through the intervening tissue 512, and across the blood vessel 505 which is to be occluded. Then distal portion 515 of temporary occluder 500 is pushed out of needle 560 so that laterally-expandable legs 530 of distal portion 515 deploy on the far side of blood vessel 505. As distal portion 515 of temporary occluder 500 is pushed out of needle 560, cylindrical body 525 of distal portion 515 is set so that it is approximately aligned with cylindrical body 535 of proximal portion 520. Then needle 560 is withdrawn proximally, allowing laterally-expandable legs 540 of proximal portion 520 to deploy on the near side of blood vessel 505, with laterally-expandable legs 530 of distal portion 515 cooperating with laterally-expanding legs 540 of proximal portion 520 so as to occlude blood vessel 505 (FIG. 102). Needle 560 may then be completely removed, leaving flexible filament 545 extending from the occlusion site up to the surface of the skin 510.

Thereafter, when occlusion of blood vessel 505 is no longer necessary, the proximal end 555 of flexible filament 545 (which extends above the surface of skin 510) is pulled proximally, whereby to pull distal portion 515 of temporary occluder 500 free of proximal portion 520 of temporary occluder 500, and thereby restore normal blood flow through blood vessel 505 (FIG. 103).

In another embodiment of the present invention, the laterally-expandable legs 530, 540 may be replaced by resilient (e.g., polymer) disks or umbrella structures that can open laterally.

Figure 104:
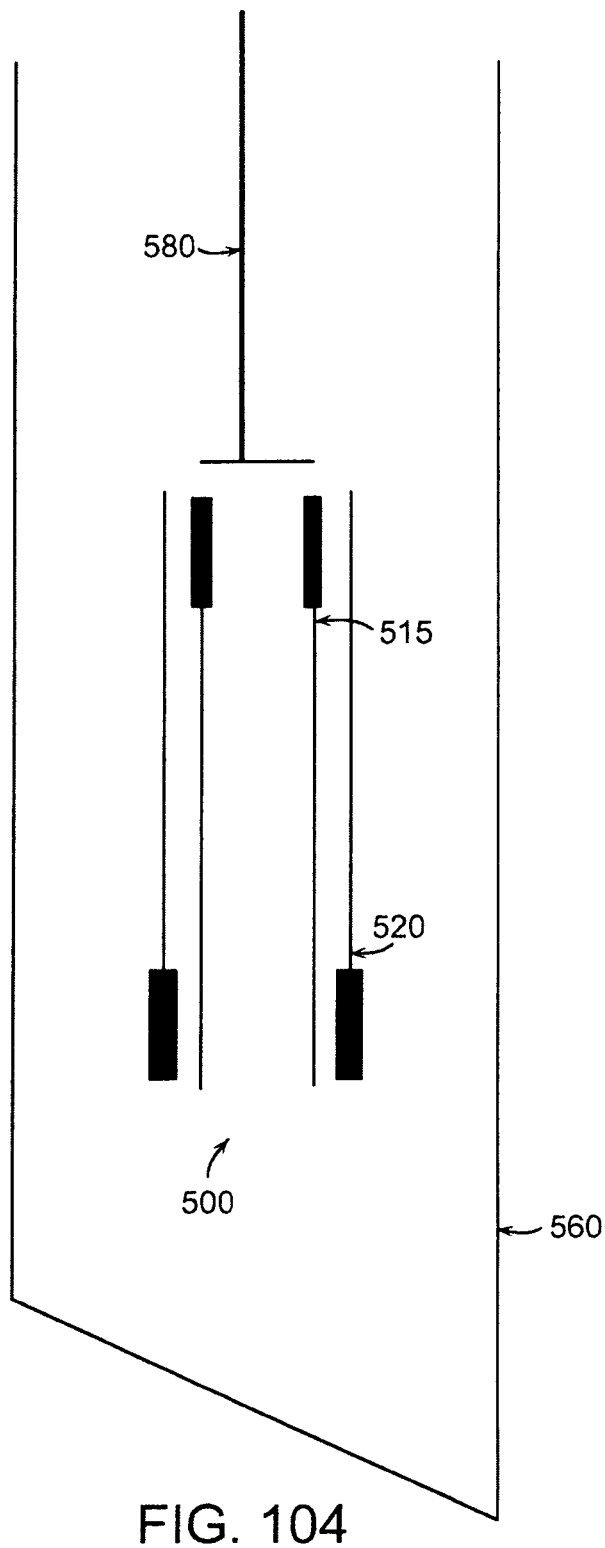
FIGS. 104-107 are schematic views showing another temporary occluder formed in accordance with the present invention.
Figure 105:
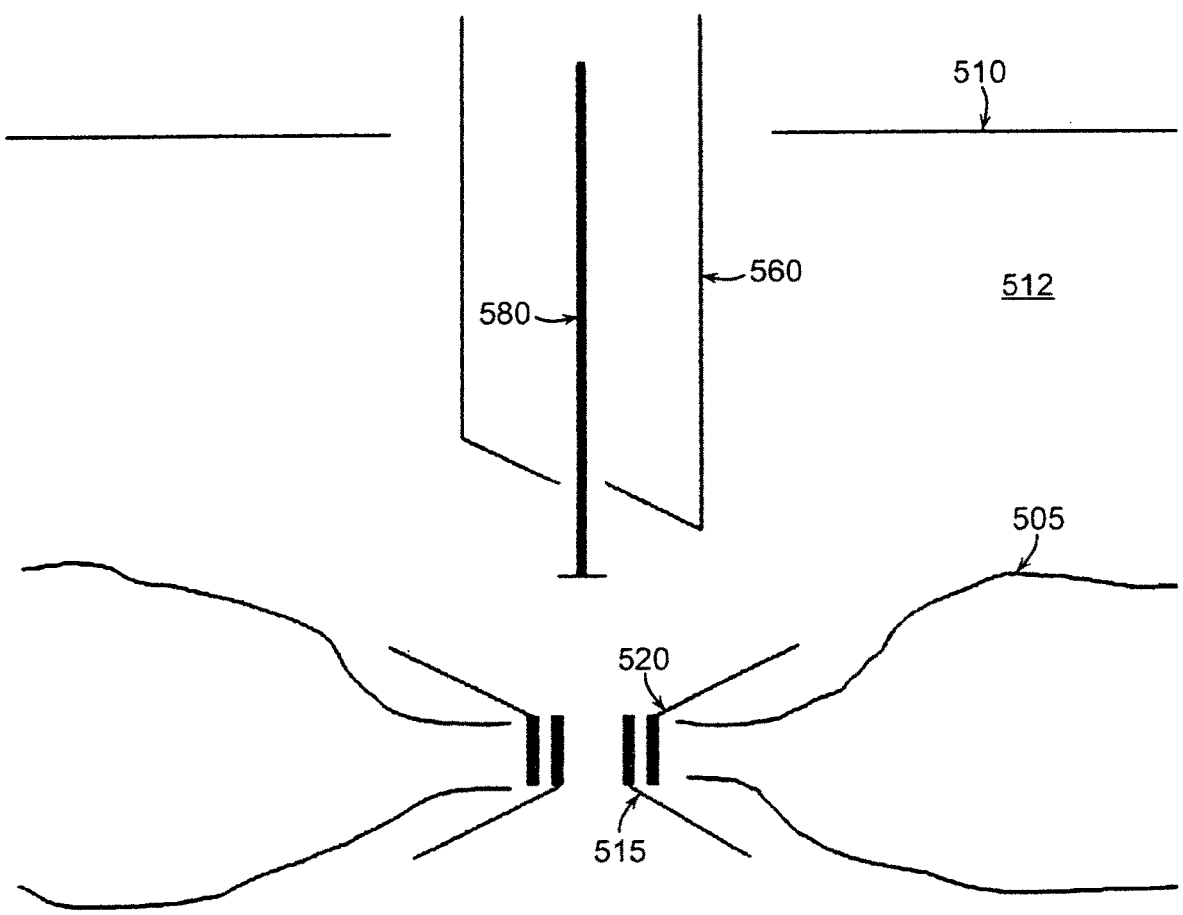
Figure 106:
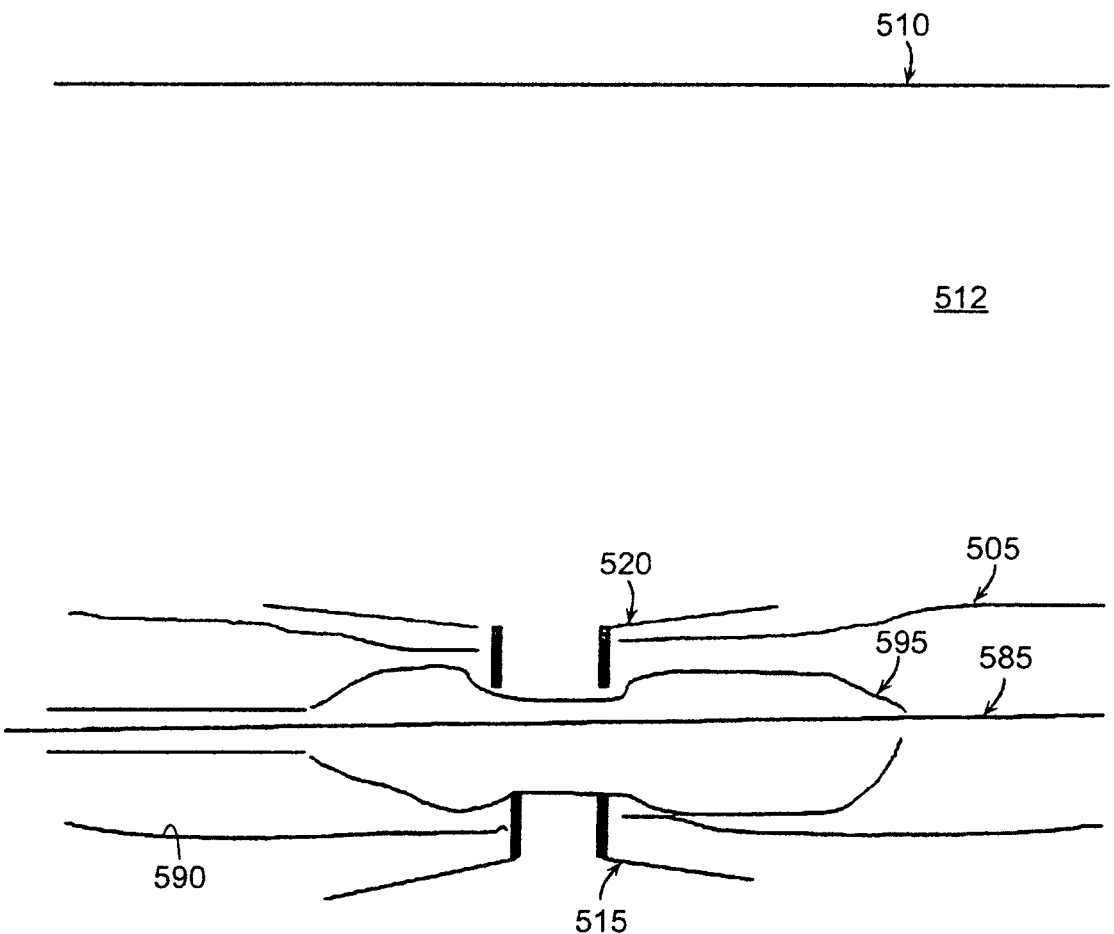

In another form of the invention, and looking now at FIGS. 104-107, temporary occluder 500 omits the aforementioned flexible filament 545, and instead provides an introducer 580 for deploying temporary occluder 500 out of needle 560 (FIGS. 104 and 105). However, in this form of the invention, introducer 580 is withdrawn with needle 560, leaving the deployed temporary occluder 500 isolated at the occlusion site.

Figure 107:
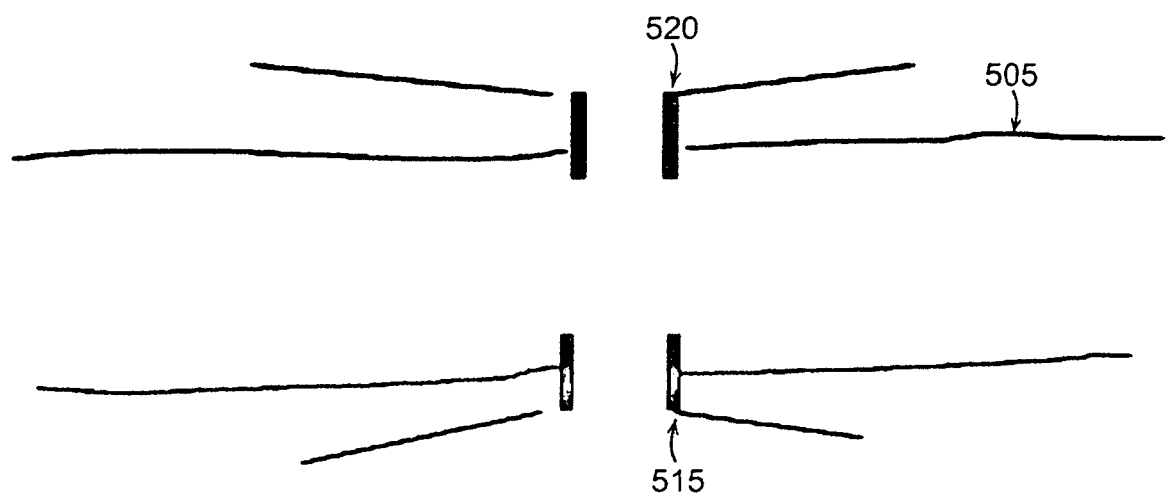

When occlusion of blood vessel 505 is no longer necessary, a guidewire 585 is passed down the lumen 590 of blood vessel 505 and through the deployed temporary occluder 500. Then an appropriately-sized, non-compliant balloon 595 (e.g., an angioplasty balloon) is advanced, in its deflated state, over guidewire 585 until balloon 595 spans temporary occluder 500. Then balloon 595 is expanded (FIG. 106) so as to separate distal portion 515 of temporary occluder 500 from proximal portion 520 of temporary occluder 500, thereby restoring normal blood flow through blood vessel 505. Finally balloon 595 and guidewire 585 are withdrawn (FIG. 107).

The balloon 595 may also be made out of an elastomer, e.g., latex or silicone. The balloon 595 may be filled with water or a compound of higher molecular weight than air. The balloon 595 may also be inflated with a polymer that hardens in situ, for applications where it is desirable to permanently maintain occlusion of the blood vessel. Alternatively, balloon 595 may be inflated with a polymer that hardens in situ and thereafter bio-degrades over time.

Figure 108:
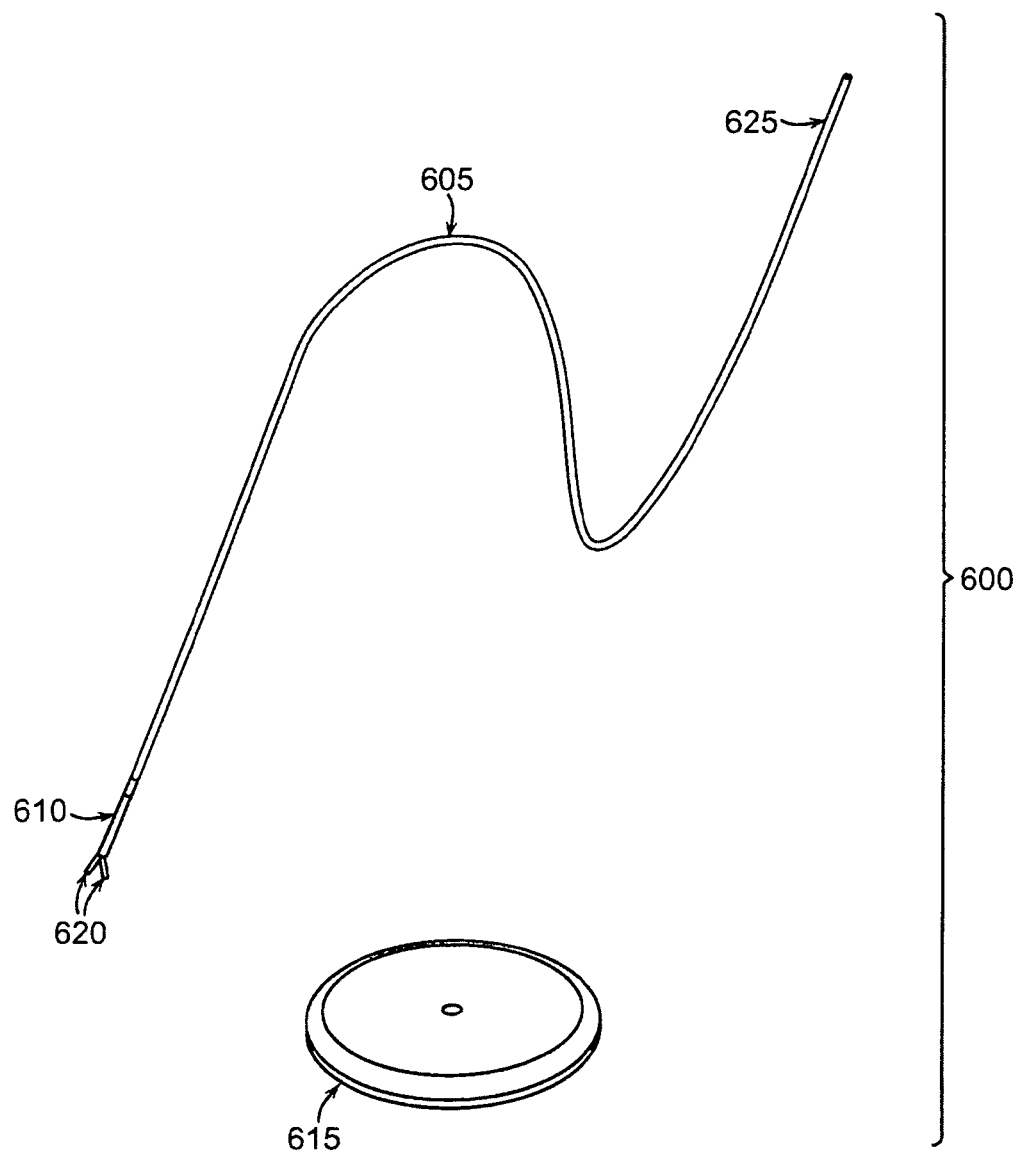
FIGS. 108-124 are schematic views showing still another temporary occluder formed in accordance with the present invention.

Looking next at FIG. 108, in another form of the invention, there is provided a temporary occluder 600. Temporary occluder 600 generally comprises a filament 605 having a distal portion 610 attached thereto, and a proximal portion 615. Distal portion 610 comprises a plurality of laterally-expanding legs 620 secured to distal portion 610.

Figure 109:
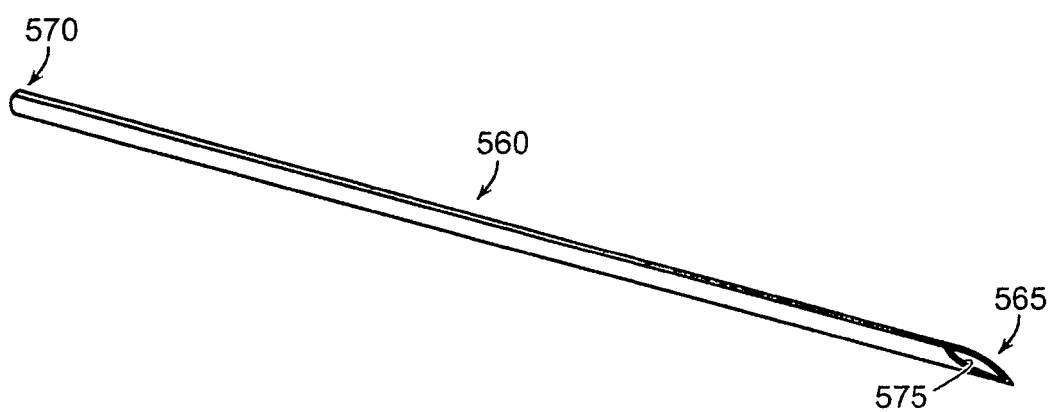

Temporary occluder 600 is intended to be deployed using a needle, e.g., the aforementioned needle 560 (FIG. 109).

Figure 110:
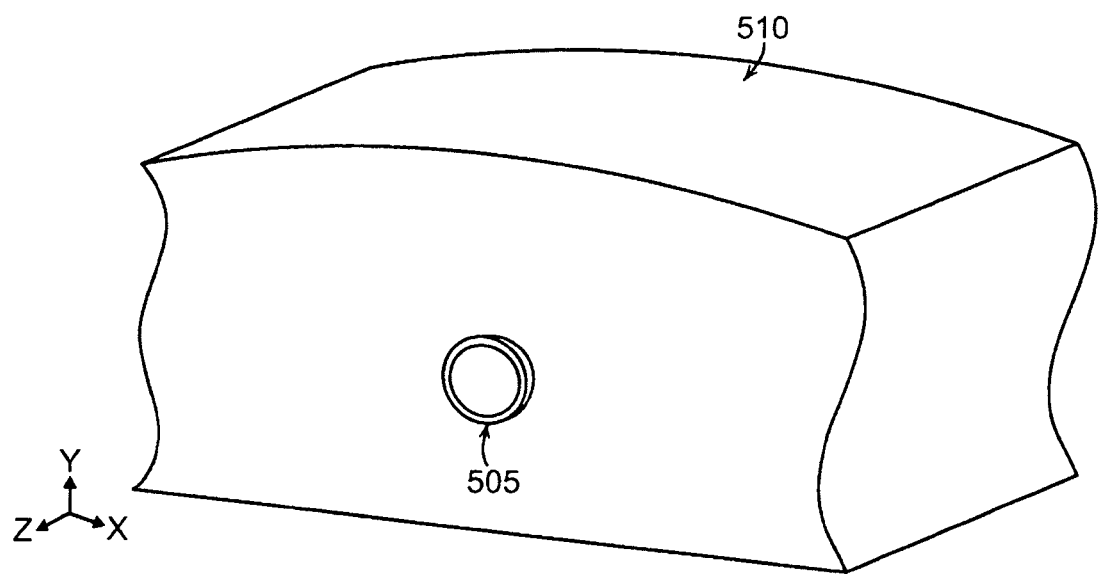
Figure 111:
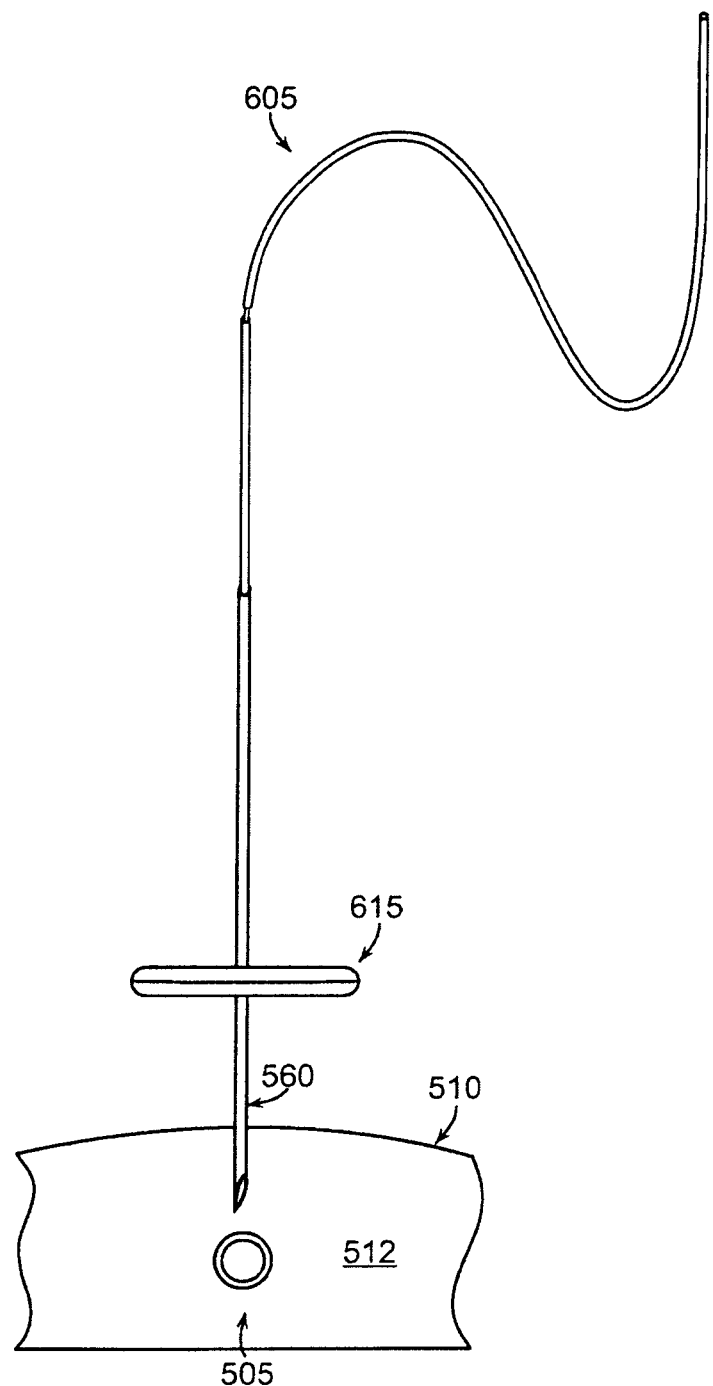
Figure 112:
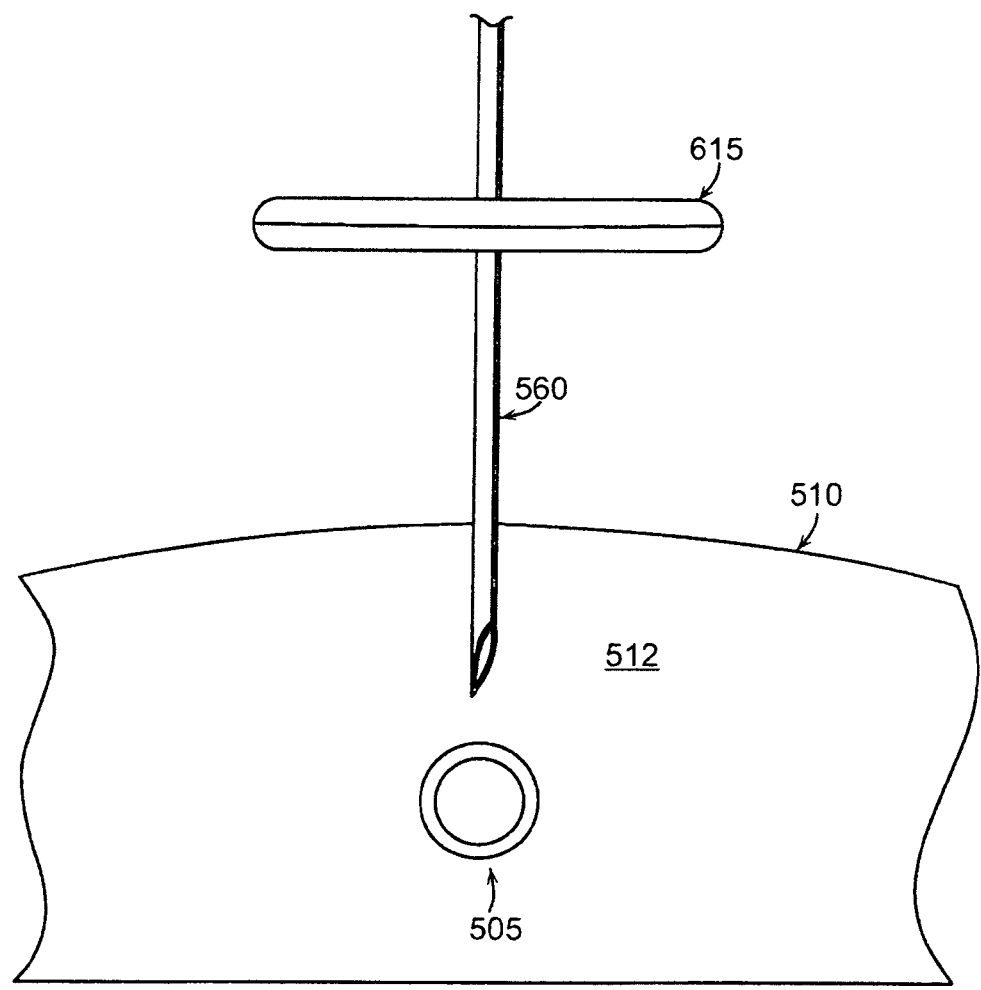
Figure 113:
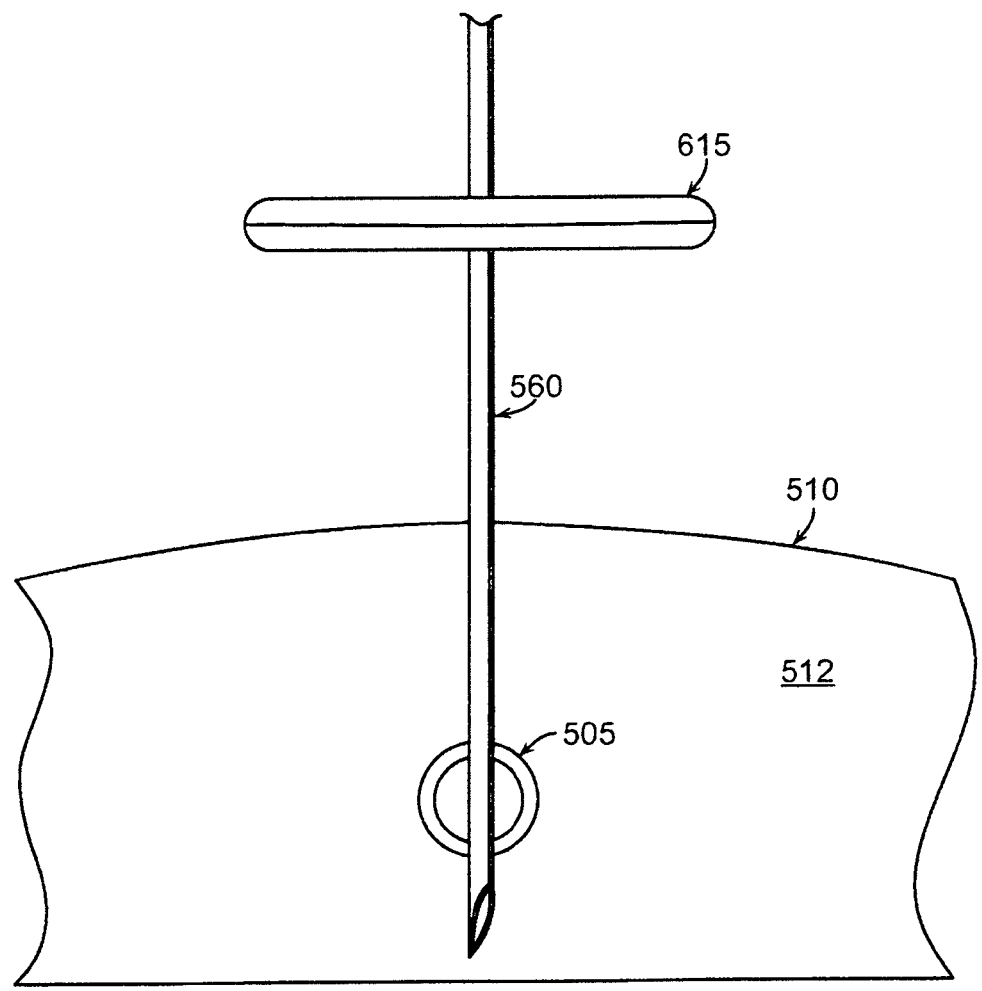
Figure 114:
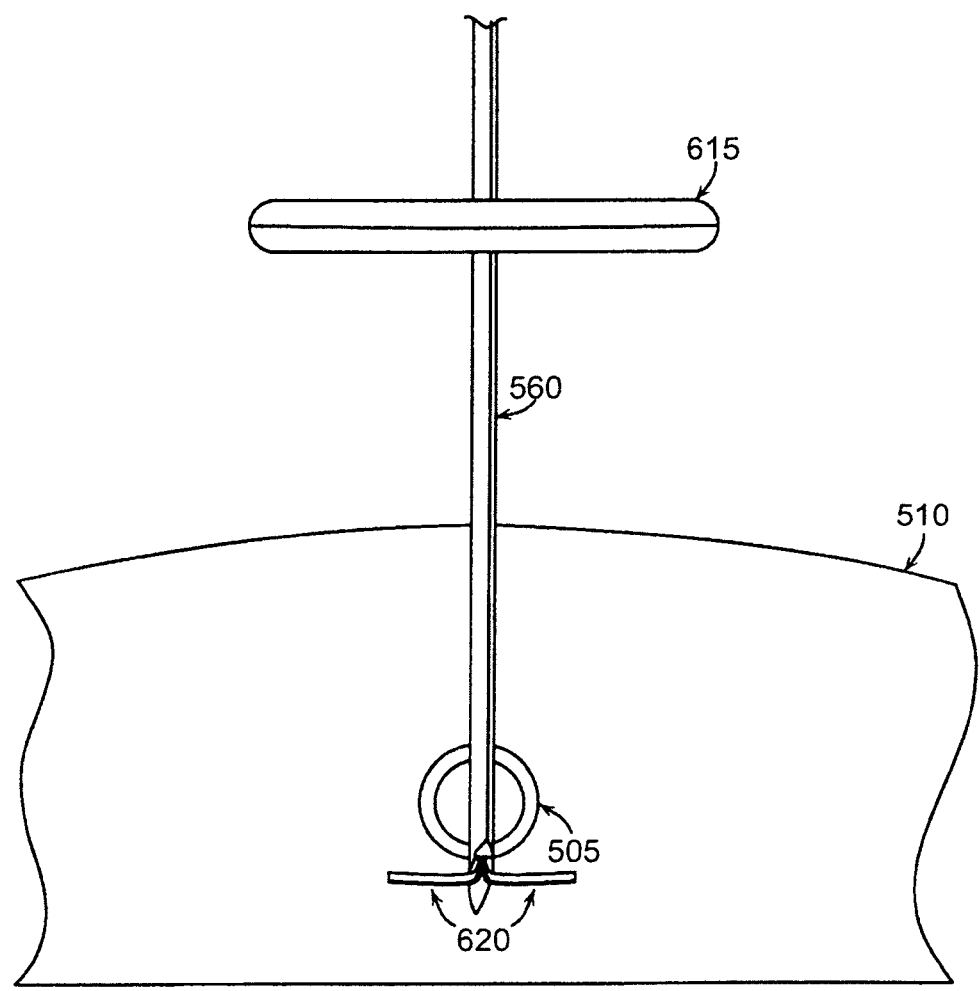
Figure 115:
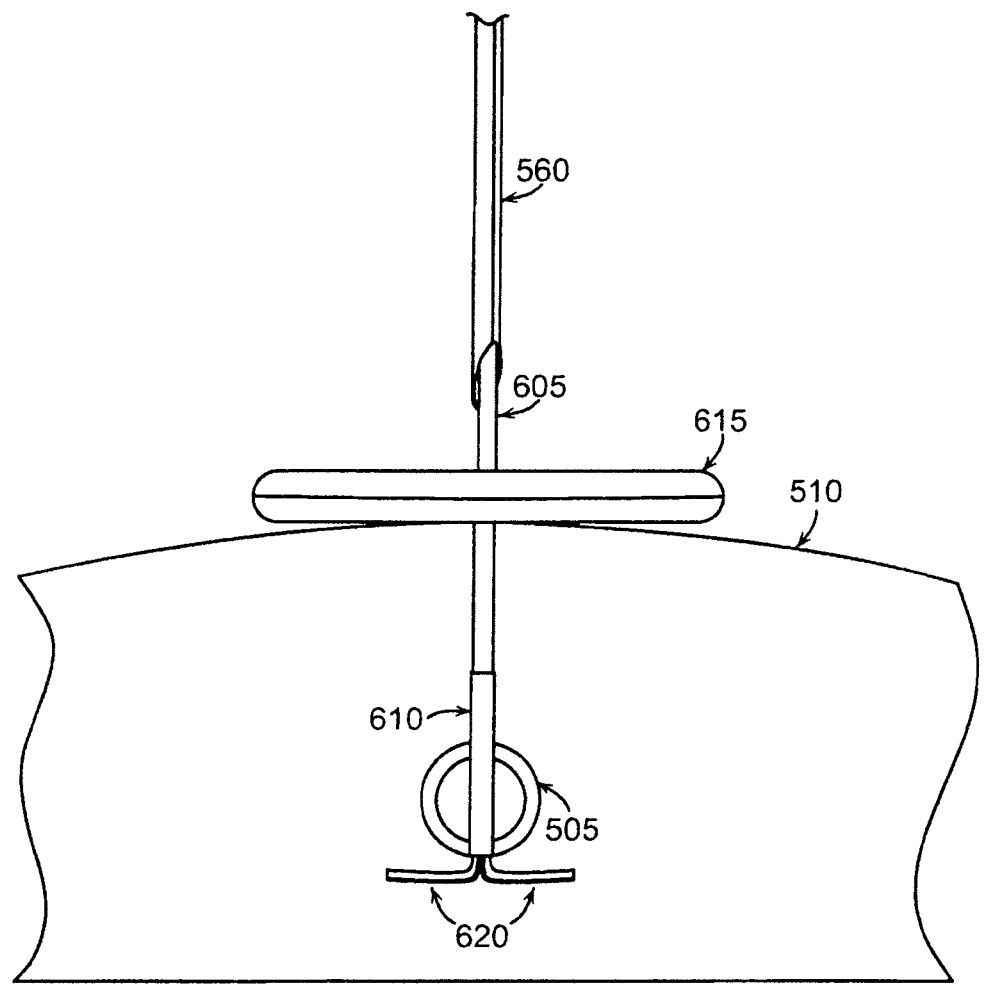
Figure 116:
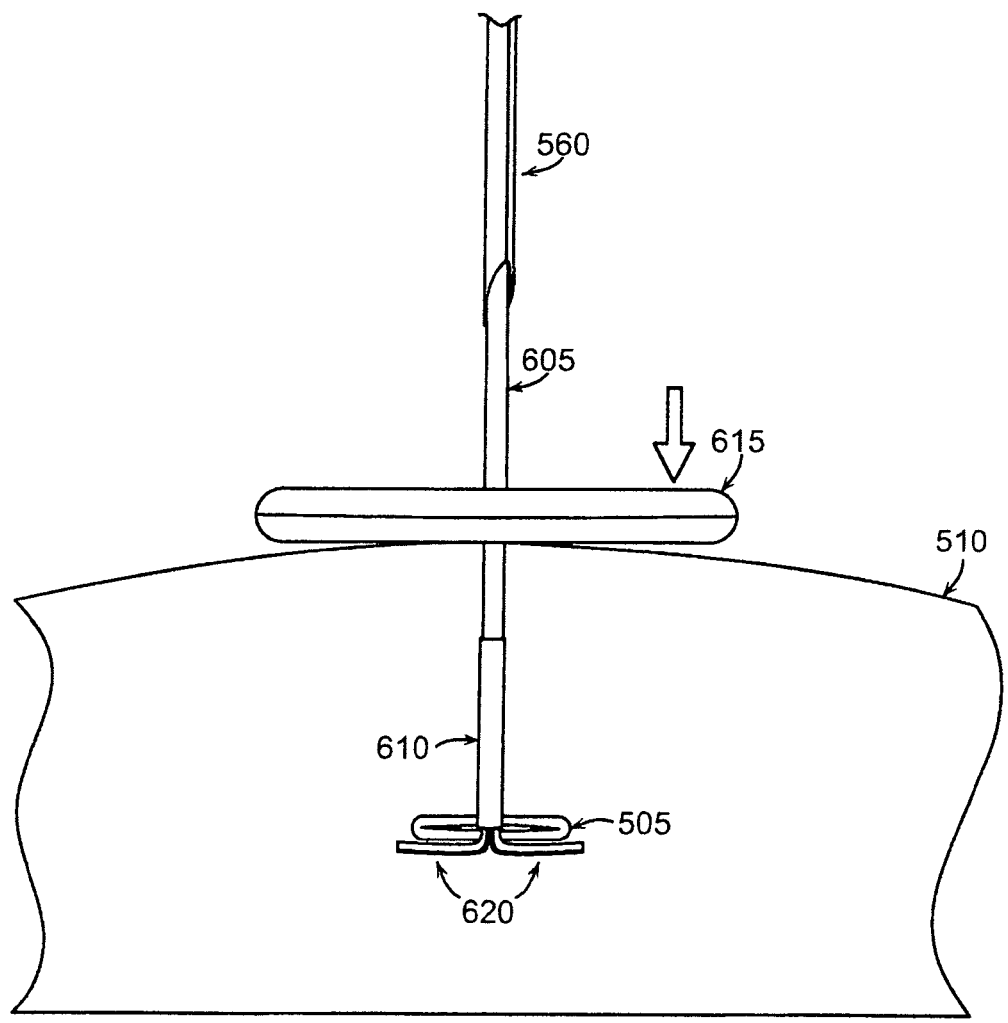
Figure 117:
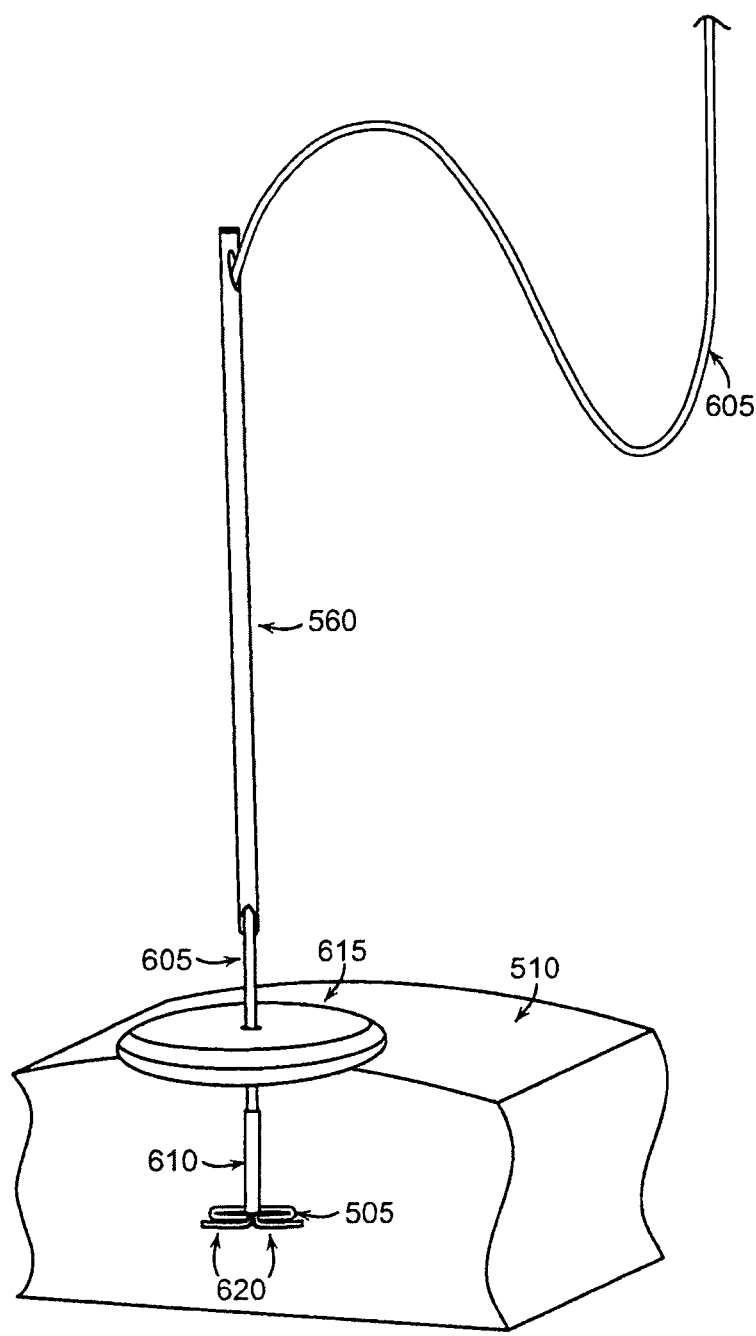
Figure 118:
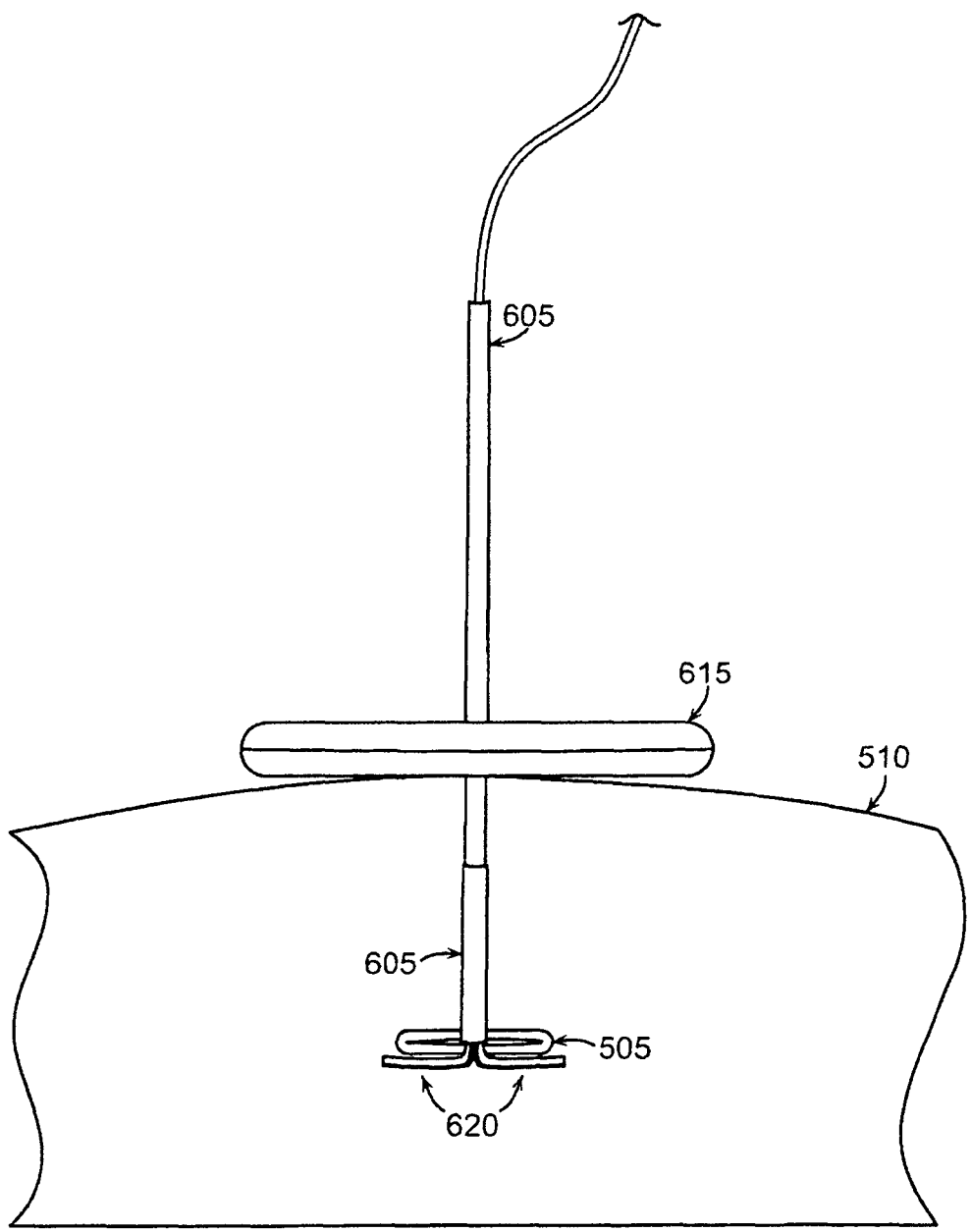
Figure 119:
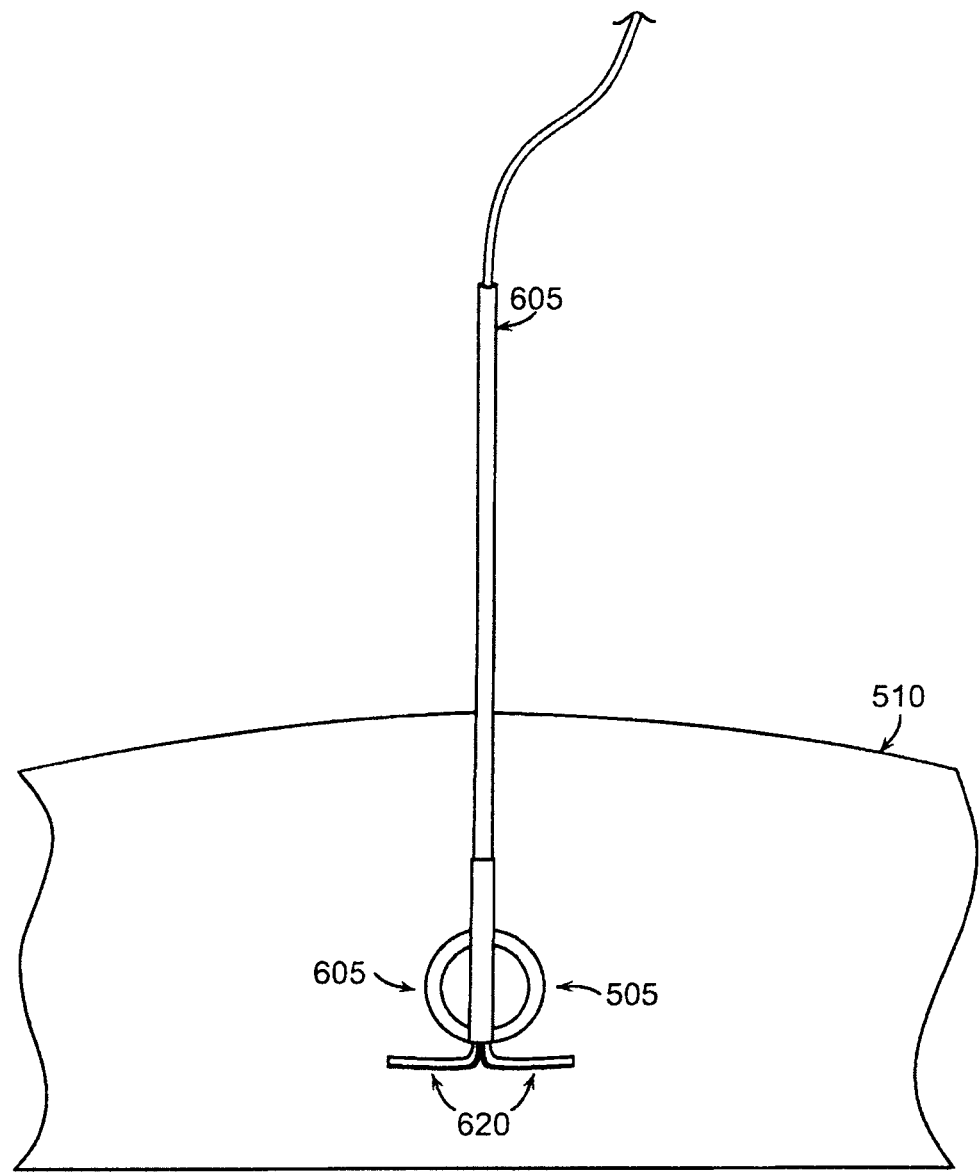
Figure 120:
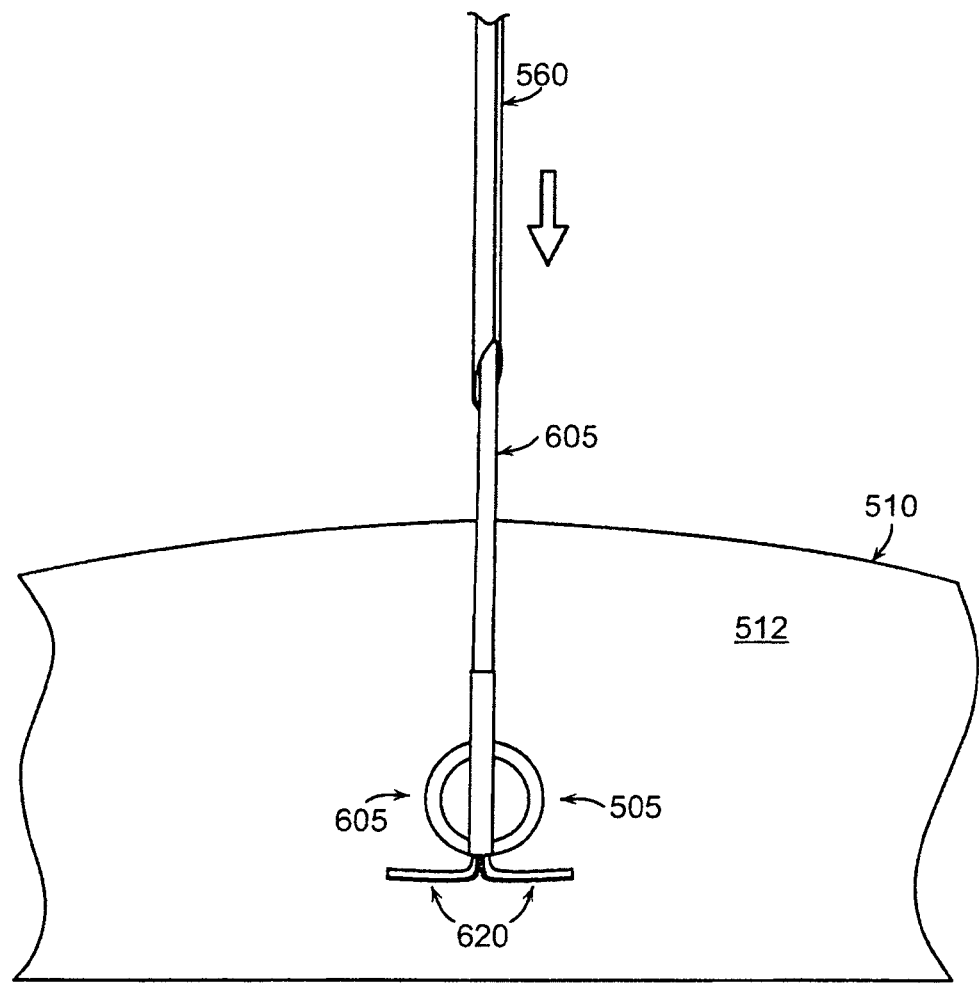
Figure 121:
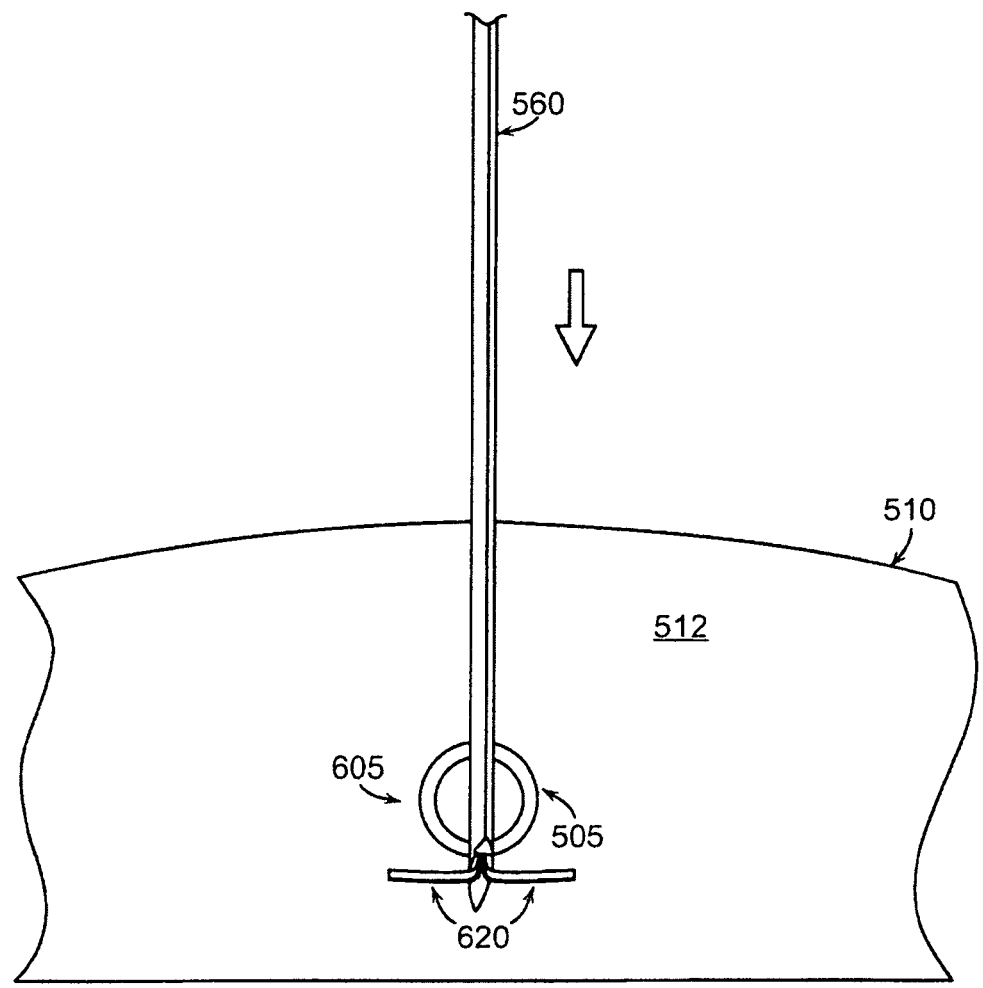
Figure 122:
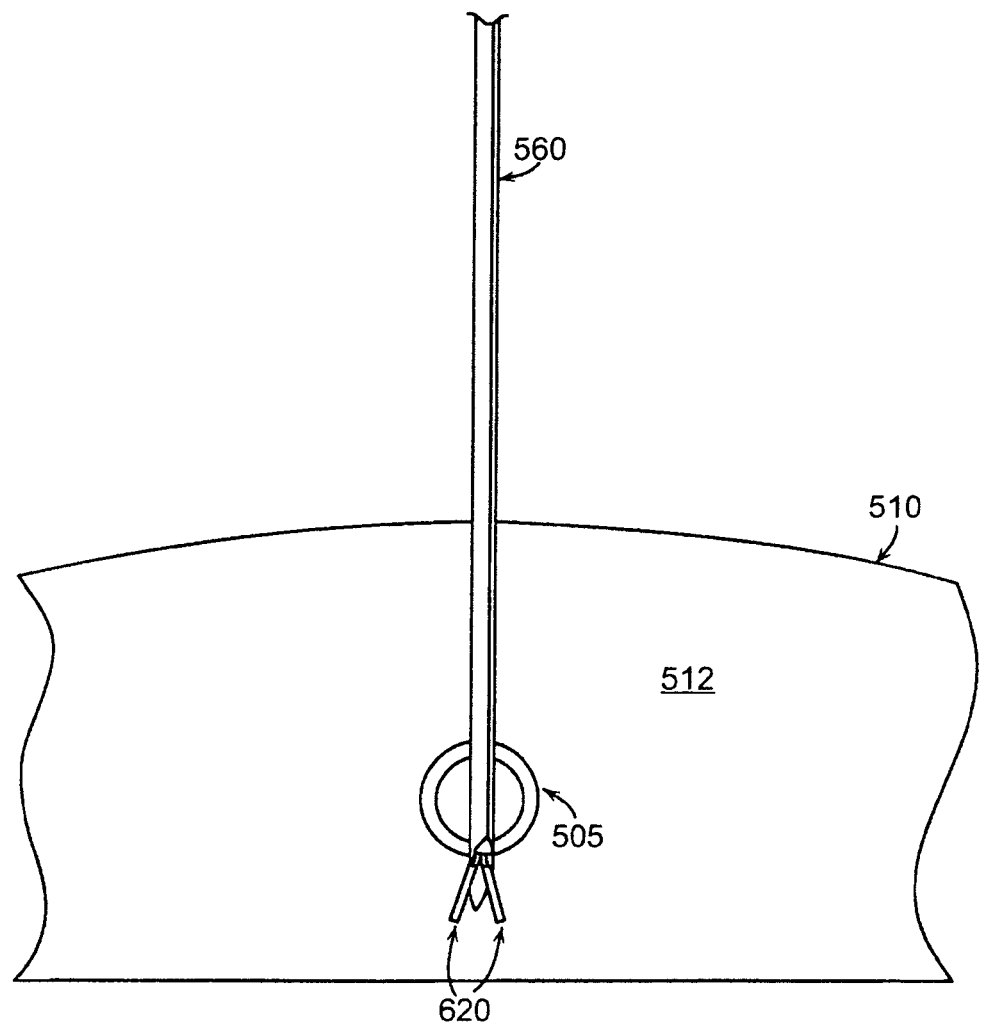
Figure 123:
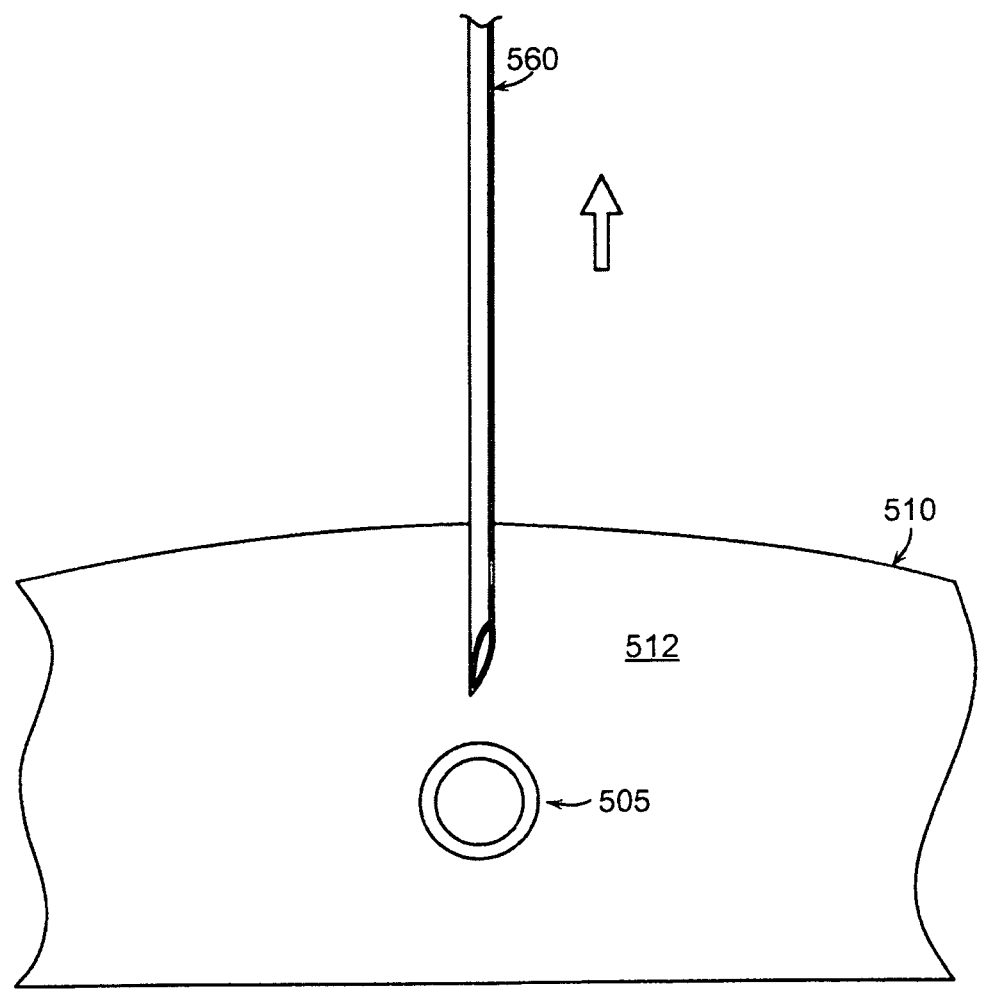

In use, and looking now at FIGS. 110-124, when blood vessel 505 is to be occluded (FIG. 110), filament 605 is loaded into lumen 575 of needle 560 so that distal portion 610 of temporary occluder 600 has its laterally-expanding legs 620 contained within distal end 565 of needle 560. This may be accomplished by feeding the proximal end 625 (FIG. 108) of filament 605 into distal end 565 of needle 560, advancing proximal end 625 of filament 605 out of proximal end 570 of needle 560, and then pulling on proximal end 625 of filament 605 so that laterally-expanding legs 620 are drawn into distal end 565 of needle 560. Then needle 560, carrying filament 605 and distal portion 610 therein, is advanced through skin 510 (FIG. 111), through intervening tissue 512 (FIG. 112) and then across the blood vessel 505 which is to be occluded, so that the distal end of needle 560 resides on the far side of the blood vessel (FIG. 113). Then filament 605 is advanced distally so that laterally-expanding legs 620 of distal portion 610 are pushed out of distal end 565 of needle 560, whereupon the laterally-expanding legs 620 expand (FIG. 114). Then needle 560 is retracted, and proximal portion 615 of temporary occluder 600 is advanced distally along needle 560 and filament 605 so that proximal portion 615 of temporary occluder 600 presses against the outer surface of the skin 510, whereby to compress blood vessel 505 and the intervening tissue 512 (FIGS. 115 and 116). Then proximal portion 615 of temporary occluder 600 is locked or secured in place (FIG. 117). At this point needle 560 may be completely withdrawn, leaving blood vessel 505 occluded (FIG. 118).

Figure 124:
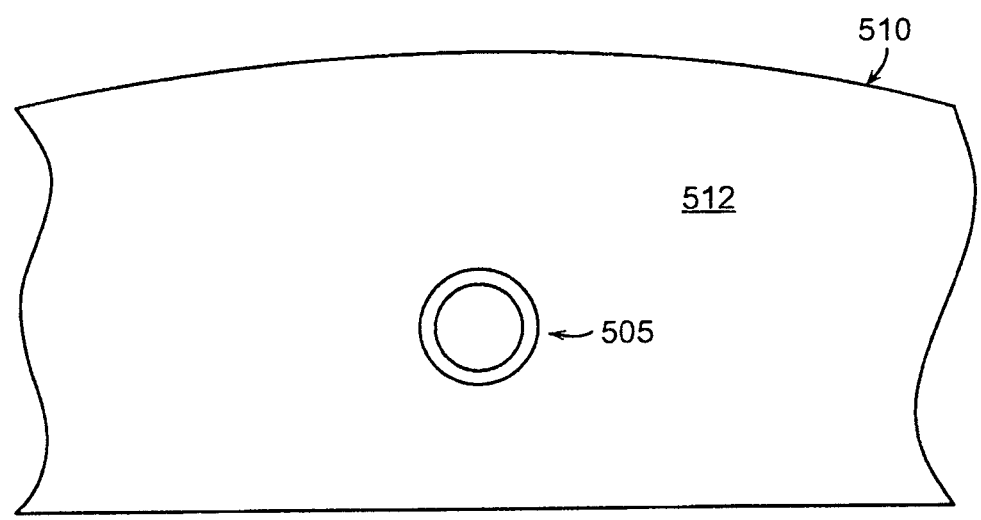

When occlusion is to be thereafter withdrawn, proximal portion 615 of temporary occluder 600 is removed (FIG. 119), needle 560 is advanced back down filament 605 (FIG. 120), through skin 510, through intervening tissue 512, through blood vessel 505 (FIG. 121) and then over laterally-expanding legs 620 (FIG. 122), causing laterally-expanding legs 620 to enter the interior of needle 560, collapsing laterally-expanding legs 512 in the process. Then needle 560 is withdrawn (FIG. 123), carrying filament 605 and distal portion 610 of temporary occluder 600 with it (FIG. 124).

Figure 125:
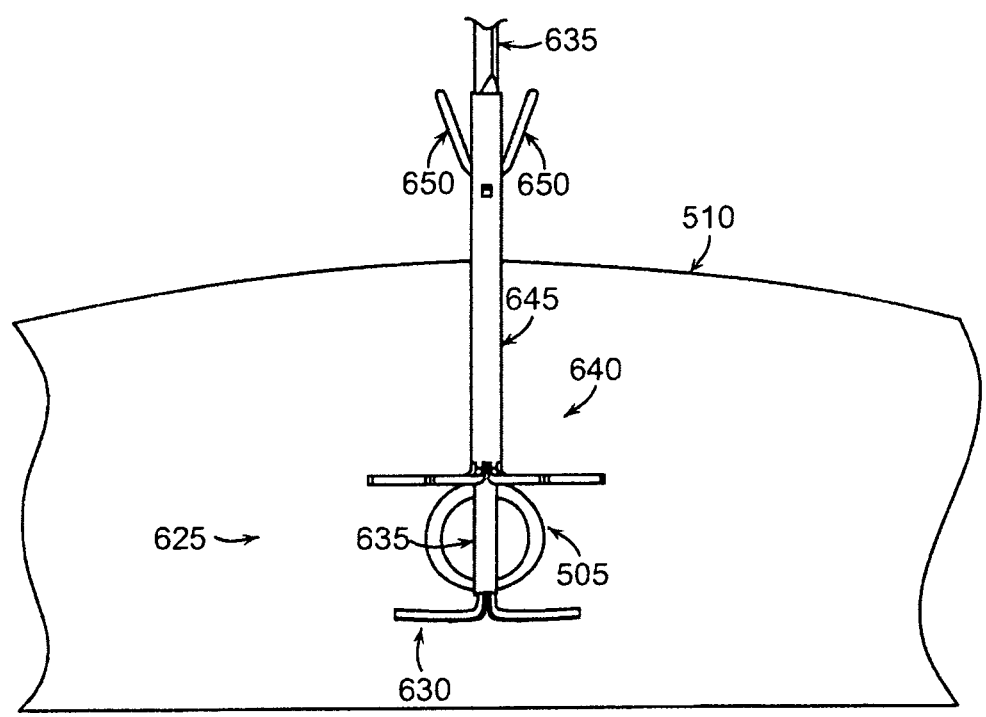
FIGS. 125 and 126 are schematic views showing yet another temporary occluder formed in accordance with the present invention.
Figure 126:
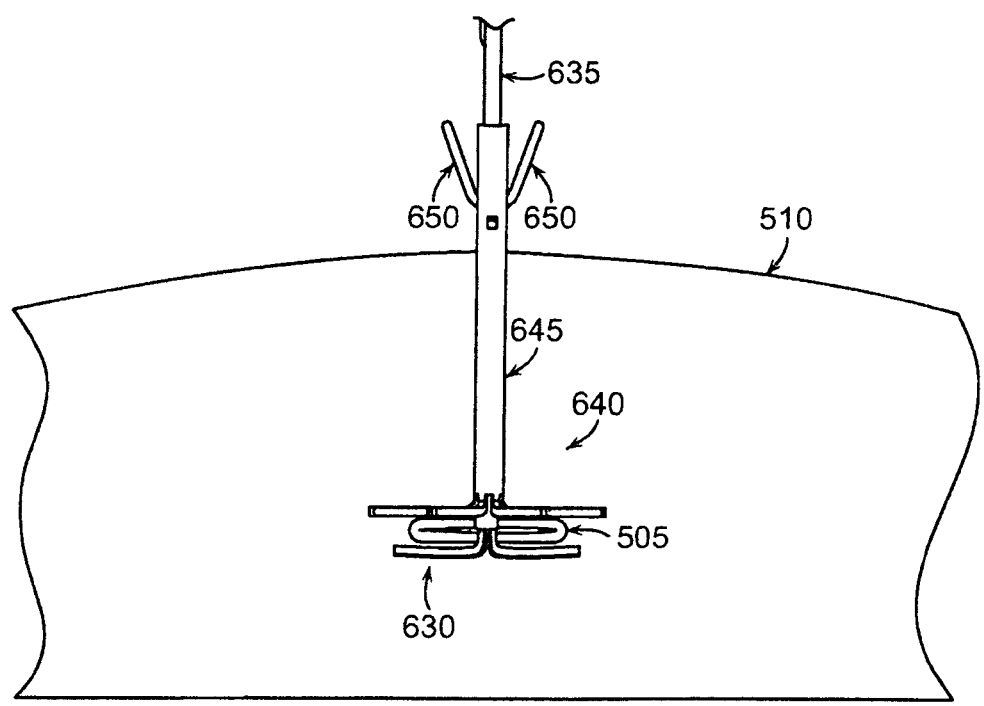

FIGS. 125 and 126 show a temporary occluder 625 which comprises another form of the invention. Temporary occluder 625 is substantially the same as the two-part occluder 200A shown in FIGS. 83-86, except that (i) temporary occluder 625 comprises a distal implant 630 having a distal implant body 635 of increased length sufficient to protrude above the surface of skin 510, and a proximal implant 640 having a proximal implant body 645 of increased length sufficient to protrude above the surface of skin 510, and (ii) temporary occluder 625 comprises fingers 650 on proximal implant body 645 allowing proximal implant 640 to be unlocked from distal implant 630 when desired.

FIG. 127 shows a temporary occluder 655 which comprises another form of the invention. Temporary occluder 655 is substantially the same as the two-part occluder 200A shown in FIGS. 83-86, i.e., it comprises a distal implant 660 and a proximal implant 665, etc., except that in this form of the invention, the proximal end of distal implant 660 is threaded (not shown) as will hereinafter be discussed.

Figure 128:
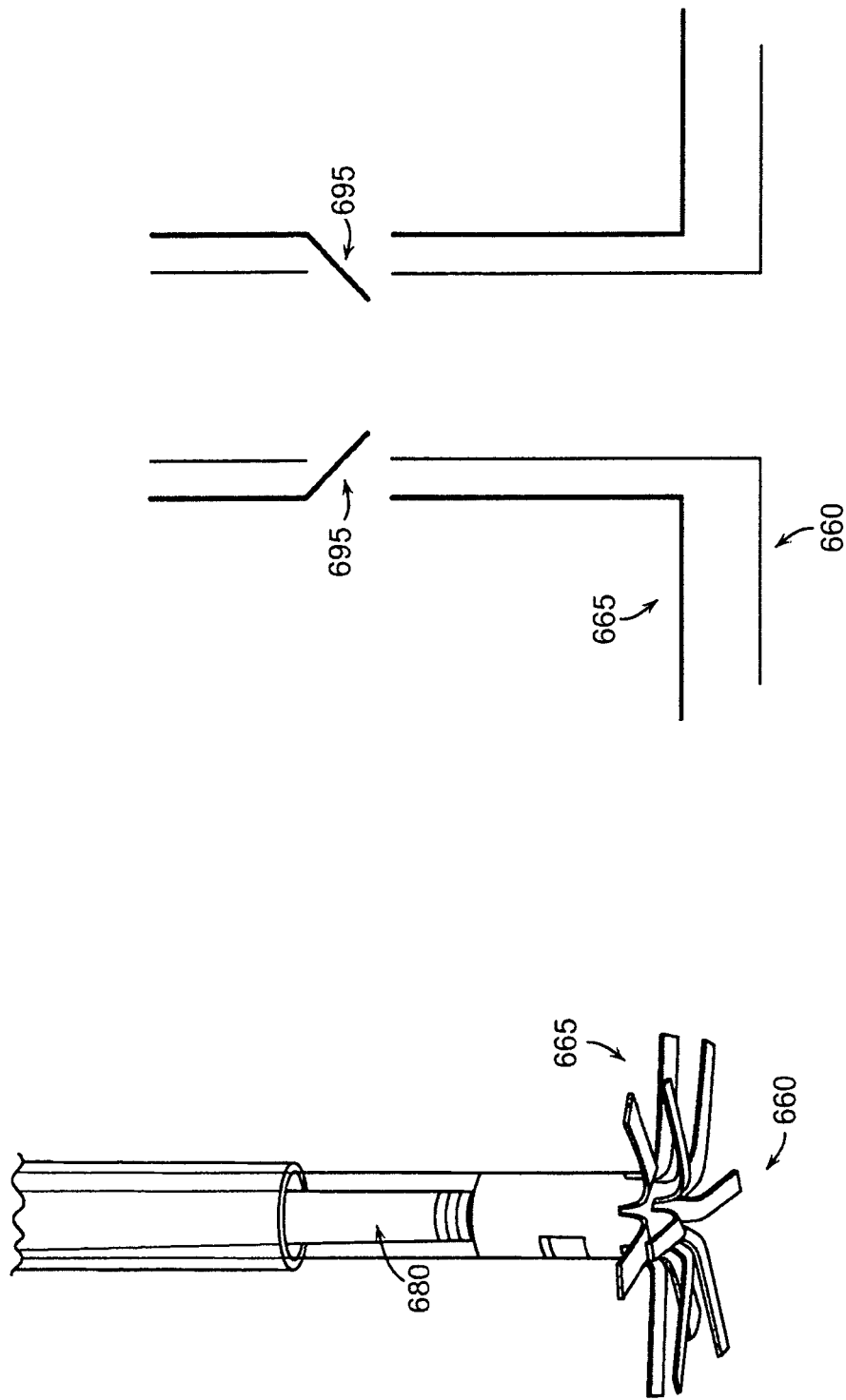
Figure 130:
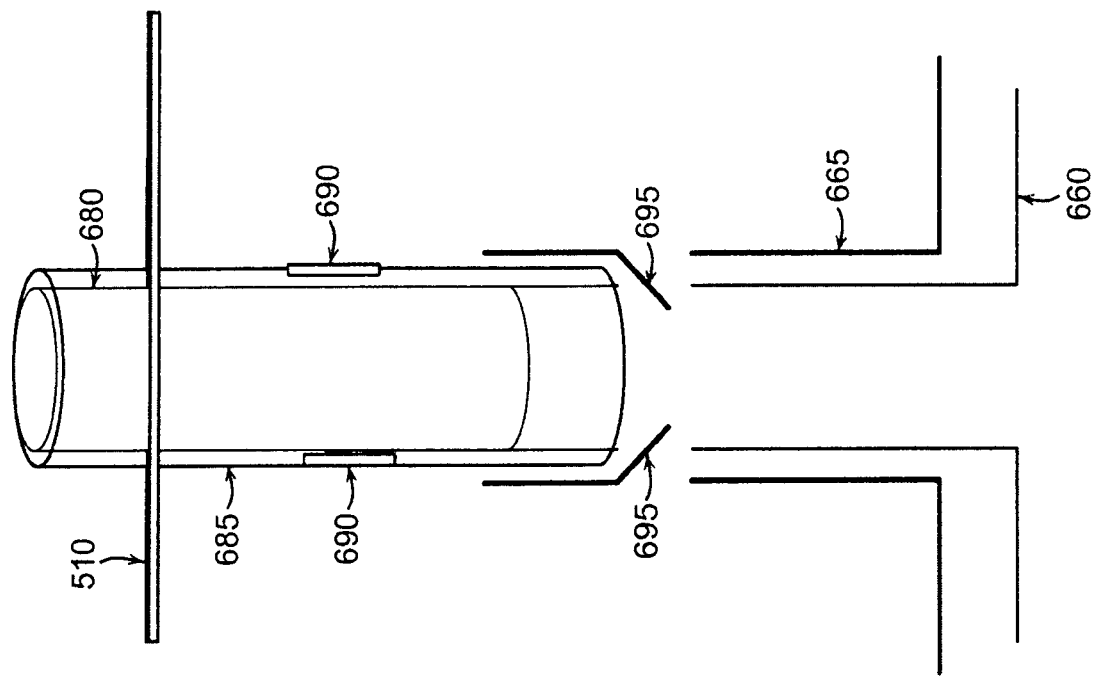
Figure 129:
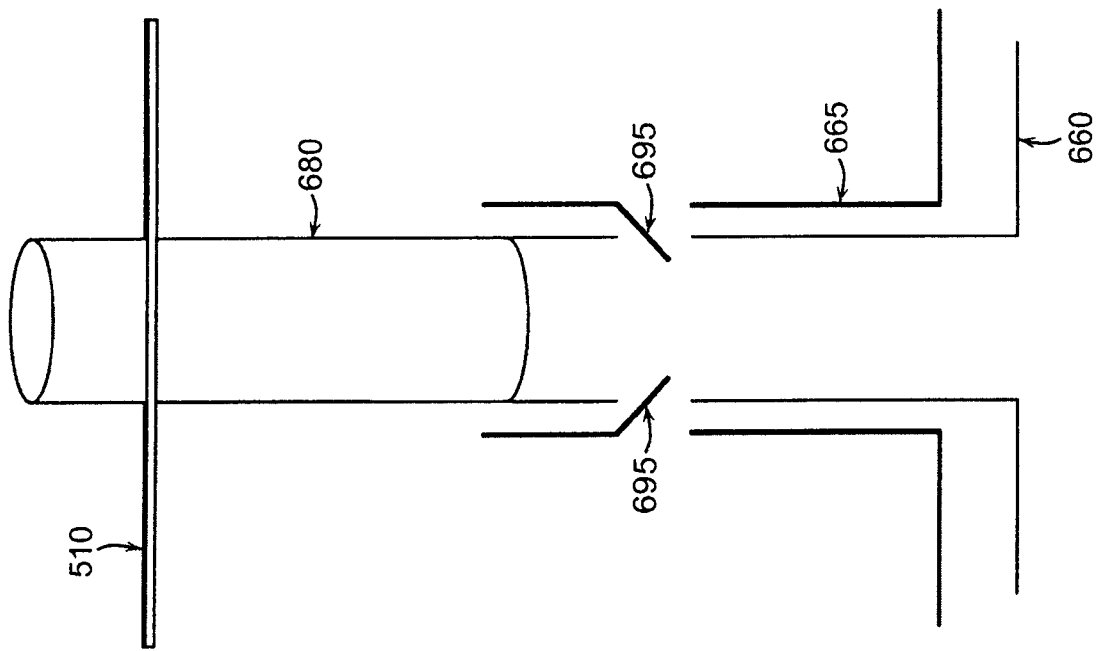
Figure 133:
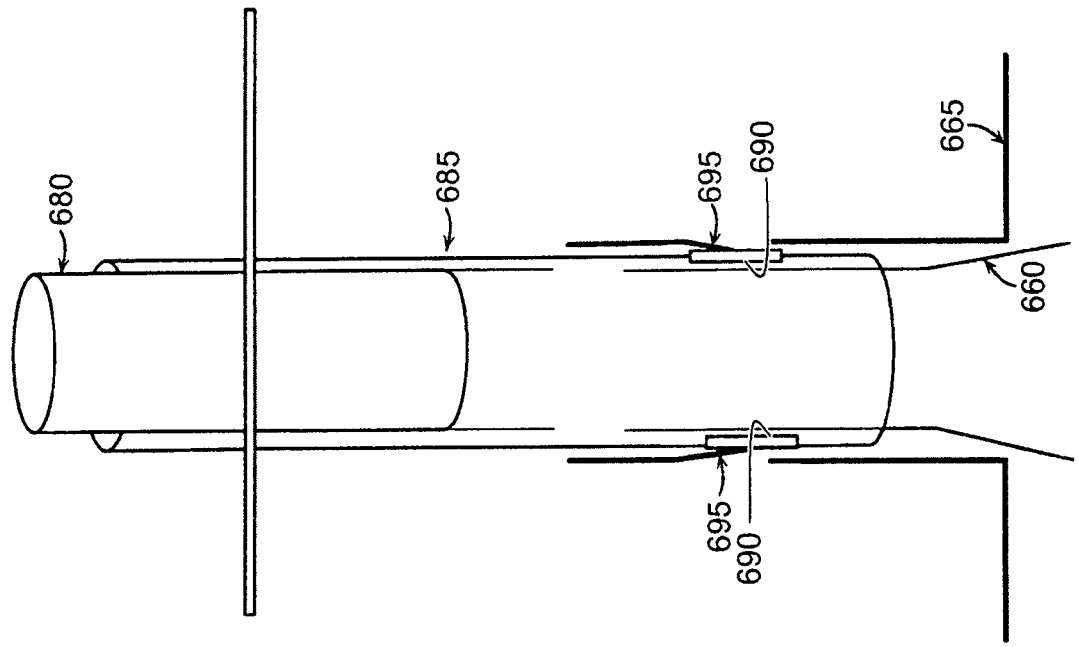
Figure 134:
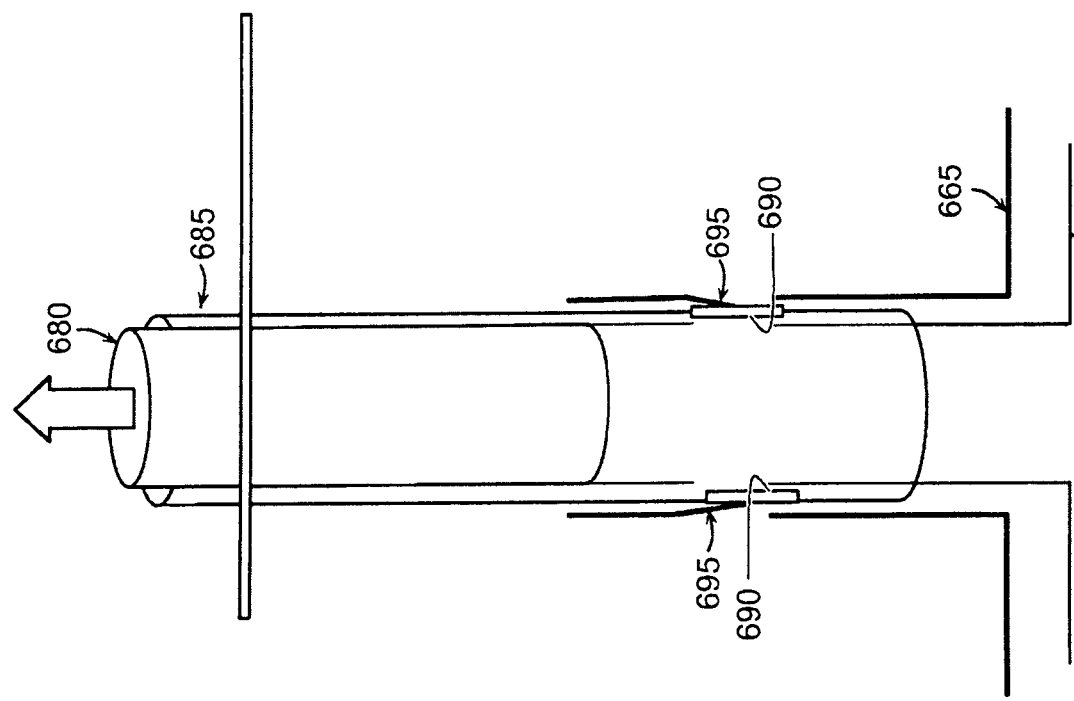
Figures 135, 136:
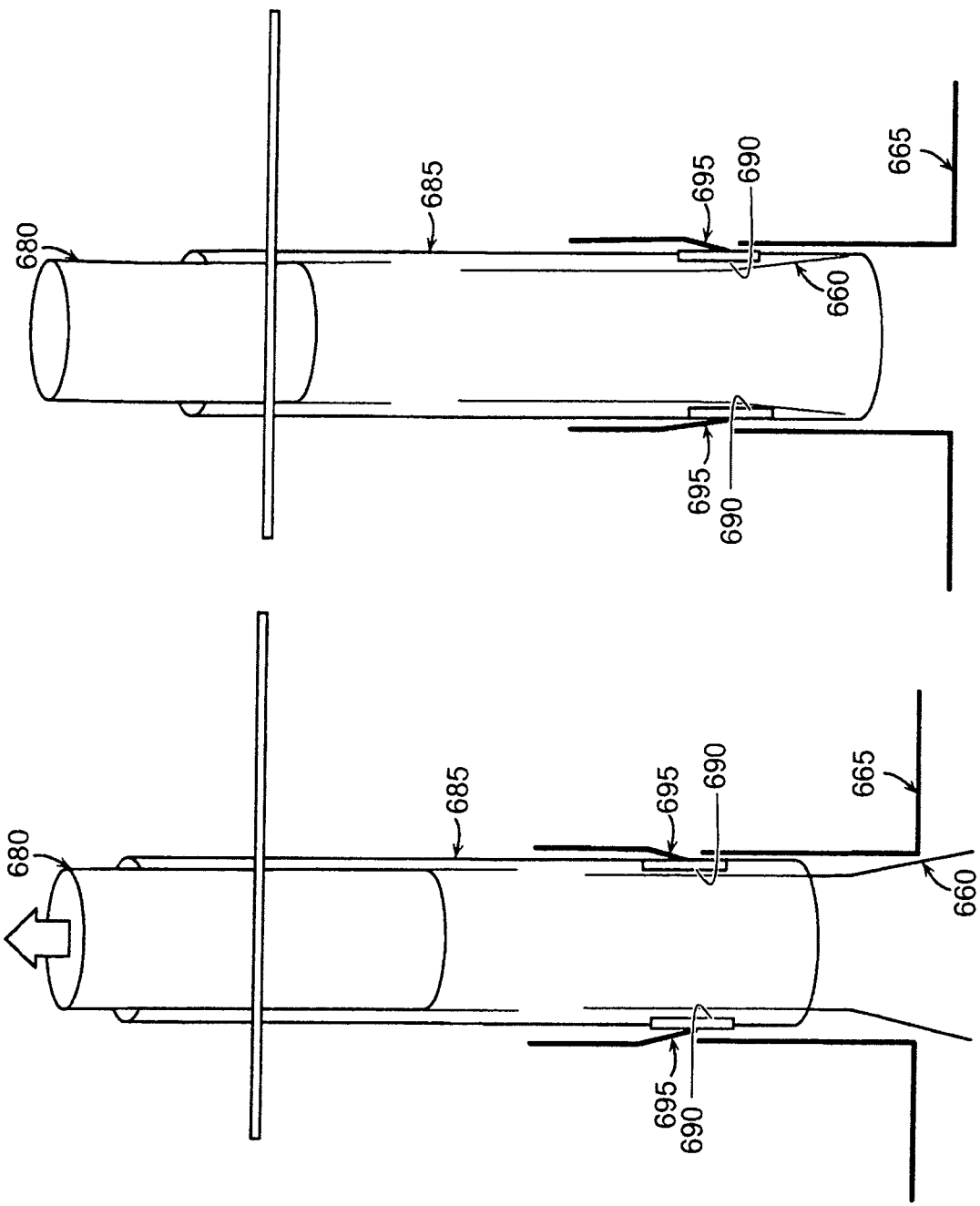
Figure 138:
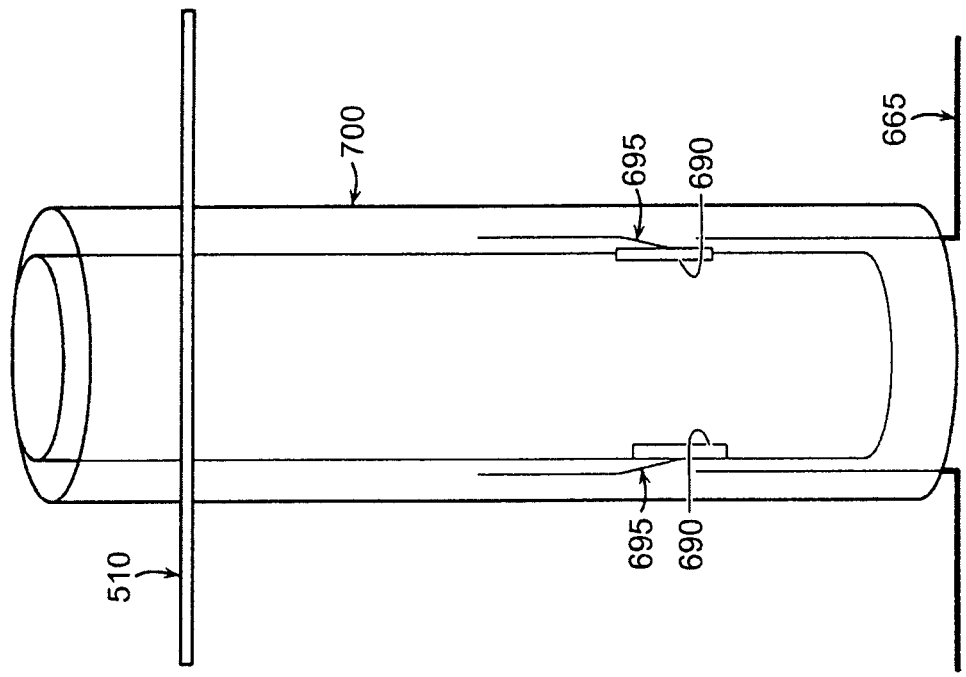
Figure 137:
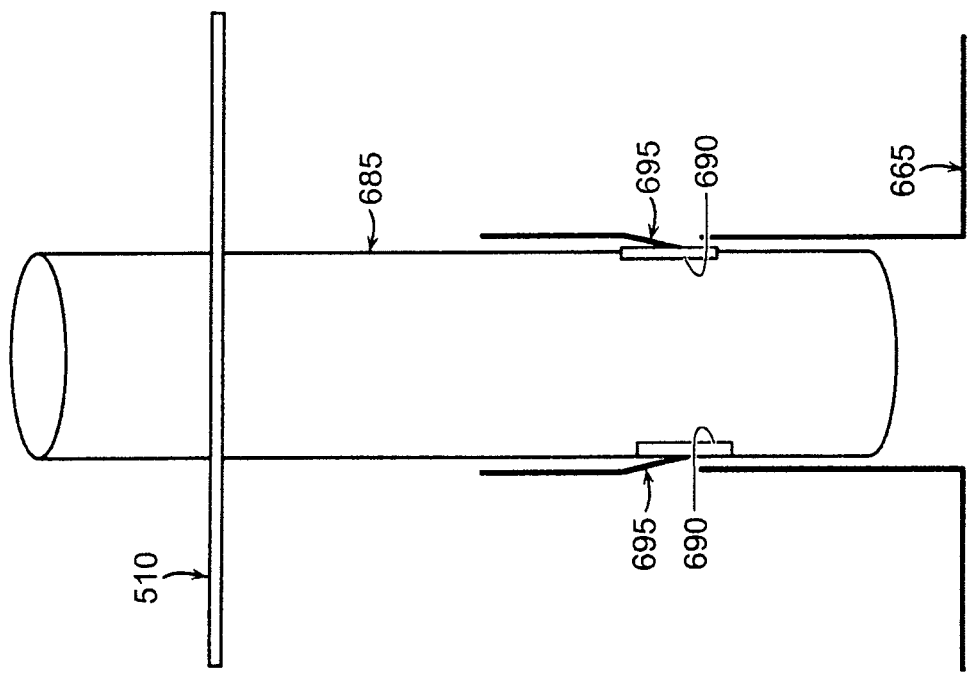
Figure 140:
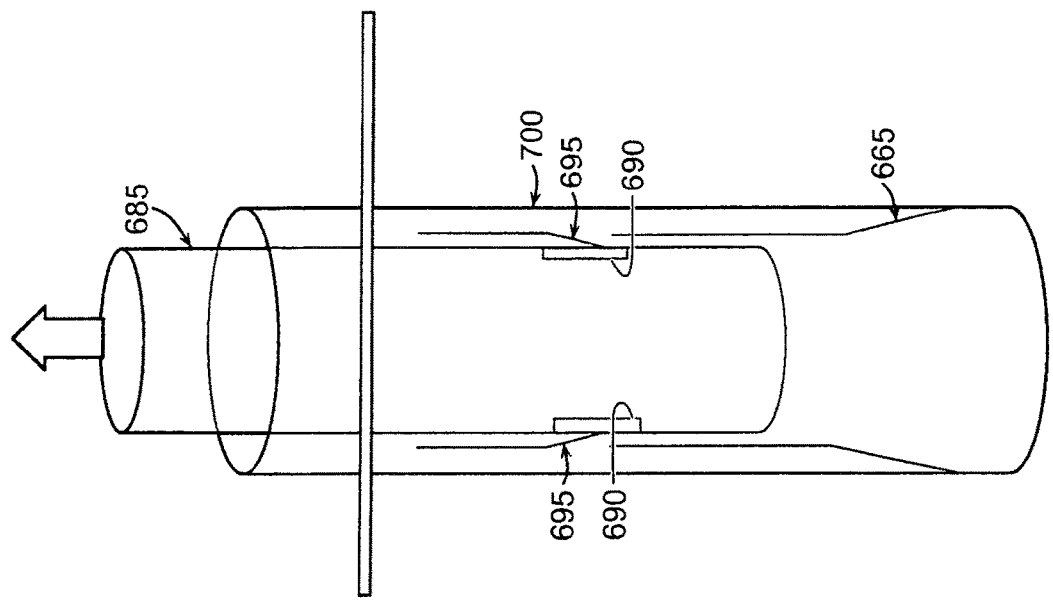
Figure 139:
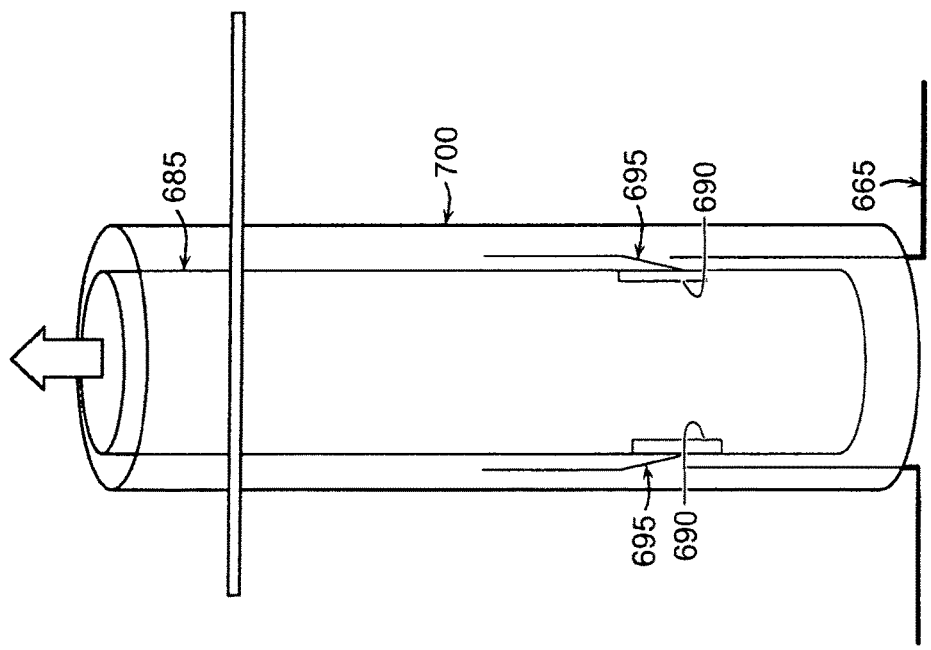
Figure 142:
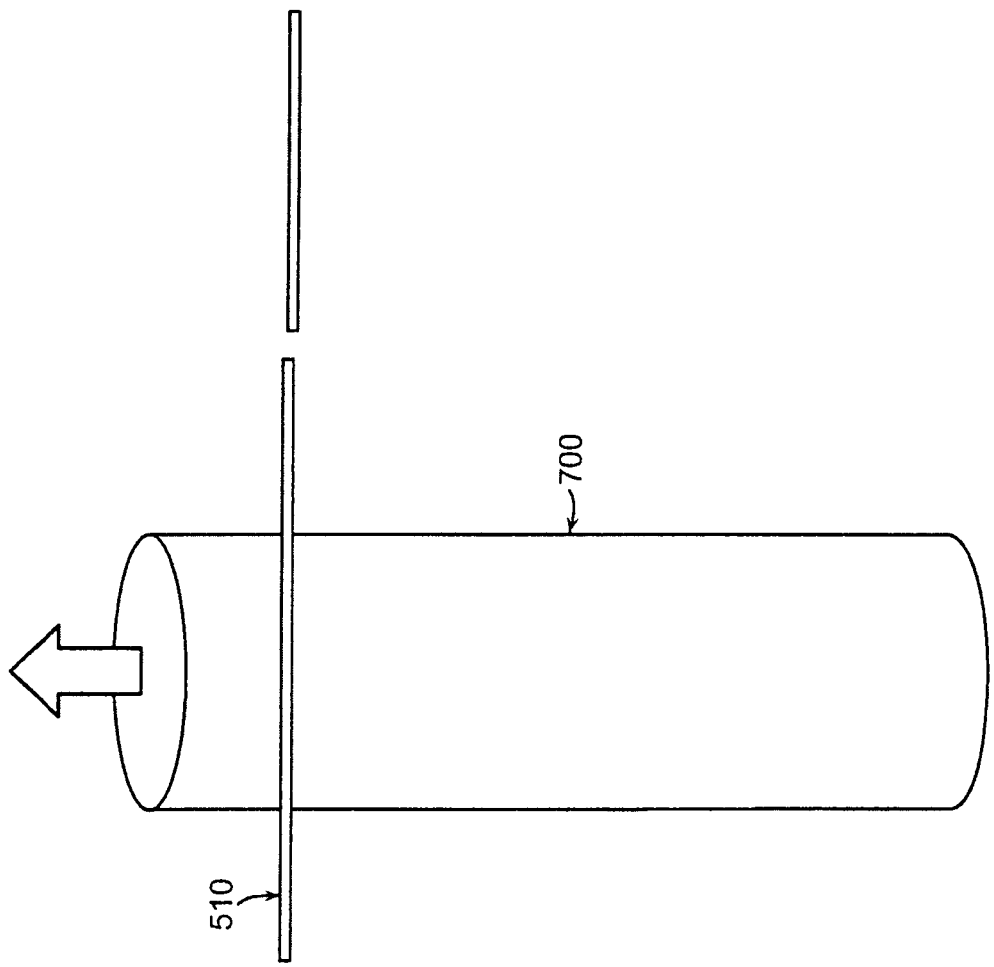
Figure 141:
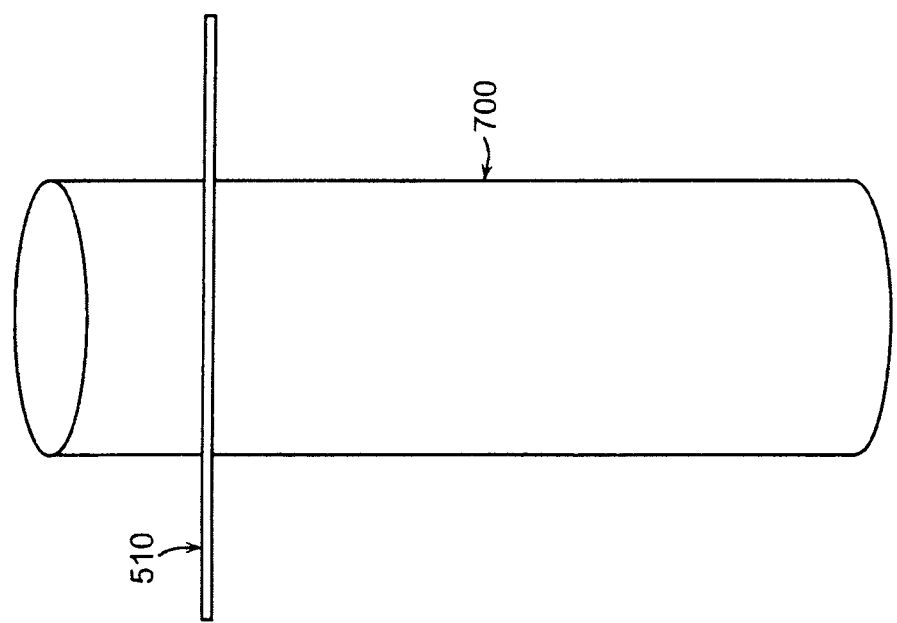

In this form of the invention, when temporary occluder 655 is to be removed from the patient, a removal device 670 is advanced through skin 510 and intervening tissue 512 until the distal tip 675 of removal device 670 contacts the proximal end of proximal implant 665 (FIG. 128). Ultrasound guidance may be used to facilitate such docking. Then a shaft 680 is extended out of removal device 670 and threaded into distal implant 660 (FIGS. 128 and 129). Next, a pusher tube 685 is advanced over shaft 680 and unlatches proximal implant 665 from distal implant 660 (FIGS. 130 and 131). Pusher tube 685 itself latches onto proximal implant 665 using latching grooves 690 formed in pusher tube 685, which receive latches 695 of proximal implant 665 (FIG. 132) so as to effect the desired connection. Then shaft 680 is pulled proximally, pulling distal implant 660 through pusher tube 685 and out of the patient (FIGS. 133-137). Next, an external sheath 700 is extended down over pusher tube 685 (FIG. 138) whereby to capture proximal implant 665, within the external sheath, whereupon proximal implant 665 is removed from the surgical site by pulling pusher tube 685 out of the patient through external sheath 700 (FIGS. 139 and 140). Finally, external sheath 700 is removed from the patient (FIGS. 141 and 142). It should also be appreciated that various other means of attachment and securing the various elements will be apparent to those skilled in the art in view of the present disclosure.

Figure 143:
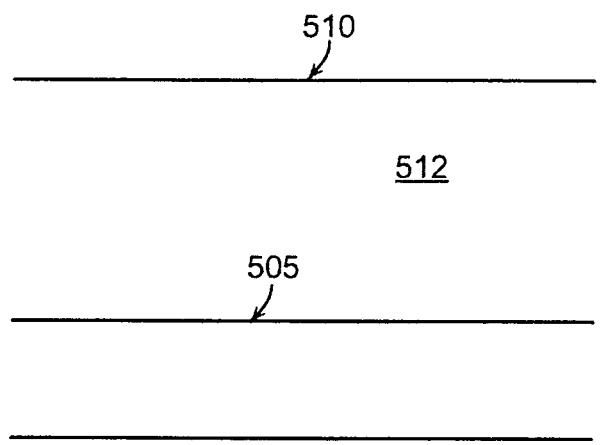
FIGS. 143-148 are schematic views showing still another temporary occluder formed in accordance with the present invention.
Figure 144:
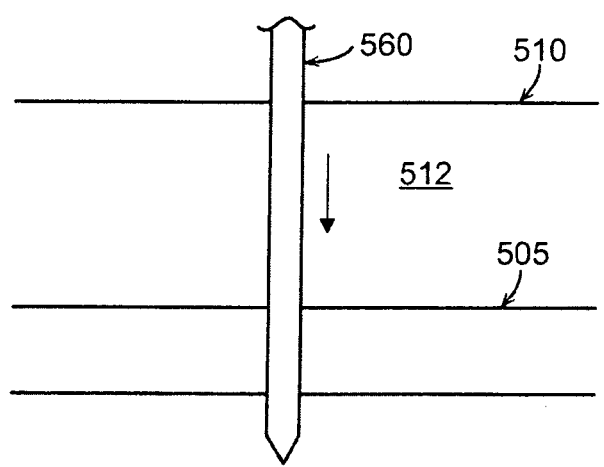
Figure 145:
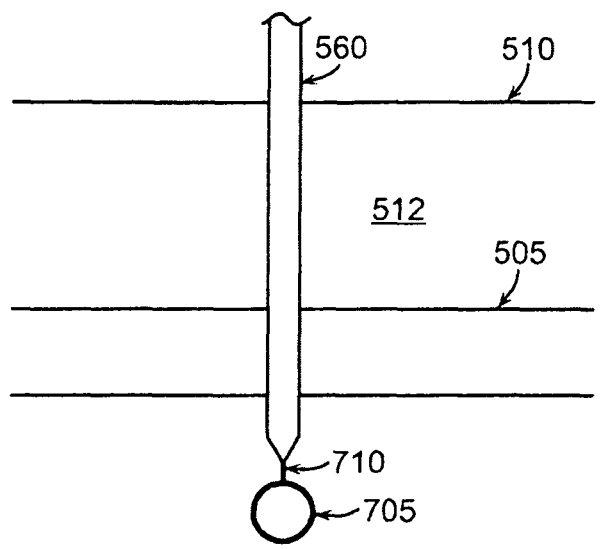
Figure 146:
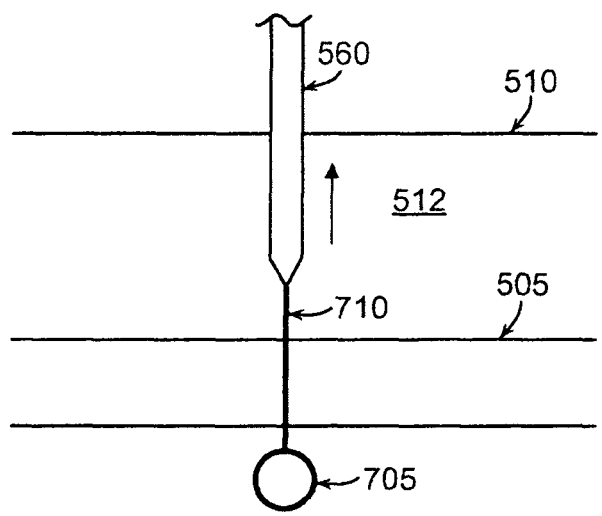
Figure 147:
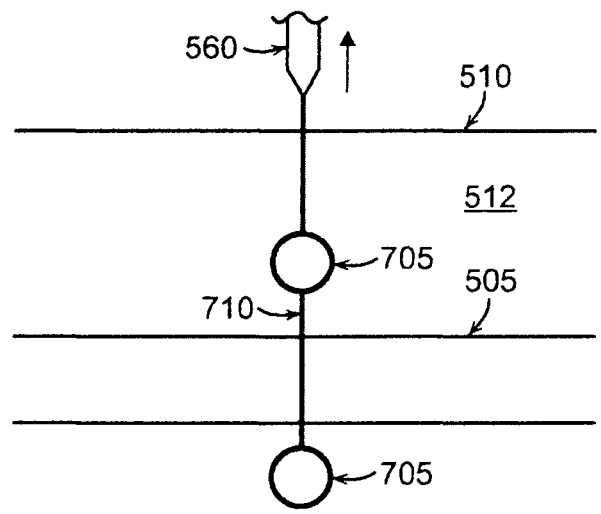

In another form of the invention, and looking now at FIGS. 143-148, a pair of balloons 705, which may be made of a polymer, or a thin metal or other material, and may be made out of an elastomer, e.g., latex or silicone, are selectively inflated by an inflation line 710, may be used to establish temporary occlusion of a blood vessel. More particularly, as seen in FIGS. 143 and 144 a needle 560 is passed from the surface of the skin 510, through intervening tissue 512 and through a blood vessel 505. Then a deflated balloon 705 (and its inflation line 710) is passed through needle 560 and the needle is deployed on the far side of blood vessel 505 (FIG. 145). Then needle 560 is retracted, paying out inflation line 710 as it goes (FIG. 146). On the near side of blood vessel 505, a second balloon 505 is positioned (in its deflated condition) on the near side of blood vessel 505, and then needle 560, paying out inflation line 710 as it goes, is retracted out of the tissue (FIG. 147).

Figure 148:
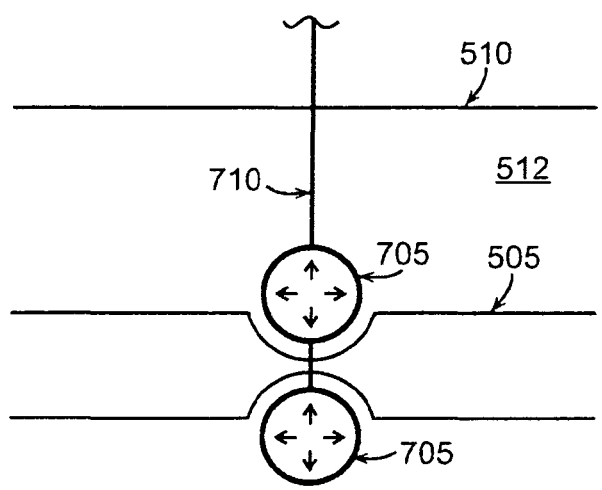

Then inflation line 710 is used to inflate both balloons 705, whereby to occlude blood vessel 505 (FIG. 148).

When temporary occlusion is to be withdrawn, balloons 705 are deflated using inflation line 710, and then the two balloons are pulled free of the anatomy by pulling proximally on inflation line 710.

Figure 149:
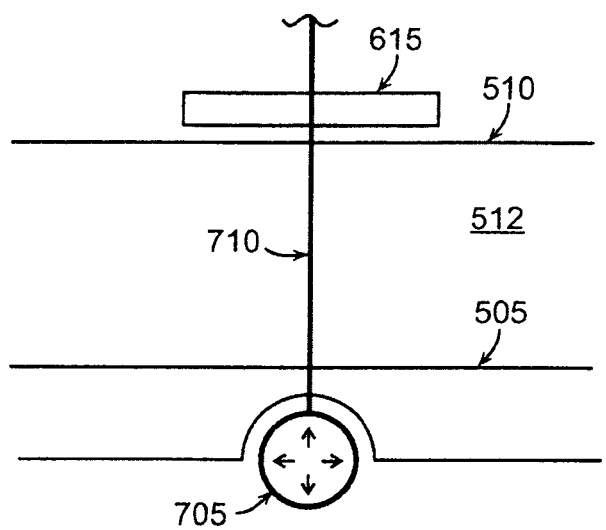
FIG. 149 is a schematic view showing yet another temporary occluder formed in accordance with the present invention.

In another form of the invention, and looking now at FIG. 149, a balloon 705 may be positioned on the far side of the blood vessel, a cap 615 may be positioned about inflation line 710 at the surface of skin 510, balloon 705 may be inflated and then tension pulled between inflated balloon 705 and cap 615 so as to occlude blood vessel 505.

When temporary occlusion is to be withdrawn, balloon 705 is deflated using inflation line 710, and then balloon 705 is pulled free of the anatomy by pulling proximally on inflation line 710.

Figure 150:
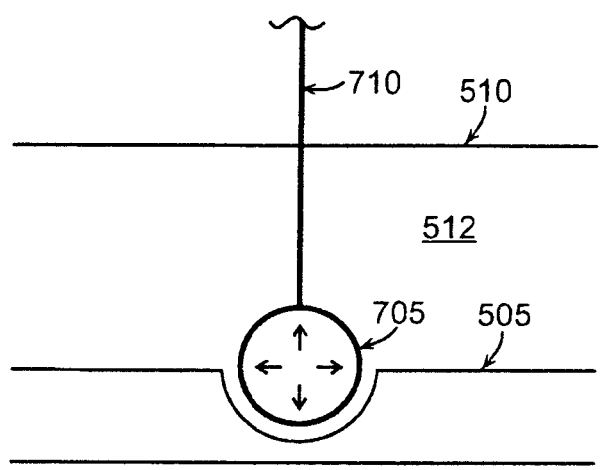
FIG. 150 is a schematic view showing another temporary occluder formed in accordance with the present invention.

In still another form of the invention, and looking now at FIG. 150, a balloon 705 may be positioned on the near side of the blood vessel, and then inflated using inflation line 710 so as to bear against blood vessel 505 and thereby occlude the blood vessel. Thus, in this form of the invention, temporary occlusion can be achieved without penetrating the blood vessel.

When temporary occlusion is to be withdrawn, balloon 705 is deflated using inflation line 710, and then balloon 705 is pulled free of the anatomy by pulling proximally on inflation line 710.

The balloon(s) 705 may be filled with air, water or a compound of higher molecular weight than air. The balloon 705 may also be inflated with a polymer that hardens in situ, for applications where it is desirable to permanently maintain occlusion of the blood vessel. Alternatively, balloon 705 may be inflated with a polymer that hardens in situ and thereafter bio-degrades over time.

In another embodiment of the present invention, the occluder may comprise a sealed tube having two regions that may be inflated into balloons. These balloon regions are expanded using air or liquid pressure.

In the foregoing disclosure, there is described an occluder (permanent or temporary, utilizing various constructions) which occludes a hollow structure (e.g., a blood vessel). In this respect it should be appreciated that the occluder may be positioned directly against a surface (e.g., an outer surface) of the hollow structure, or the occluder may be positioned such that an intervening structure or structures (e.g., anatomical tissue) may reside between the occluder and the hollow structure which is to be occluded. In this latter situation, the occluder applies a force to the intervening structure or structures, whereby to occlude the hollow structure which is to be occluded.

Using the Temporary Occluder to Occlude Tubular Structures Other than Blood Vessels It will be appreciated that the temporary occluder of the present invention can also be used to occlude tubular structures other than blood vessels. By way of example but not limitation, the temporary occluder of the present invention can be used to occlude other structures within the body (e.g., tubes such as fallopian tubes and/or vas deferens for temporary or permanent sterilization, ducts such as bile ducts and cystic ducts for cholecystectomy, lymphatic vessels, including the thoracic duct, fistula tracts, etc.).

Modifications of the Preferred Embodiments

It should be understood that many additional changes in the details, materials (e.g., shape memory polymers that are permanent or that dissolve over time, or carbon nanotube based), steps and arrangements of parts, which have been herein described and illustrated in order to explain the nature of the present invention, may be made by those skilled in the art while still remaining within the principles and scope of the invention.

What is claimed is:

1. A device for temporarily occluding a hollow or tubular anatomical structure comprising:
   a hollow delivery tube having a distal outlet, the delivery tube being insertable percutaneously through tissue, extraluminally of and across the hollow or tubular anatomical structure to locate the distal outlet distally of the structure;
   a distal occluder having a distal body and a first self-expandable portion extending from the body, the first self-expandable portion being configured to assume (i) a diametrically-reduced configuration when loaded into the hollow delivery tube, and (ii) a diametrically-expanded configuration when deployed from the delivery tube;
   a proximal occluder, separate from the distal occluder, and having a hollow proximal body and a second expandable portion extending from the body, the second expandable portion being configured to assume (i) a diametrically-reduced configuration when loaded into the hollow delivery tube, and (ii) a diametrically-expanded configuration when deployed from the delivery tube;
   an elongate member connected to the distal occluder and extending proximally through the delivery tube, the distal occluder, in its diametrically-reduced configuration, being sized to be advanced through the hollow body of the proximal occluder;
   the distal occluder and delivery tube being configured to enable the distal occluder to be ejected from the delivery tube independently of the proximal occluder, thereby enabling the first self-expandable portion of the distal occluder to be deployed at a location distal of the anatomical structure;
   the proximal occluder and the delivery tube being movable proximally from the deployed distal occluder to locate the distal outlet proximally of the anatomical structure,
   whereby, after deployment of the distal occluder, the proximal occluder may be separately deployed from the delivery tube proximally of the anatomical structure to enable the expanded regions of the deployed proximal and distal occluders to cooperate to occlude the anatomical structure; and
   wherein the first self-expandable portion of the distal occluder is collapsible to re-assume its diametrically-reduced configuration and be drawn back into the delivery tube in response to tensioning of the elongate member.

2. The device of claim 1, wherein at least one of the occluder bodies comprises a superelastic material.

3. The device of claim 1, wherein each of the expandable portions comprises a plurality of legs extending radially from the body of each occluder.

4. The device of claim 1, wherein the delivery tube comprises a needle having a tissue-piercing tip adapted to pass through a patient's skin and intervening tissue to a location and across the anatomical structure.

5. The device of claim 1, wherein the delivery tube comprises a needle and is configured to sequentially pierce opposing walls of the hollow or tubular anatomical structure.

6. The device of claim 1, wherein the hollow or tubular anatomical structure is mammalian and wherein a length of the elongate member is such as to extend from an occlusion site to a location external of a skin surface.

* * * * *